US010137307B2

United States Patent
Pascual-Leone et al.

(10) Patent No.: US 10,137,307 B2
(45) Date of Patent: Nov. 27, 2018

(54) IDENTIFYING INDIVIDUAL TARGET SITES FOR TRANSCRANIAL MAGNETIC STIMULATION APPLICATIONS

(71) Applicant: Beth Israel Deaconess Medical Center, Inc., Boston, MA (US)

(72) Inventors: Alvaro Pascual-Leone, Wayland, MA (US); Michael D. Fox, Brookline, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 14/401,296

(22) PCT Filed: Mar. 15, 2013

(86) PCT No.: PCT/US2013/032673
§ 371 (c)(1),
(2) Date: Nov. 14, 2014

(87) PCT Pub. No.: WO2013/172981
PCT Pub. Date: Nov. 21, 2013

(65) Prior Publication Data
US 2015/0119689 A1    Apr. 30, 2015

Related U.S. Application Data

(60) Provisional application No. 61/648,032, filed on May 16, 2012.

(51) Int. Cl.
| | |
|---|---|
| *A61N 2/00* | (2006.01) |
| *A61N 2/02* | (2006.01) |
| *A61B 5/055* | (2006.01) |

(52) U.S. Cl.
CPC .............. *A61N 2/006* (2013.01); *A61B 5/055* (2013.01); *A61N 2/02* (2013.01)

(58) Field of Classification Search
CPC ........... A61B 5/055; A61N 2/006; A61N 2/02
See application file for complete search history.

(56) References Cited

U.S. PATENT DOCUMENTS

| | | | |
|---|---|---|---|
| 2005/0033379 A1* | 2/2005 | Lozano | A61N 1/36185 607/45 |
| 2005/0113679 A1* | 5/2005 | Suryanarayanan | A61B 6/481 600/425 |

(Continued)

OTHER PUBLICATIONS

De Graaf et al., "fMRI Effective Connectivity and TMS Chronometry: Complementary Accounts of Causality in the Visuospatial Judgment Network", PLoS One, vol. 4, Issue 12, Dec. 2009, pp. 1-11.*

Nierhaus et al., "fMRI for the assessment of functional connectivity", Neuroimaging—Methods, InTech, Edited by Prof. Peter Bright, Published Feb. 2012, Available online from: http://www.intechopen.com/books/neuroimaging-methods/fmri-for-the-assessment-of-functional-connectivity.*

(Continued)

*Primary Examiner* — Katherine Fernandez
(74) *Attorney, Agent, or Firm* — Wolf, Greenfield & Sacks, P.C.

(57) ABSTRACT

Techniques for identifying individual target sites for application of transcranial magnetic stimulation (TMS) to a brain of a patient for treatment of neurological and psychiatric disorders. The identification of the target TMS stimulation sites may be based on using functional connectivity magnetic resonance imaging (fMRI) to determine cortex regions of the brain that are functionally connected to other regions of the brain that may be stimulated to decrease symptoms of depression and other disorders. For example, target stimulation sites may be identified in the left dorsolateral prefrontal cortex (DLPFC) to remotely modulate the activity in a subgenual cingulate region and other limbic regions functionally connected with the DLPFC. TMS may be applied to the patient's head at the identified target TMS sites to treat depression and other neurological and psychiatric disorders.

19 Claims, 23 Drawing Sheets

(56) References Cited

U.S. PATENT DOCUMENTS

| | | | |
|---|---|---|---|
| 2006/0217781 A1* | 9/2006 | John | A61N 1/36017 |
| | | | 607/45 |
| 2008/0208285 A1 | 8/2008 | Fowler et al. | |
| 2010/0036453 A1* | 2/2010 | Hulvershorn | A61B 5/055 |
| | | | 607/45 |
| 2011/0275881 A1* | 11/2011 | Aho | A61N 2/02 |
| | | | 600/13 |
| 2011/0301431 A1* | 12/2011 | Greicius | G01R 33/4806 |
| | | | 600/300 |
| 2011/0307030 A1 | 12/2011 | John | |

OTHER PUBLICATIONS

Eklund et al., "A GPU Accelerated Interactive Interface for Exploratory Functional Connectivity Analysis of fMRI Data", Proceedings from IEEE International Conference on Image Processing (ICIP), Brussels Belgium, 2011, pp. 1621-1624.*
Liang et al., "Anticorrelated Resting-state Functional Connectivity in Awake Rat Brain", Neuroimage, vol. 59, Issue 2, pp. 1190-1199, Jan. 16, 2012.*
International Search Report dated Jun. 17, 2013 from corresponding International Application PCT/US2013/032673.
International Preliminary Report on Patentability for Application No. PCT/US2013/032673 dated Nov. 27, 2014.
U.S. Appl. No. 13/744,869, filed Jan. 18, 2013, Pascual-Leone et al.
PCT/US2013/032673, dated Nov. 27, 2014, International Preliminary Report on Patentability.

* cited by examiner

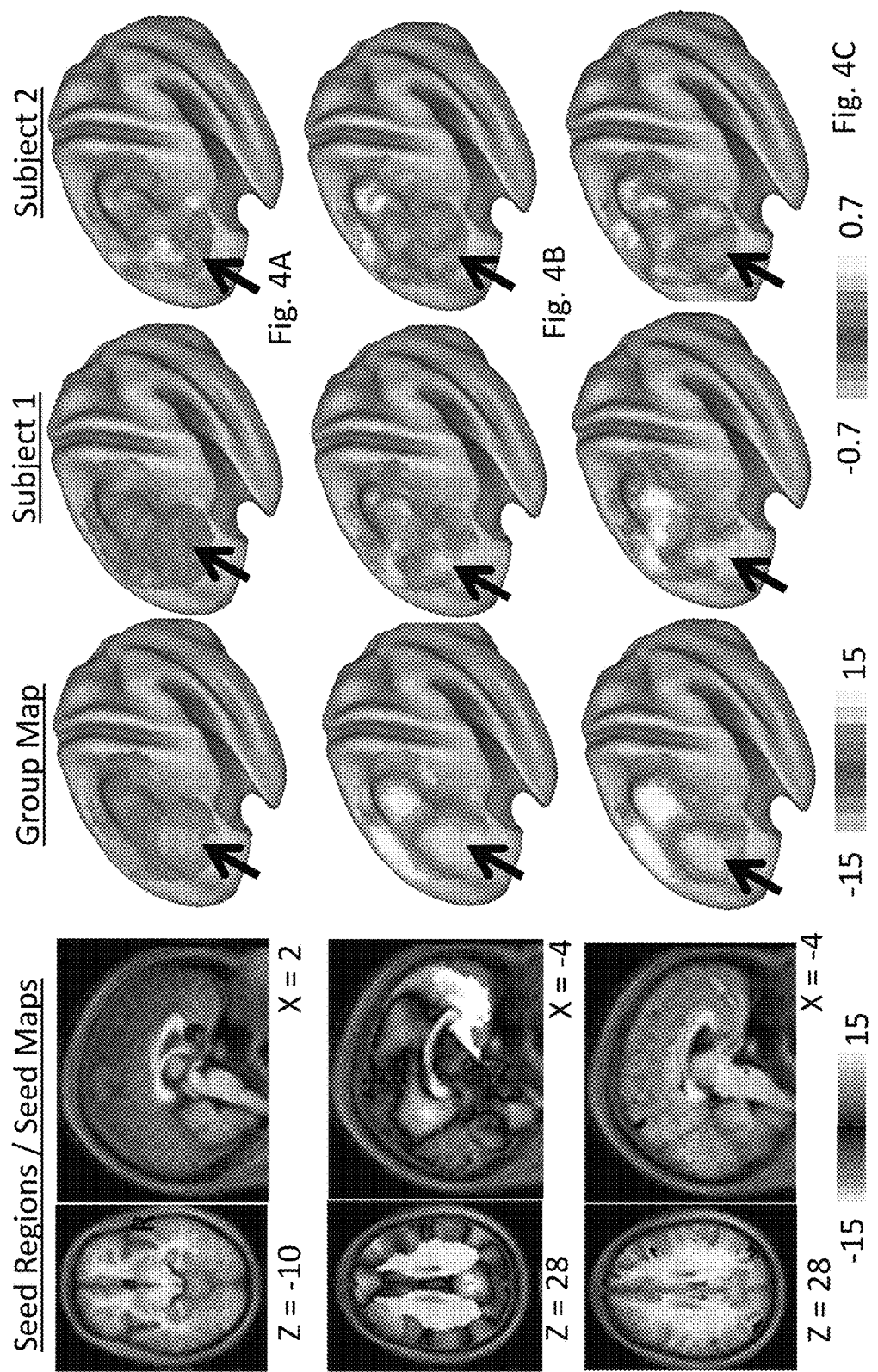

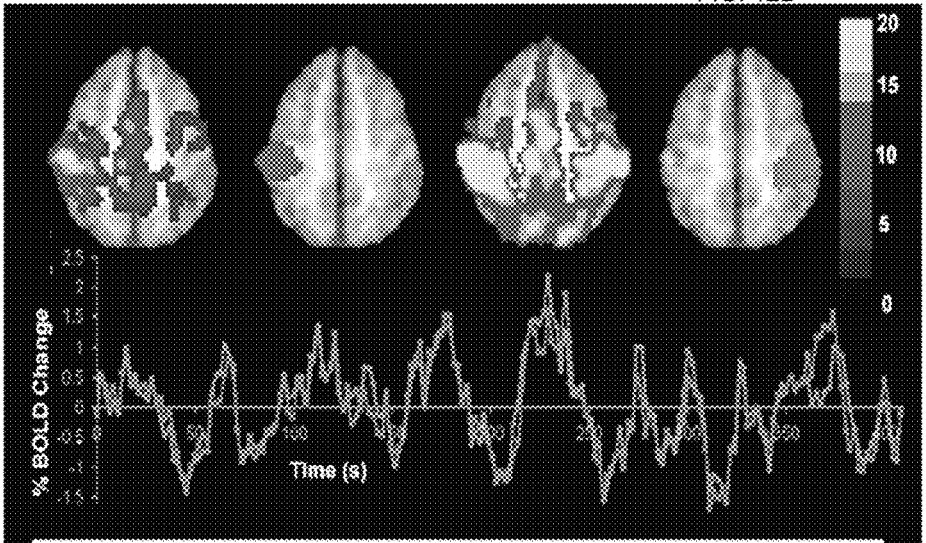
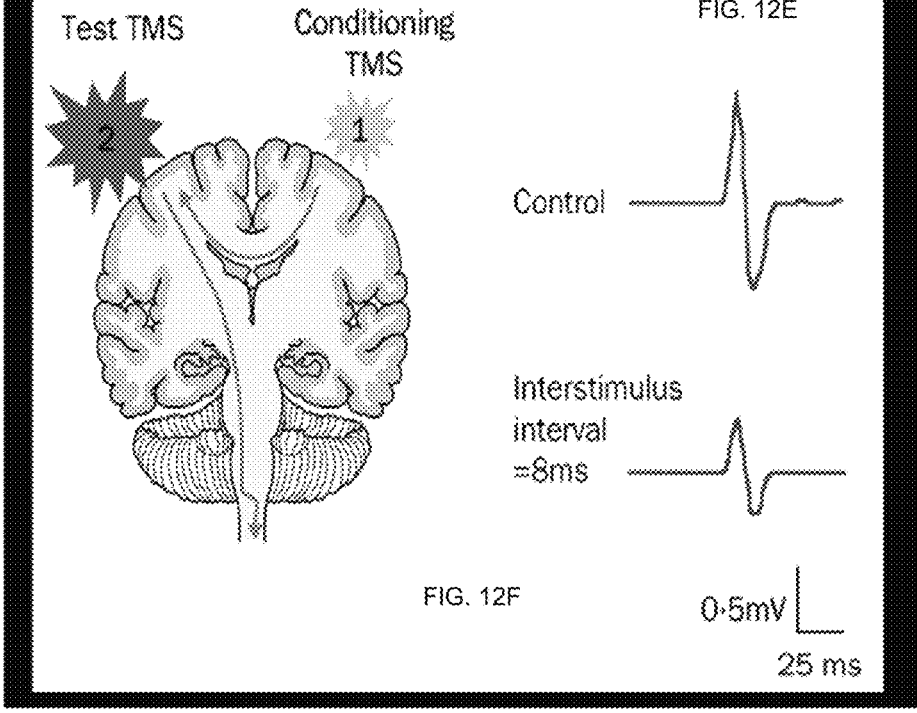

More Effective 5cm    Less Effective 5cm

Fitzgerald Target    Avg. 5cm Target

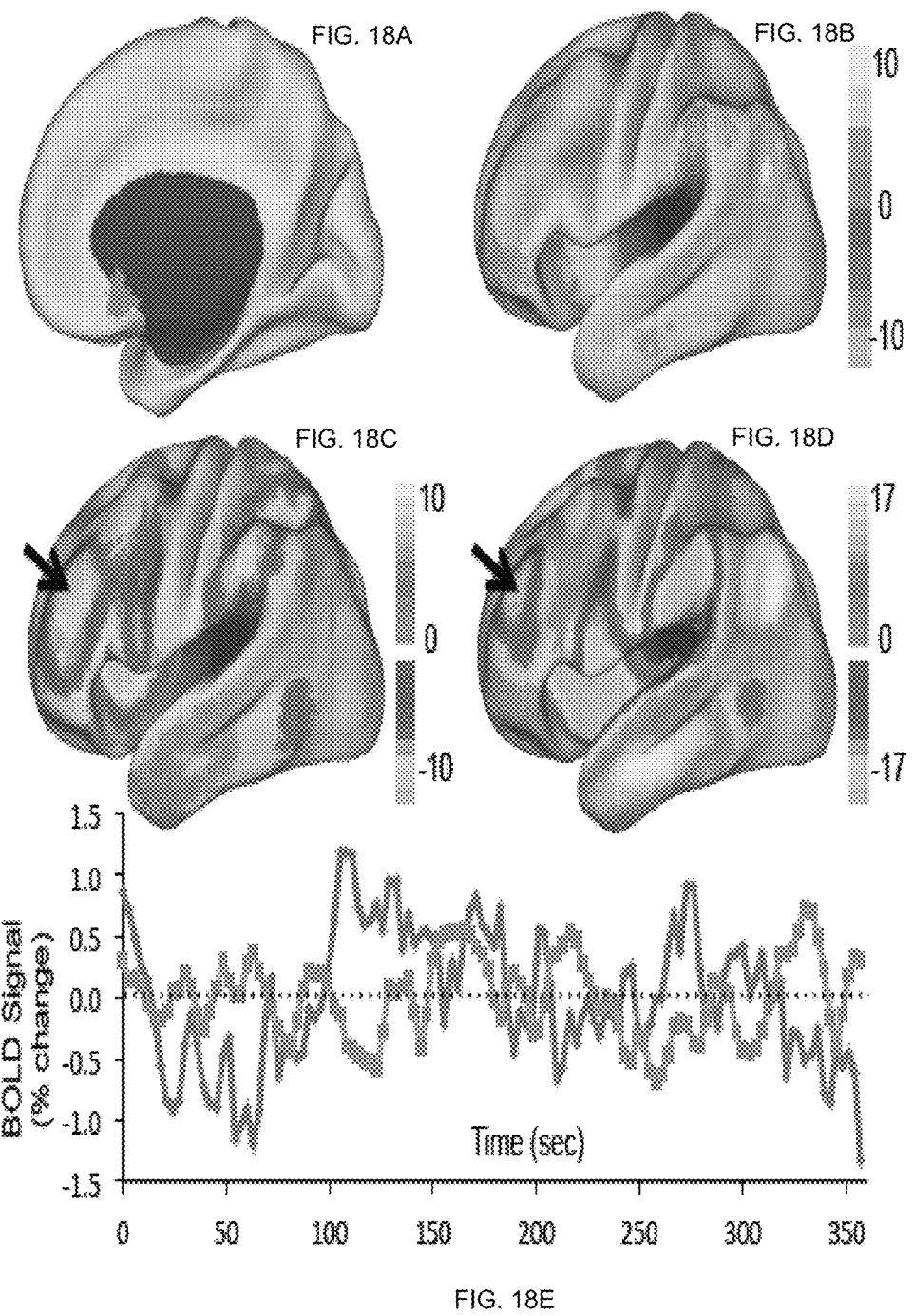

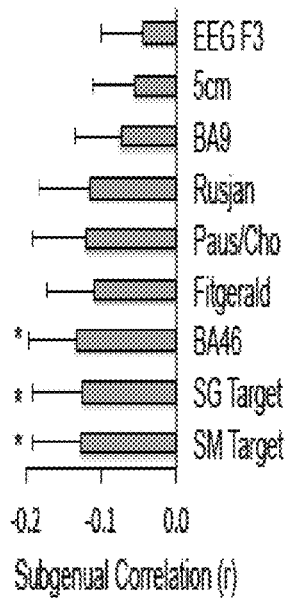
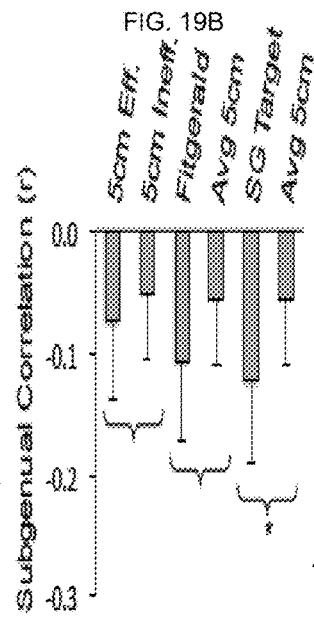
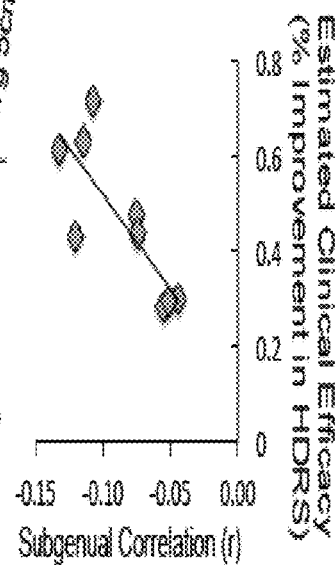
FIG. 19A  FIG. 19B  FIG. 19C
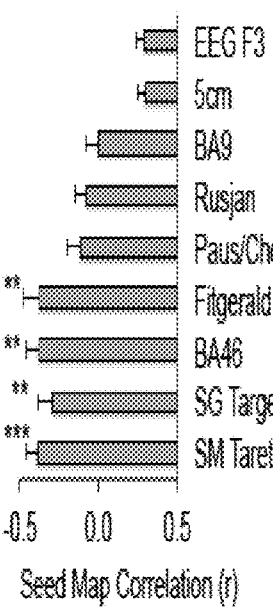
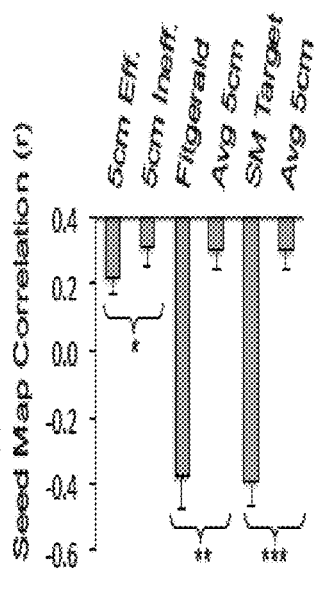
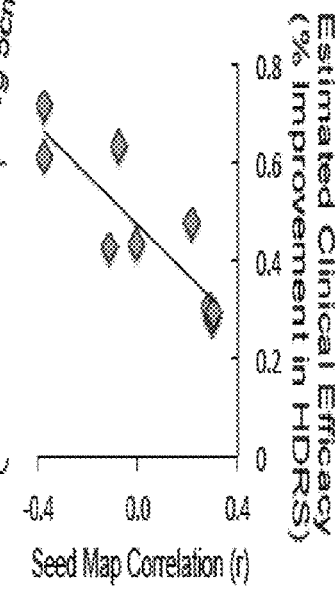
FIG. 19D  FIG. 19E  FIG. 19F

US 10,137,307 B2

IDENTIFYING INDIVIDUAL TARGET SITES FOR TRANSCRANIAL MAGNETIC STIMULATION APPLICATIONS

RELATED APPLICATIONS

This application is the national phase of International Application No. PCT/US2013/032673, filed on Mar. 15, 2013, which claims priority under 35 U.S.C. § 119(e) to U.S. Provisional Application Ser. No. 61/648,032, filed on May 16, 2012, which applications are incorporated herein by reference to the maximum extent allowable by law.

FEDERALLY SPONSORED RESEARCH

This invention was made with government support under grant number NS065743 awarded by the National Institute of Neurological Disorders and Stroke. The government has certain rights in the invention.

BACKGROUND

Transcranial magnetic stimulation (TMS) provides a non-invasive procedure for generating magnetic fields to induce stimulating electric current to desired areas of the human body, typically targeted areas of the brain. Repetitive transcranial magnetic stimulation (rTMS) has been shown useful in treatment of a variety of neurological and psychiatric disorders (Burt et al., 2002; Fregni and Pascual-Leone, 2007; Hallett, 2007). Applying rTMS at different frequencies may allow enhancing, suppressing, or interfering with underlying neuronal activity. Further, the effects of TMS can propagate beyond the site of stimulation, impacting a distributed network of brain regions (Ferreri et al., 2010; Lisanby and Belmaker, 2000; Ruff et al., 2009; Siebner et al., 2009; Valero-Cabre et al., 2007; Valero-Cabre et al., 2005).

The rTMS technique has been used as a non-invasive treatment for a variety of medical conditions. Applications for rTMS include, but are not limited to, psychiatric disorders, such as depression, hallucinations, obsessions, and drug craving, and different neurologic diseases.

It has been recognized that many manifestations of neurological and psychiatric diseases are not solely a result of an abnormality in one isolated region of the brain, but represent alterations in brain networks and connectivity. Accordingly, interactions and connections between regions of the brain are becoming a focus of neurological research.

The subgenual cingulate region has been shown to decrease its activity in response to multiple treatment modalities and has been used as a target of deep brain stimulation (Mayberg et al., 2000; Drevets et al., 2008; Mayberg et al., 2005). Another region that has been used clinically for the treatment of depression is the left dorsolateral prefrontal cortex (DLPFC) (Mayberg, 2007; Drevets et al., 2008).

SUMMARY

Some embodiments provide a method for identifying individual target sites for application of transcranial magnetic stimulation (TMS) to the patient's brain for treatment of depression and other disorders. The identification of the target stimulation sites for a particular patient may improve efficacy of TMS for treatment of different neurological and psychiatric disorders.

One or more target stimulation sites may be identified in regions of the brain that may be suitable for TMS application and that may be functionally connected to other regions of the brain that may be stimulated to decrease depression symptoms. For example, stimulation sites may be identified in the left dorsolateral prefrontal cortex (DLPFC) to remotely modulate the activity in a subgenual cingulate region and other limbic regions that are functionally connected with the DLPFC. In some embodiments, individual target sites that correlate negatively with the subgenual cingulate cortex may be selected, as such sites may be clinically effective for treatment of depression.

In some embodiments, the method for selecting TMS target sites may be based on identification of functional connectivity between different regions of the brain using functional connectivity magnetic resonance imaging (fMRI). The fMRI data may be obtained in a suitable manner and then used for a functional connectivity analysis, which may involve identifying one or more regions of interest (ROIs) and determining activity of what other region(s) of the brain correlate, either negatively or positively, with an activity in the one or more ROIs. Resting state fMRI may be used, which is based on blood oxygenation level dependent (BOLD) signal reflecting spontaneous neural activity.

In some embodiments, an ROI may comprise a seed in the subgenual cingulate cortex, or in any other region of the brain. An ROI may be defined based on one or more ROIs previously shown to modify their activity based on treatment using TMS and other modalities of brain stimulation. Additionally or alternatively, the ROI may comprise one or more seed maps. A seed map may be derived from comparing stimulation sites identified as effective to sites identified as ineffective for treatment of depression. As another example, the seed map may comprise a functional connectivity map of a portion of the brain or the entire brain to an ROI. Though, an ROI may be selected in any other suitable manner.

Once one or more ROIs and/or one or more seed maps are selected, coordinates of one or more stimulation sites may be computed, to identify one or more individual target sites for application of TMS. TMS may then be applied to the patient's head at the identified target sites to treat depression or other disorders. TMS may comprise a single-pulse TMS, a repetitive TMS (rTMS), or any other suitable type of TMS. Additionally or alternatively, other brain stimulation techniques may be utilized.

In some embodiments, a device may be provided for implementing the techniques for identifying individual target sites for TMS and applying TMS to the identified target sites. The device may be associated with one or more stimulation coils that may be positioned at the identified target sites so as to deliver TMS to the patient for treatment of depression and other neurological and psychiatric disorders.

BRIEF DESCRIPTION OF DRAWINGS

FIGS. 4A-4C illustrate identification of connectivity-based TMS targets in the left dorsal lateral prefrontal cortex (DLPFC) at the group and single subject level. Resting state functional connectivity maps are shown for the population (group) and two individual subjects (subject 1, 2) for a seed region in the subgenual cingulate (FIG. 4A) a seed map based on subgenual connectivity (FIG. 4B) and a seed map based on connectivity differences between effective and ineffective DLPFC TMS sites (FIG. 4C). Surface-based maps are masked to show only voxels in the left DLPFC. Black arrows identify a potential stimulation site at the group level that is different between subjects 1 and 2.

FIG. 12A-12F illustrate connectivity between the motor cortices assessed with resting stale functional Connectivity MRI and dual-coil stimulation with TMS. The top panel shows fMRI activation in response to a right hand button press (FIG. 12A), a left somatomotor region of interest (FIG. 12B), resting state functional connectivity with this left somatomotor cortex region of interest (FIG. 12C), a right somatomotor cortex region of interest defined on the basis of the resting state functional connectivity (FIG. 12D), and spontaneous fluctuations recorded in the left (pink line) and right (blue line) somatomotor cortices during the resting state conditions showing significant interhemispheric correlation (FIG. 12E) (modified with permission from Fox et at, 2007). The lower panel (FIG. 12F) shows the effect of transcallosal inhibition using dual-coil TMS. When a conditioning pulse is delivered to the left motor cortex 8 ms before the test pulse is delivered to the right motor cortex the motor evoked potential recorded from the left hand is significantly decreased (modified with permission from Kobayashi and Pascual-Leone, 2003).

FIG. 13A: Regional CBF changes assessed with PET in response to double-pulse TMS to the left DLPFC (modified with permission from Paus el at. 2001). FIG. 13B: BOLD changes assessed with fMRI in response to 1 Hz TMS to the left DLPFC (modified with permission from Li or at., 2004). FIG. 13C: Dopamine release (decreases in [11C]FLB 457 binding potential) in response to 10 Hz TMS to the left DLPFC (modified with permission from Cho and Strafella, 2009). FIG. 13D: Anti-correlated networks identified using resting state functional connectivity MRI based on correlations within a system and negative correlations between systems (modified with permission from Fox et al., 2005).

FIG. 18 illustrates identification of optimized left DLPFC TMS targets for depression respectively). Peak anticorrelations were identified in the left DLPFC that could serve as optimized targets for focal brain stimulation. fMRI time courses from the subgenual region of interest (red) and the anticorrelated left dorsal lateral prefrontal cortex (green) are shown for a representative subject (r=−0.23). based on functional connectivity. Regional time courses were extracted from our seed region in the subgenual cingulate (FIG. 18A) and our efficacy-based seed map (FIG. 18B) and used to generate resting state functional connectivity maps (FIGS. 18C and 18D respectively). Peak anticorrelations were identified in the left DLPFC that could serve as optimized targets for focal brain stimulation. fMRI time courses from the subgenual region of interest (red) and the anticorrelated left dorsal lateral prefrontal cortex (green) are shown for a representative subject (r=−0.23) as shown in FIG. 18E.

FIG. 19 illustrates replication of principal findings in patients with major depressive disorder. Time course correlations are shown between regions of interest in the dorsal lateral prefrontal cortex (DLPFC) and the subgenual seed region (FIGS. 19A-19C) or the efficacy-based seed map (FIGS. 19D-19F). Similar to normal subjects, there is an anticorrelation between TMS targets in the DLPFC and the subgenual (FIG. 19A). Paired comparisons of effective versus less effective DLPFC targets show the same trend as normal subjects and a significant difference between the optimized DLPF target identified using the subgenual seed region (SG Target) and the average 5 cm target (FIG. 19B). Also similar to normal subjects, there is a strong relationship between estimated clinical efficacy (using the Herbsman equation) and anticorrelation with the subgenual (FIG. 19C; r2=0.66, P<0.005). Using the efficacy-based seed map rather than the small subgenual seed region produces similar but more robust results including examination of regional time course correlations (FIG. 19D), paired comparisons (FIG. 19E), and the correlation between functional connectivity and estimated clinical efficacy (FIG. 19F; $r^2$=0.76, P<0.001). Labels for DLPFC ROIs are as in FIGS. 16 and 17A-17F with the addition of optimized DLPFC targets identified in normal subjects using the subgenual seed region (SG Target) and the efficacy-based seed map (SM Target). *P<0.05, P<0.001, *P<$10^{-4}$.

FIG. 20 illustrates a priori defined regions of interest (ROI) not otherwise shown in the primary figures.

Figure 23A:
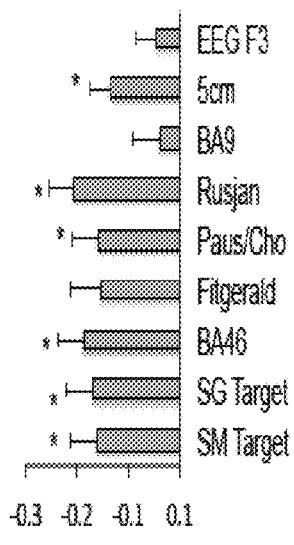
FIGS. 23A-23F illustrate replication of principal findings in 11 control subjects from the same dataset as the 13 depressed patients. Time course correlations are shown between regions of interest in the dorsal lateral prefrontal cortex (DLPFC) and the subgenual seed region (FIGS. 23A-23C) or the efficacy-based seed map (FIGS. 23D-23F).
Figure 23B:
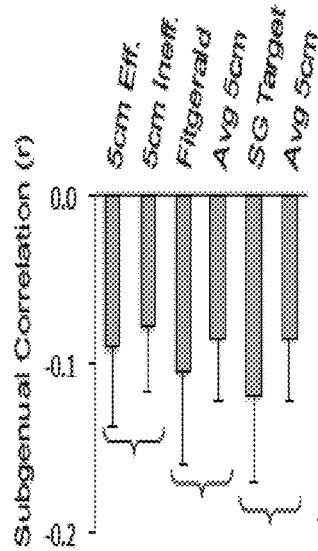
Figure 23C:
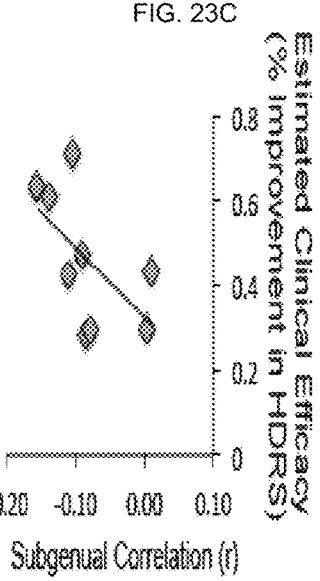
Figure 23D:
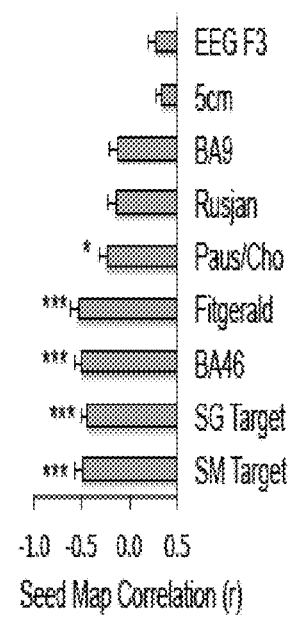
Figure 23E:
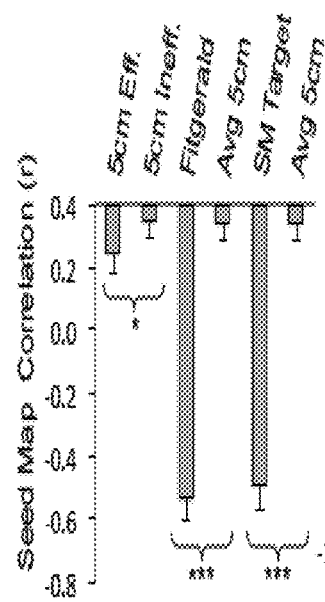
Figure 23F:
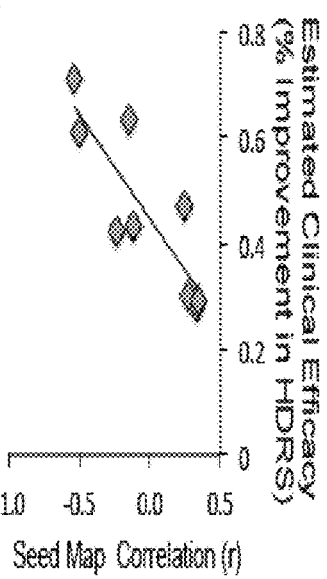

There is an anticorrelation between TMS targets in the DLPFC and the subgenual (FIG. 23A). Paired comparisons show a trend towards stronger anticorrelation with more effective sites (FIG. 23B). The relationship between estimated clinical efficacy (using the Herbsman equation) and anticorrelation with the subgenual is similar to that previously observed (FIG. 23C; $r^2$=0.34, P=0.051). Using the efficacy-based seed map rather than the small subgenual seed region produces similar but more significant results including examination of regional time course correlations (FIG. 23D), paired comparisons (FIG. 23E), and the correlation between functional connectivity and estimated clinical efficacy (FIG. 23F; $r^2$=0.73, P<0.005). Labels for DLPFC ROIs are as in FIGS. 16 and 17A-17F with the addition of optimized DLPFC targets identified in normal subjects using the subgenual seed region (SO Target) and the efficacy-based seed map (SM Target). *P<0.05, P<0.001, *P<$10^{-4}$. Overall, this small population of 11 subjects shows the same pattern of results seen in both our original population of 98 normal subjects and the 13 subjects with depression. There are no significant differences between these 11 normal subjects and the 13 subjects with depression from the same dataset.

DETAILED DESCRIPTION

The applicants have recognized and appreciated that identifying individual target sites for application of TMS to a patient, based on a patient's condition and individual brain characteristics, may improve efficacy of TMS treatment of depression and other neurological and psychiatric disorders.

TMS may be used as a non-invasive treatment for a variety of medical conditions, including psychiatric disorders, such as depression, hallucinations, etc. Depression involves a distributed network of cortical and limbic regions including the dorsolateral prefrontal cortex (DLPFC), hippocampus, and the subgenual cingulate.

Deep limbic regions of the brain, such as the subgenual cingulate cortex, may be functionally connected with other regions of the brain, such as the left DLPFC. The subgenual cingulate has been observed to be hyperactive in depression and a decrease in this hyperactivity is associated with antidepressant response (Mayberg et al., 2007; Drevets et al., 2008; Koenigs and Grafman, 2009). The left DLPFC, however, has been shown to be hypoactive in depression and an increase in activity may be associated with antidepressant response (Koenigs and Grafman, 2009; Fitzgerald et al. 2006).

It has been shown that clinical efficacy of different DLPFC stimulation sites may be related to the strength of the anticorrelation of each site with the subgenual cingulate cortex. Specifically, in patients with depression, the activity of the subgenual cingulate cortex has been found to increase, while the activity of the DLPFC has been found to decrease.

Existing TMS-based techniques are used to induce stimulating electrical current in the underlying cortical surface, whereas deeper limbic regions, including the subgenual, may not be directly or selectively stimulated with stimulation coils. The left DLPFC, which has been shown to be functionally connected with the subgenual cingulate, is more accessible for application of TMS. Accordingly, TMS may be used to induce an antidepressant effect on the subgenual cingulate cortex by stimulating specific areas in the DLPFC.

To stimulate one or more areas in the DLPFC, stimulation sites within the DLPFC may need to be identified. Accordingly, in some embodiments, the functional connectivity between subgenual cingulate and the left DLPFC may be used to identify stimulation sites within the left DLPFC. The one or more stimulation sites may be identified in the left DLPFC to remotely module neural processing activity in the subgenual cingulate. In some embodiments, stimulation sites with the DLPFC may be identified to modulate activity in other limbic regions that are functionally connected to the DLPFC.

Previous findings suggested that left DLPFC TMS may have distributed effects on deeper limbic regions, such as the subgenual cingulate (Padberg and George, 2009; George et al., 1995; George et al., 1997), but did not reveal how application of TMS to the DLPFC exerted its antidepressant effect. In this respect, the applicants have discovered that DLPFC stimulates sites for application of TMS that were shown to be more clinically efficient may be more negatively correlated, or anticorrelated, with the subgenual cingulate.

Accordingly, in some embodiments, target stimulation sites that correlate negatively with the subgenual cingulate cortex may be selected, since such stimulation sites may be clinically effective for treatment of depression. Application of TMS to the target stimulation sites identified for a patient may improve efficiency of treatment of depression and other neurological and psychiatric disorders.

The applicants have appreciated that functional magnetic resonance imaging (fMRI) techniques may be used to acquire data to guide selection of target stimulation sites for application of TMS to a patient. The fMRI techniques include analysis of low-frequency fluctuations in time courses of fMRI signal intensity to identify correlations in spontaneous fluctuations in the blood oxygen level dependent (BOLD) signal. (Fox and Raichle, 2007; van den Heuvel and Hulshoff Pol, 2010; Deco et al., 2011).

In some embodiments, resting state fMRI may be using for assessing functional connectivity in the brain. In contrast to task-based fMRI studies where a patient is instructed to perform a task before fMRI data is obtained from the patient, resting state fMRI may be used to examine BOLD fluctuations in the absence of any external stimuli, while the patient rests in a scanner. Resting state fMRI may be more advantageous than the task-based fMRI for clinical applications due to, for example, improved signal-to-noise ratio, reduced need for patient compliance, avoidance of task performance confounds, and expanded patient populations. (Fox and Greicius, 2010). Though, it should be appreciated that embodiments are not limited with respect to any specific technique that may be used to assessing functional connectivity in the brain.

In some embodiments, fMRI may be used to measure functional connectivity between different regions of the brain, to reveal positive and negative correlations between different brain regions. Further, the applicants have recognized and appreciated that fMRI techniques may be advantageously combined with TMS so that TMS may be used to manipulate functional connectivity identified using fMRI.

Functional connectivity analysis may depend on identification of one or more regions of interest, which may also be referred to as "seeds." Cross-correlating time courses of fMRI images of a region of interest with other regions of the brain may reveal which regions in the brain are correlated (either negatively or positively), and therefore functionally connected, with the region of interest. In this way, a correlation map of any suitable type may be created for any region of interest. In some embodiments, the correlation map between a region of interest and each voxel in the brain may be generated. Regions in the brain that are co-activated with the region of interest may be identified as positively correlated regions, and regions in the brain that do not exhibit activity when the region of interest is activated may be identified as regions that correlate negatively with the region of interest.

Accordingly, the applicants recognized and appreciated that differences in functional connectivity may be related to differences in clinical efficacy across a distributed set of cortical and limbic regions. In some embodiments, TMS sites in the DLPFC that are negatively correlated (i.e., anticorrelated) with the subgenual cingulate may be characterized as clinically efficient sites. Connectivity-based stimulation for treatment of depression coordinates may be located in one or more Brodmann area (BA).

In some embodiments, functional connectivity with remote regions, such as subgenual cingulate, may predict average clinical efficacy of different sites for application of TMS. Accordingly, a combination of TMS and fMRI techniques may allow a non-invasive manipulation of brain connectivity to treat pathological interactions in the brain network of the patient.

Figure 1:
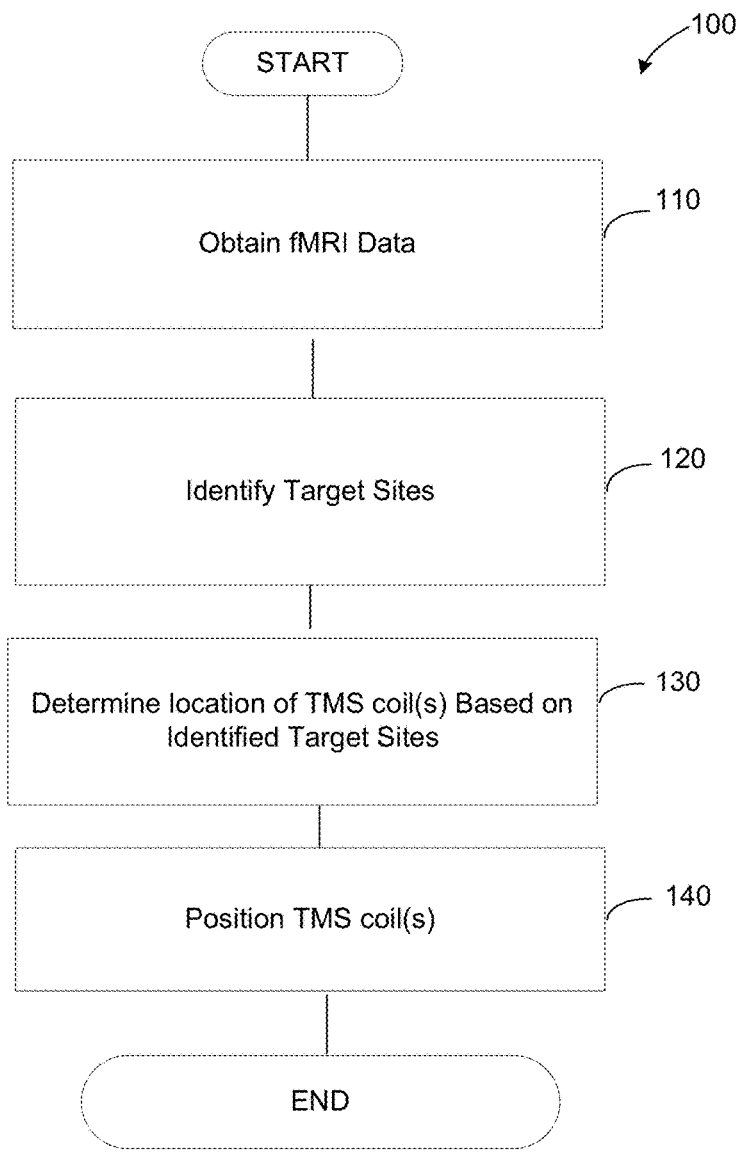
FIG. 1 shows generally a process 100 of identifying one or more target stimulation sites for an individual patient for treatment of depression and other neurological and psychiatric disorders and applying one or more TMS coils to the target sites.

FIG. 1 shows generally a process 100 of identifying one or more target stimulation sites for an individual patient for treatment of depression and other neurological and psychiatric disorders and applying one or more TMS coils to the target sites. Process 100 may start at any suitable time. At block 110, fMRI data on the patient may be obtained. The fMRI data may be acquired using a suitable imaging system, which may also obtain structural images of the patient's brain, along with the functional data. The imaging system may be located either locally or remotely.

At block 120, one or more individual target sites for TMS may be identified, using the techniques in accordance with some embodiments. For example, the individual target sites may be identified based on functional connectivity analysis of fMRI data, by correlating fMRI time courses at one or more ROI with time courses at a portion of the brain or the entire brain (e.g., all voxels in the brain), to identify one or more sites that correlate with the ROI(s). In some embodiments, the ROIs may comprise one or more ROIs in the subgenual cingulate and the individual target sites may comprise sites in the left DLPFC that correlated negatively with the subgenual ROIs. It should be appreciated that any other ROIs of different types may be identified in the brain for the functional connectivity analysis. The individual target sites may be of any suitable size and shape.

Once one or more individual target sites for TMS have been identified, a location of one or more TMS coils may be determined based on the identified target sites, at block 130. Coordinates for application of the TMS coils may be identified as brain coordinates and skull-based measurements, or in any other suitable manner.

Regardless of how the location of the TMS coils is determined at block 130, the one or more TMS coils may then be positioned so as to target the identified individual sites in the brain of the patient, at block 140. The TMS may be administered to treat different conditions and disorders. Process 100 may then end. However, it should be appreciated that TMS application may involve multiple TMS stimulations or sessions. It should further be appreciated that process 100 may be repeated for the same patient—for example, to monitor an efficacy of the treatment. Different stimulation sites may be selected based on the monitoring. Further, the treatments may vary in the duration of the stimulation, frequency of treatment, frequency and power level of the emitted fields, and with respect to any other suitable parameters. It should be appreciated that embodiments are not limited to any particular TMS treatment for depression and other neurological and psychiatric disorders.

Figure 2:
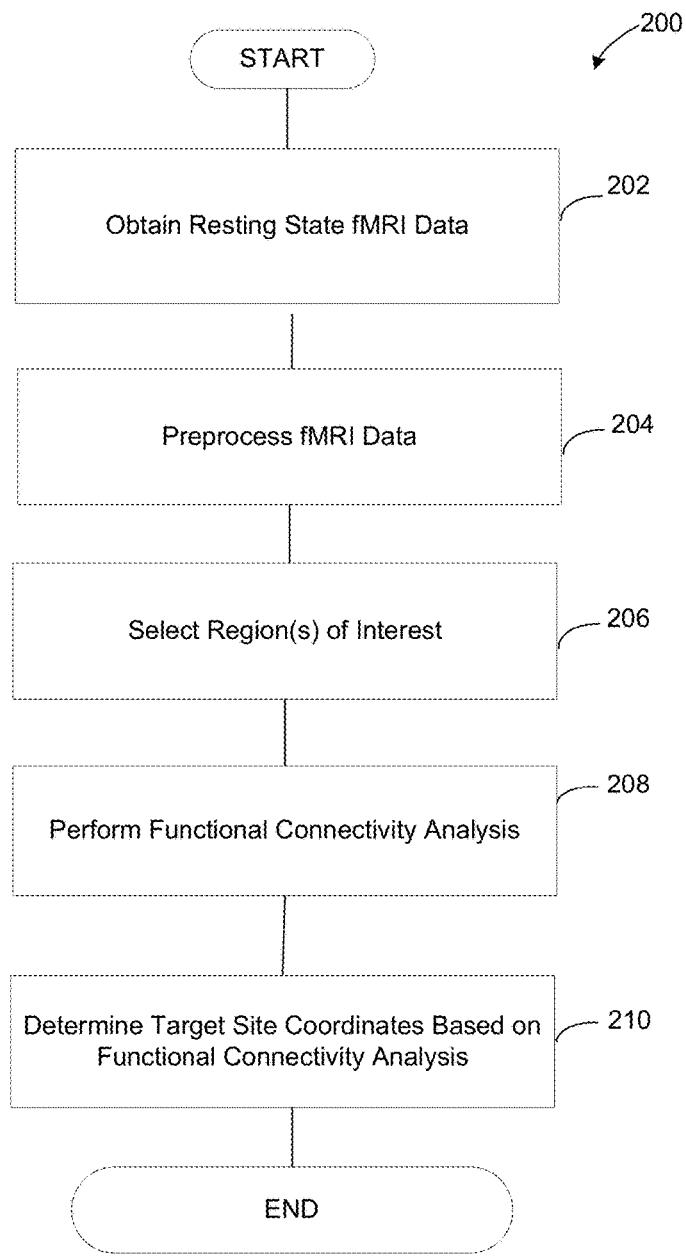
FIG. 2 illustrates a process 200 of identifying one or more individual target sites for TMS of the brain of a patient.

In some embodiments, individual stimulation sites for application of TMS to the patient's brain may be identified based on functional connectivity analysis. FIG. 2 illustrates a process 200 of identifying one or more individual target sites for TMS of the brain of a patient. Process 200 may start at any suitable time. At block 202, resting state fMRI data may be obtained from the patient, in any suitable manner.

In some embodiments, the brain of the patient may be imaged using an MRI technique, to obtain structural and functional (fMRI) images. The imaging may be performed locally—e.g., at the same site where the TMS procedures are performed, or at a suitable remote location. For example, the imaging may be done in one medical facility, and processing of the obtained data and the TMS procedures may be performed at another facility. Though, it should be appreciated that the imaging, data processing and the treatment may be performed at any one or more of suitable locations, as embodiments are not limited in this respect.

The resting state fMRI imaging may be performed in any suitable manner, as known in the art or developed in the future. For example, in one embodiment, a 3T Siemens whole body MRI System with a phased array head coil may be utilized. Two 6.2 min long (124 frames) resting state fMRI scans (TR=3000 ms, TE=30 ms, FA=8.5°, 3×3×3 mm voxels, FOV=216, 47 axial slices with interleaved acquisition and no gap) may be performed on the patient. Structural images may be obtained as a high-resolution multi-echo T1-weighted magnetization-prepared sequence (TR=2200 ms, TI=1100 ms, TE=1.54 ms for image 1 to 7.01 ms for image 4, FA=7°, 1.2×1.2×1.2 mm voxels, FOV=230) (van der Kouwe et al., 2008). It should be appreciated that the above parameters are shown by way of example only, as any other suitable parameters may be substituted.

In another embodiment, fMRI imaging may be performed on a 3-T General Electric Signa scanner using a standard whole-head coil. A patient may complete a 10 minute long (300 frames) resting state fMRI scan using a T2*-weighted gradient echo spiral in/out pulse sequence (TR=2000 ms, TE=30 ms, FA=80°, 3.4×3.4×4.5 mm voxels, 31 axial slices with interleaved acquisition, 4 mm thickness, and 0.5 mm gap). Suitable instructions may be given to the patient for the resting state fMRI. For example, the patient may be instructed to "lie still with your eyes closed, try not to think of any one thing in particular and try not to fall asleep." Structural images may be a high-resolution T1-weighted spoiled gradient recalled 3-D MRI sequence (TR=40 ms, minimum TE, FA=11°, 0.86×0.86×1.2 mm voxels, 128 axial slices with interleaved acquisition). It should be appreciated that the above parameters are shown by way of example only, as any other suitable parameters may be substituted. Further, it should also be appreciated that the structural and functional images may be obtained in any suitable manner, using any suitable equipment, as embodiments are not limited in this respect.

In some embodiments, fMRI data obtained as using fMRI imaging may be preprocessed using any suitable technique. Referring back to FIG. 2, at block 204, the fMRI data obtained at block 202 may be preprocessed in a suitable manner.

For example, the fMRI data may be preprocessed using an approach described in (Fox et al., 2005) as implemented in Van Dijk (Van Dijk et al., 2010). This may involve preprocessing the fMRI data to decrease image artifacts and between-slice timing differences. The fMRI data may be spatially smoothed using a Gaussian kernel—e.g., a kernel with 6 mm full-width at half-maximum, and temporally filtered (e.g., 0.009 Hz<f<0.08 Hz). Further, in some embodiments, spurious or nonspecific sources of variance may be removed by regression of the following variables: (1) six movement parameters computed by rigid body translation and rotation during preprocessing, (2) mean whole brain signal, (3) mean brain signal within the lateral ventricles, and (4) the mean signal within a deep white matter ROI. Inclusion of the first temporal derivatives of these regressors within the linear model may be accounted for the time-shifted versions of spurious variance. Though, it should be appreciated that the above preprocessing is described by way of example only, as embodiments are not limited with respect to a particular way of preprocessing fMRI data.

At block 206, one or more regions of interest (ROIs) may be selected for determining target TMS sites. The ROIs may be selected in any suitable manner. In some embodiments, the ROIs may be selected based on the patient's condition, brain characteristics, disease, and any other suitable factors.

In some embodiments, an ROI may be defined a-priori in a subgenual cingulate cortex region based on coordinates from prior studies showing reductions in subgenual activity tied to antidepressant response (Mayberg et al., 2005; Kito et al., 2008; Kito et al., 2011; Wu et al., 1999; Mayberg et al., 2000; Drevets et al., 2002; Nahaz et al., 2007), as shown in Table 1.

Subgenual coordinates identified in the literature (generally in Talairach space) may be converted into MNI space using tal2mni (e.g., using software available at http://imaging.mrc-cbu.cam.ac.uk/imaging/MniTalairach). "Talairach" may refer to an atlas coordinate space as defined by Talairach and Tournoux in 1988 (Talairach and Tournoux, 1988). After conversion to the MNI space, coordinates obtained in all of the studies may be averaged. As a result, an ROI may be generated comprising a single 10 mm sphere centered on these coordinates (6, 16, −10). The ROI may be masked—for example, to exclude voxels not included in the cerebral cortex (e.g., using the Harvard-Oxford cortical regions template available in FSL).

Additionally or alternatively, a-priori ROIs may be defined in the left DLPFC based on coordinates previously used or proposed as TMS targets for depression (Table 1) (Herwig, 2001; Herbsman, 2009; Herwig, 2003; Rajkowska, 1995; Paus, 2001; Cho 2009; Fitgerald, 2009; Rusjan, 2010). This left DLPFC region of interest may be generated so that to cover all voxels that may be considered part of the left DLPFC by combining 25 mm radius spheres centered on the coordinates for BA9, BA46 (Rajkowska and Goldman-Rakic 1995), and a 5 cm TMS site (Herbsman et al., 2009; Herwig et al., 2001). The left DLPFC ROI may be masked to eliminate voxels lying outside of grey matter as defined by the standard Harvard/Oxford grey matter template in FSL (e.g., using a threshold at an intensity of 70).

TABLE 1

Coordinates that may be used to generate a priori regions of interest (ROIs). A) Coordinates of treatment related decreases in the subgenual cingulate tied to antidepressant effect, the treatment modality used, and finally the average coordinates used to generate a priori ROI. B) Coordinates of various left dorsallateral prefrontal cortex transcranial magnetic stimulation targets suggested in the literature. For all prior studies (A and B), the published coordinates are shown in either Talairach (Tx, Ty, Tz) or MNI (MNIx, MNIy, MNIz) space along with the transformed MNI coordinates.

A) SUBGENUAL REGION

| Study | Tx | Ty | Tz | MNIx | MNIy | MNIz | Treatment |
|---|---|---|---|---|---|---|---|
| Wu et al. 1999 | 7 | 17 | −4 | 7 | 18 | −4 | Sleep Deprivation |
| Mayberg et al. 2000 | 4 | 2 | −4 | 4 | 2 | −5 | SSRI |
| Drevets et al. 2002 | 3 | 31 | −10 | 3 | 32 | −10 | SSRI |
| Mayberg et al. 2005 | −2 | 8 | −10 | −2 | 9 | −11 | DBS |
| Mayberg et al. 2005 | 10 | 20 | −4 | 10 | 21 | −4 | DBS |
| Kito et al. 2008 | 17 | 16 | −14 | 17 | 17 | −16 | TMS |
| Kito et al. 2011 | 8 | 21 | −9 | 8 | 22 | −9 | TMS |
| Nahas et al. 2007 | 0 | 8 | −16 | 0 | 9 | −19 | VNS |
| AVERAGE | | | | 5.9 | 16.3 | −9.8 | |

B) DLPFC REGIONS

| Study/Site | Tx | Ty | Tz | MNIx | MNIy | MNIz |
|---|---|---|---|---|---|---|
| Herwig 2001 5 cm Stim. Site | −42 | 17 | 52 | | | |
| Herbsman 2009 5 cm Stim. Site | −42 | 20 | 49 | | | |
| Herbsman 2009 5 cm Sham Site | −39 | 17 | 47 | | | |
| AVERAGE 5 cm Coordinates | −41 | 18 | 49 | −41 | 16 | 54 |
| Herbsman 2009 Responders | −46 | 25 | 44 | −46 | 23 | 49 |
| Herbsman 2009 Nonresponders | −41 | 19 | 50 | −41 | 17 | 55 |
| Herwig 2003 EEG (F3) Site | −37 | 27 | 44 | −37 | 26 | 49 |
| Rajkowska 1995 BA46 Definition | −44 | 40 | 25 | −44 | 40 | 29 |
| Rajkowska 1995 BA9 Definition | −36 | 40 | 38 | −36 | 39 | 43 |
| Paus 2001 TMS Target | −40 | 32 | 30 | −40 | 31 | 34 |
| Cho 2009 TMS Target | −40 | 32 | 30 | −40 | 31 | 34 |
| Fitgerald 2009 TMS Target | −46 | 45 | 35 | −46 | 45 | 38 |
| Rusjan 2010 TMS Target | −50 | 31 | 32 | −50 | 30 | 36 |

Referring back to FIG. 2, after the ROI is selected, the functional connectivity analysis may be performed at block 208 to identify regions in the left DLPFC or other regions of the brain that correlate with the selected ROI. In this example, regions in the left DLPFC that correlate negatively with the ROI may be identified. Though, it should be appreciated that regions in other areas of the brain, that may correlate either negatively or positively with the ROI, may be identified.

Regardless of a way in which the fMRI data has been preprocessed and after one or more ROIs, or seed regions, were selected, time courses may be extracted from fMRI images by averaging across voxels in each seed region. For seed regions with varying voxel values, such as seed maps, a weighted average may be computed. Correlation between extracted time courses may be assessed using Pearson's correlation coefficient. For statistical testing, Fisher's r-to-z transform may be used and either single group or paired t-tests may be used to determine significance (two-tailed). After the averaging and statistical testing, Fisher z values may be converted back to r values using the Fisher inverse transform. Error bars on r values may reflect the standard error of Fisher z values.

To generate functional connectivity maps, the Pearson's correlation coefficient may be computed between the seed region time courses and that of all other voxels. Fisher's r-to-z transformation may be used to convert correlation maps into z maps. Group effects may be tested with a random effects analysis using a one sample t-test. For seed-based correlation maps, a suitable threshold may be used (e.g., t=4.25 P<0.0001 uncorrected). Similarity between seed based correlation maps may be assessed using a spatial correlation coefficient across voxels (Fox et al., 2006).

It should be appreciated that the above techniques are described by way of example only, and any suitable techniques may be used to analyze fMRI data and generate functional connectivity maps, as embodiments are not limited in this respect.

In this example, the data processing, calculations, and threshold setting may be performed in volume space. For display purposes, the data may be mapped to the cortical surface using CARET and the PALS atlas (Van Essen, 2005). ROIs and integer-based overlaps may be displayed on a suitable display using average fiducial mapping option in CARET™ while functional data may be displayed using the multi-fiducial mapping option.

At block 210, coordinates for one or more target sites for application of TMS to the patient may be identified based on the functional connectivity analysis. In some embodiments, one or more regions exhibiting the anticorrelation with the ROI that is above a threshold (e.g., a peak anticorrelation) may be selected as target stimulation sites for TMS application. Thus, in one example, when the subgenual ROI is used as a seed region, a region in the left DLPFC (−44 38 34) that exhibits a peak anticorrelation may be identified as a target TMS site.

After the target sites for application of TMS are determined, process 200 may end. Though, process 200 may be repeated for the patient—for example, to monitor the efficacy of the treatment or for any other purposes.

In the example illustrated in conjunction with FIG. 2, selected ROIs comprise a single ROI. However, other types of ROIs may be selected, as embodiments are not limited in this respect.

Accordingly, in some embodiments, a seed map may be used additionally or alternatively to a single ROI. As an example, the seed map may be generated based on comparison of stimulation sites identified as effective to stimulation sites identified as ineffective for treatment of depression or other disorders. Thus, to explore differences in functional connectivity between pairs of TMS sites previously shown to differ in clinical efficacy, functional connectivity may be compared between each effective versus less effective site (Herbsman et al. 2009; Fitzgerald et al. 2009). The comparison may be performed in any suitable manner—for example, using a paired t-test and a threshold of t=3.0, P<0.005 for uncorrected images. Thus, an effective-ineffective map may be generated, with local maxima (e.g., peaks) in the map being determined using the FSL clustering algorithm. Any suitable parameters of the clustering algorithm may be used, such as, for example, threshold of t=5 (positive or negative), minimum cluster size of 2, and one peak per cluster. The threshold may be selected in any suitable manner. For example, in one embodiment, the threshold may be selected empirically, to return approximately 20-30 negative peaks and 20-30 positive peaks. Though, any other implementations may be substituted, as embodiments of the invention are not limited in this respect.

Accordingly, a map of voxels showing differences in the functional connectivity between more effective versus less effective DLPFC stimulation sites may be generated. Thus, coordinates in the left DLPFC may be identified that may serve as TMS target sites by computing seed-based functional connectivity with an a-priori ROI in the subgenual and the effective-ineffective map.

In some embodiments, a seed map may include an entire correlation map of a smaller seed region. The entire correlation map with the small subgenual ROI may be used as a large weighted ROI. In some embodiments, the weights may be the highest in the subgenual cingulate, and may also be high in the medial temporal lobes and medial prefrontal cortex. The left DLPFC may be excluded from the distributed region of interest, to avoid influencing results within the region of analysis. As an example, a target TMS site selected in this way may have coordinates of (−38 44 26).

In some embodiments, DLPFC sites exhibiting a negative correlation with the subgenual cingulate that is above a threshold may be identified as target stimulation sites for application of TMS. For example, if BA46 exhibits a negative correlation with the subgenual cingulate that is above the threshold, this area may be identified as a target stimulation site for application of TMS. Thus, anticorrelation with the subgenual cingulate may be related to antidepressant response.

In some embodiments, the ROI in the subgenual cingulate cortex may be used as a seed region so that a region in the left DLPFC that exhibits a negative correlation with the ROI may be selected as a target site for application of TMS. In some embodiments, distributed seed regions, such as ROIs in the left DLPFC, may be more reproducible than the small subgenual ROI.

It should be appreciated that embodiments are not limited to the left DLPFC as a region which activity correlates with the activity of the subgenual cingulate cortex. Thus, target stimulation sites for TMS for the treatment of depression may be identified in parietal cortex/intraparietal sulcus, anterior insula, anterior SMA, thalamus and other brain regions.

Once a target site for application of TMS to the brain of the patient is identified, the corresponding brain region may be targeted throughout the treatment (e.g., throughout successive sessions), in any suitable manner. Any suitable TMS device may be used to administer TMS to the brain of the patient to induce a desired current density to the identified target site, as embodiments are not limited in this respect. For example, the TMS device may comprise a NeuroStar TMS Therapy System from Neuronetics, Inc. Brain coordinates may be converted into measurements from the nose and ears (Andoh et al., 2009; Herbsman and Nahas, 2011). A medical practitioner may use measurements from the patient's nose and ears to place one or more coils on the target site.

Figure 3:
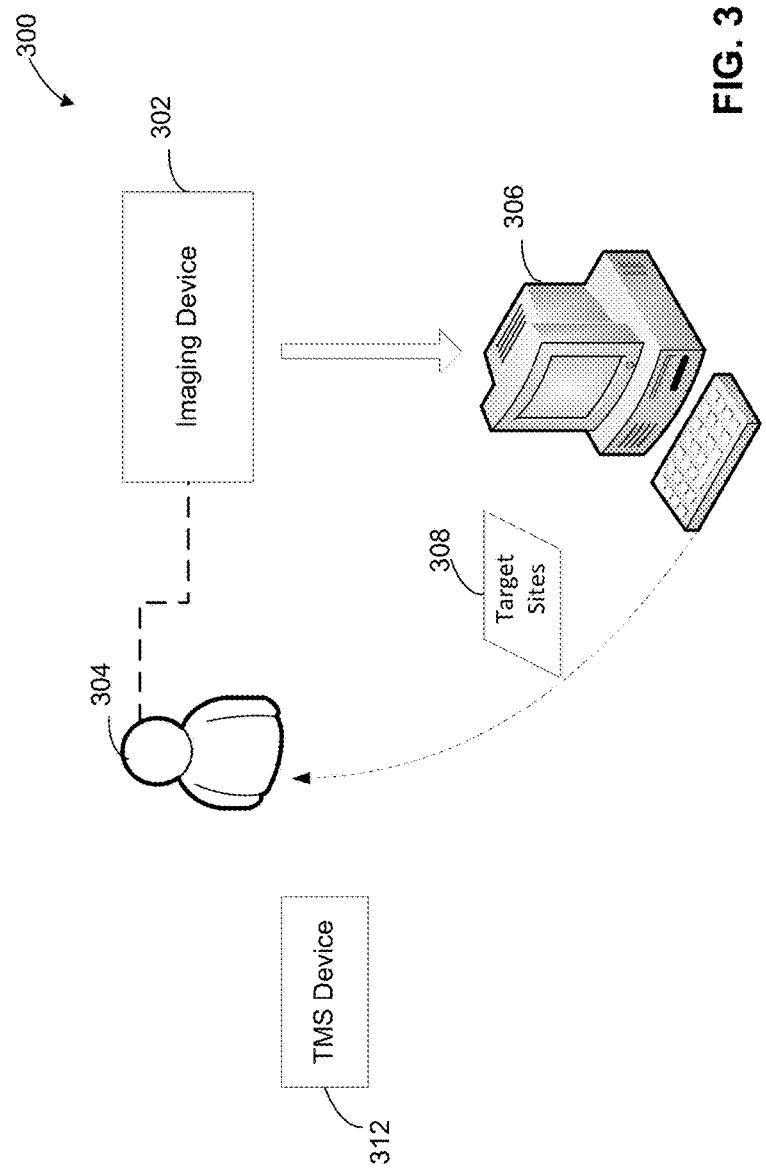
FIG. 3 illustrates generally an exemplary environment 300 in which some embodiments may be implemented.

FIG. 3 illustrates generally an exemplary environment 300 in which some embodiments may be implemented.

Environment 300 may comprise an imaging device 302, which may be any suitable MRI system. Imaging device 302 may be used to obtain structural and functional MRI data by imaging a patient 304. The functional MRI data may comprise resting state fMRI data. Though, it should be appreciated that other types of MRI data or data obtained using other suitable imaging techniques may be substituted. The MRI data acquired by imaging device 302 may be provided for processing to a computing device 306. The MRI data may be provided to computing device 306 in any suitable manner. For example, in some embodiments, the MRI data may be received by computing device 306 over a network, such as the Internet.

Computing device 306 may comprise one or more of any suitable computing devices and may comprise one or more processors, memory and any other suitable components. Computing device 306 may store in memory suitable computer-executable instructions that, when executed by the one or more processors, may implement the techniques for identifying target stimulation sites for application of TMS to a patient, in accordance with some embodiments. Computing device 306 may be associated with a suitable display which may display data resulting from processing of MRI data, and any other suitable data.

As a result of processing of fMRI data using computing device 306, one or more individual target sites 308 for application of TMS to patient 304 may be identified. The target sites may be identified using the techniques described in this application. The identified target stimulation sites may be used to position a TMS coil 310 so as to deliver TMS to the brain of patient 304. TMS coil 310 may comprise one or more TMS coils, and may be of any suitable shape and may be manufactured of any suitable material.

TMS coil 310 may be part or otherwise associated with a TMS device 312. TMS device 312 may comprise any suitable components, such as a control component, a power supply, one or more treatment coils (e.g., TMS coil 310) and other components as known in the art or developed in the future. TMS device 312 may be associated with a display.

TMS device 312 may control positioning and operation of TMS coil 310. It should be appreciated that TMS device 312 may be device of any suitable type, as embodiments are not limited in this respect. TMS device 312 may be portable or stationary, and may be operated manually, automatically, or via a combination thereof. Further, though computing device 306 and TMS device 312 are shown as separate devices, in some embodiments, these devices may be included in the same device.

Any suitable device may be used to place one or more stimulation coils at the head of the patient to induce a desired current density to the identified target stimulation site. In some embodiments, neuronavigation equipment may be used to apply TMS to the identified target site. Neuronavigation equipment may comprise a frameless stereotactic system, such as, for example, Brainsight™, which may allow targeting a specific coordinate in the patient's brain.

In some embodiments, a region of interest identified using Independent Component Analysis techniques may be utilized.

In some embodiments, the described techniques for identifying one or more target stimulation sites for application of TMS based on functional connectivity may be used to identify a size of one or more stimulation coils to stimulate the brain of a patient. A size of the coil may be selected that provides improved stimulation effect.

Further, although the described techniques involve selecting as a target TMS stimulation site a region within the left DLPFC that exhibits a negative correlation above a threshold with a region in the subgenual cingulate cortex, other approaches may be utilized. For example, the center of mass of anticorrelations within the DLPFC may be computed. Further, 3D templates of stimulation fields centered at multiple stimulation sites along the cortex may be used, and the target sites may be selected based on the voxel weightings within this field.

In some embodiments, individual stimulation sites may be identified outside the DLPFC, including stimulation sites in the parietal cortex or cerebellum.

As another modification, additionally or alternatively to fMRI, other techniques may be used for connectivity-based targeting, such as, for example, diffusion tractography. Further, brain stimulation techniques other than TMS may be used, such as transcranial direct current stimulation, focused ultrasound, deep brain stimulation, epidural electrode stimulation, etc.

Further, brain stimulation techniques other than TMS may be used, such as transcranial direct current stimulation, transcranial alternating current stimulation, focused ultrasound, transcranial photostimulation, deep brain stimulation, epidural electrode stimulation, etc. These brain stimulation techniques may be applied at one or multiple sites as guided by connectivity. In one embodiment, this may include using multiple electrodes to match the electric field induced by transcranial direct current stimulation or transcranial alternating current stimulation to the connectivity map as indicated by resting state functional connectivity MRI.

Furthermore, although the described techniques may be used to select TMS target sites for treatment of depression, the techniques may be applied to treat other brain diseases, including Parkinson's, dystonia, essential tremor, epilepsy, OCD, bipolar, pain, coma or disorders of consciousness, Alzheimer's, autism, stroke or post-stroke deficits including aphasia, hemiparesis, and neglect, and other diseases. Similar to the way the subgenual cingulate, a DBS site effective in depression, is used as a seed ROI to identify cortical targets for noninvasive brain stimulation to treat depression, DBS sites effective in other disease may be used as seed regions for connectivity analysis to identify cortical targets to treat those diseases. This includes but is not limited to the subthalamic nucleus and Parkinson's, the globus pallidus pars interna and Parkinson's or dystonia, the ventral intermediate thalamic nucleus and essential tremor, the entorhinal cortex and memory disorders including Alzheimers, the midline thalamic nucleus and disorders of consciousness, and the anterior thalamic nucleus and epilepsy. Other brain regions or networks that are not necessarily DBS sites may also be used as seed ROIs such as the anterior insula and anterior cingulate cortex in pain. Connectivity maps associated with these ROIs may be used to guide any of the noninvasive brain stimulation methods mentioned above.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. Though, a processor may be implemented using circuitry in any suitable format.

Further, it should be appreciated that a computer may be embodied in any of a number of forms, such as a rackmounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, embodiments may be embodied as a non-transitory computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present invention as discussed above. As used herein, the term "computer-readable storage medium" encompasses only a computer-readable medium that can be considered to be a manufacture (i.e., article of manufacture) or a machine. Alternatively or additionally, embodiments may be embodied as a computer readable medium other than a computer-readable storage medium, such as a propagating signal.

The terms "program" or "software" are used herein in a generic sense to refer to any type of computer code or set of computer-executable instructions that can be employed to program a computer or other processor to implement various aspects of the embodiments as discussed above. Additionally, it should be appreciated that according to one aspect of this embodiment, one or more computer programs that when executed perform methods of the embodiments need not reside on a single computer or processor, but may be distributed in a modular fashion amongst a number of different computers or processors to implement various aspects of the embodiments.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the embodiments may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, embodiments may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Some embodiments of the invention may include techniques described in Examples 1, 2, and 3, and any combination thereof. It should be appreciated that requirements recited in the following examples and applications of the various aspects pertain only to the particular embodiment being described and do not express limitations as a whole. The data, features, components and implementations in the Examples 1, 2, and 3 are mentioned merely to provide examples of the various aspects of various embodiments. However, the aspects are not limited to the descriptions in the Examples.

In addition, the intended benefits discussed in the Examples are not requirements or limitations of, but rather mention an intended effect or benefit of certain embodiments, though certain embodiments may not have the intended effect and/or benefit. In addition, any described shortcomings or stated requirements should be construed as pertaining only to a particular embodiment only, and not to the embodiments as a whole. The description and illustrations presented in the Examples 1, 2, and 3 are by way of example only.

REFERENCES

Andoh, J., et al., A triangulation-based magnetic resonance image-guided method for transcranial magnetic stimulation coil positioning. *Brain stimulation,* 2009. 2(3): p. 123-31.

Burt, T., Lisanby, S. H., and Sackeim, H. A. (2002). Neuropsychiatric applications of transcranial magnetic stimulation: a meta analysis. *Int J Neuropsychopharmacol* 5, 73-103.

Cho S S, Strafella A P (2009): rTMS of the left dorsolateral prefrontal cortex modulates dopamine release in the ipsilateral anterior cingulate cortex and orbitofrontal cortex. *PloS one.* 4:e6725.

Deco, G., V. K. Jirsa, et al. (2011). "Emerging concepts for the dynamical organization of resting-state activity in the brain." *Nat Rev Neurosci* 12(1): 43-56.

Drevets W C, Bogers W, Raichle M E (2002): Functional anatomical correlates of antidepressant drug treatment assessed using PET measures of regional glucose metabolism. *Eur Neuropsychopharmacol.* 12:527-544.

Ferreri, F., Pasqualetti, P., Maatta, S., Ponzo, D., Ferrarelli, F., Tononi, G., Mervaala, E., Miniussi, C., and Rossini, P. M. (2010). Human brain connectivity during single and paired pulse transcranial magnetic stimulation. *Neuroimage.*

Fitzgerald P B, Hoy K, McQueen S, Maller J J, Herring S, Segrave R, et al. (2009): A randomized trial of rTMS targeted with MRI based neuro-navigation in treatment-resistant depression. *Neuropsychopharmacology.* 34:1255-1262.

Fitzgerald P B, Oxley T J, Laird A R, Kulkarni J, Egan G F, Daskalakis Z J (2006): An analysis of functional neuroimaging studies of dorsolateral prefrontal cortical activity in depression. *Psychiatry research.* 148:33-45.

Fox, M. D., Snyder, A. Z., Vincent, J. L., Corbetta, M., Van Essen, D. C., and Raichle, M. E. (2005). The human brain is intrinsically organized into dynamic, anticorrelated functional networks. *PNAS* 102, 9673-9678.

Fox M D, Corbetta M, Snyder A Z, Vincent J L, Raichle M E (2006): Spontaneous neuronal activity distinguishes human dorsal and ventral attention systems. *PNAS.* 103: 10046-10051.

Fox, M. D. and M. Greicius (2010). "Clinical applications of resting state functional connectivity." *Front Syst Neurosci* 4: 19.

Fox, M. D. and M. E. Raichle (2007). "Spontaneous fluctuations in brain activity observed with functional magnetic resonance imaging." *Nat Rev Neurosci* 8(9): 700-711.

Fregni, F., and Pascual-Leone, A. (2007). Technology insight: noninvasive brain stimulation in neurology-perspectives on the therapeutic potential of rTMS and tDCS. *Nat Clin Pract Neurol* 3, 383-393.

George, M. S., L. E. Stallings, et al. (1999). "Prefrontal repetitive transcranial magnetic stimulation (rTMS) changes relative perfusion locally and remotely." *Human Psychopharmacology: Clinical and Experimental* 14: 161-170.

George, M. S., E. M. Wassermann, et al. (1996). "Changes in mood and hormone levels after rapid-rate transcranial magnetic stimulation (rTMS) of the prefrontal cortex." *J Neuropsychiatry Clin Neurosci* 8(2): 172-180.

George, M. S., Wassermann, E. M., Kimbrell, T. A., Little, J. T., Williams, W. E., Danielson, A. L., Greenberg, B. D., Hallett, M., and Post, R. M. (1997). Mood improvement following daily left prefrontal repetitive transcranial magnetic stimulation in patients with depression: a placebo-controlled crossover trial. *The American journal of psychiatry* 154, 1752-1756.

Hallett, M. (2007). Transcranial magnetic stimulation: a primer. *Neuron* 55, 187-199.

Herbsman, T., D. Avery, et al. (2009). "More lateral and anterior prefrontal coil location is associated with better repetitive transcranial magnetic stimulation antidepressant response." *Biol Psychiatry* 66(5): 509-515.

Herbsman, T. and Z. Nahas, Anatomically based targeting of prefrontal cortex for rTMS. Brain stimulation, 2011. 4(4): p. 300-2.

Herwig, U., F. Padberg, et al. (2001). "Transcranial magnetic stimulation in therapy studies: examination of the reliability of "standard" coil positioning by neuronavigation." *Biol Psychiatry* 50(1): 58-61.

Herwig, U., Satrapi, P., and Schonfeldt-Lecuona, C. (2003): Using the international 10-20 EEG system for positioning of transcranial magnetic stimulation. *Brain Topogr* 16, 95-99.

Kito S, Fujita K, Koga Y (2008): Regional cerebral blood flow changes after low-frequency transcranial magnetic stimulation of the right dorsolateral prefrontal cortex in treatment-resistant depression. *Neuropsychobiology.* 58:29-36.

Kito S, Hasegawa T, Koga Y (2011): Neuroanatomical correlates of therapeutic efficacy of low-frequency right prefrontal transcranial magnetic stimulation in treatment-resistant depression. *Psychiatry Clin Neurosci.* 65:175-182.

Koenigs M, Grafman J (2009): The functional neuroanatomy of depression: distinct roles for ventromedial and dorsolateral prefrontal cortex. *Behavioural brain research.* 201:239-243.

Lisanby, S. H., and Belmaker, R. H. (2000): Animal models of the mechanisms of action of repetitive transcranial magnetic stimulation (RTMS): comparisons with electroconvulsive shock (ECS). *Depress Anxiety* 12, 178-187.

Mayberg H S, Brannan S K, Tekell J L, Silva J A, Mahurin R K, McGinnis S, et al. (2000): Regional metabolic effects of fluoxetine in major depression: serial changes and relationship to clinical response. *Biol Psychiatry.* 48:830-843.

Mayberg H S, Lozano A M, Voon V, McNeely H E, Seminowicz D, Hamani C, et al. (2005): Deep brain stimulation for treatment-resistant depression. *Neuron.* 45:651-660.

Mayberg H S (2007): Defining the neural circuitry of depression: toward a new nosology with therapeutic implications. *Biol Psychiatry.* 61:729-730.

Nahas Z, Teneback C, Chae J H, Mu Q, Molnar C, Kozel F A, et al. (2007): Serial vagus nerve stimulation functional MRI in treatment-resistant depression. *Neuropsychopharmacology.* 32:1649-1660.

Padberg, F. and M. S. George (2009). "Repetitive transcranial magnetic stimulation of the prefrontal cortex in depression." *Exp Neurol* 219(1): 2-13.

Paillère Martinot M-L, Galinowski A, Ringuenet D, Gallarda T, Lefaucheur J-P, Bellivier F, et al. (2010): Influence of prefrontal target region on the efficacy of repetitive transcranial magnetic stimulation in patients with medication-resistant depression: a [(18)F]-fluorodeoxyglucose PET and MRI study. *The international journal of neuropsychop-* harmacology/official scientific journal of the Collegium Internationale Neuropsychopharmacologicum (CINP). 13:45-59.

Paus T, Castro-Alamancos Ma, Petrides M (2001): Cortico-cortical connectivity of the human mid-dorsolateral frontal cortex and its modulation by repetitive transcranial magnetic stimulation. European Journal of Neuroscience. 14:1405-1411.

Rajkowska G, Goldman-Rakic P S (1995): Cytoarchitectonic definition of prefrontal areas in the normal human cortex: II. Variability in locations of areas 9 and 46 and relationship to the Talairach Coordinate System. Cereb Cortex. 5:323-337.

Ruff, C. C., Driver, J., and Bestmann, S. (2009). Combining TMS and fMRI: from 'virtual lesions' to functional-network accounts of cognition. Cortex 45, 1043-1049.

Rusjan P M, Barr M S, Farzan F, Arenovich T, Maller J J, Fitzgerald P B, et al. (2010): Optimal transcranial magnetic stimulation coil placement for targeting the dorsolateral prefrontal cortex using novel magnetic resonance image-guided neuronavigation. Human brain mapping. 31:1643-1652.

Siebner, H. R., Bergmann, T. O., Bestmann, S., Massimini, M., Johansen-Berg, H., Mochizuki, H., Bohning, D. E., Boorman, E. D., Groppa, S., Miniussi, C., et al. (2009). Consensus paper: combining transcranial stimulation with neuroimaging. Brain Stimul 2, 58-80.

Talairach J, and Tournoux P (1988): Co-Planar Stereotaxic Atlas of the Human Brain. New York: Thieme Medical Publishers, Inc.

van den Heuvel, M. P. and H. E. Hulshoff Pol (2010). "Exploring the brain network: a review on resting-state fMRI functional connectivity." Eur Neuropsychopharmacol 20(8): 519-534.

van der Kouwe, A. J., Benner, T., Salat, D. H., and Fischl, B. (2008). Brain morphometry with multiecho MPRAGE. NeuroImage 40, 559-569.

Van Dijk, K. R., Hedden, T., Venkataraman, A., Evans, K. C., Lazar, S. W., and Buckner, R. L. (2010). Intrinsic functional connectivity as a tool for human connectomics: theory, properties, and optimization. Journal of neurophysiology 103, 297-321.

Van Essen D C (2005): A population-average, landmark- and surface-based (PALS) atlas of human cerebral cortex. Neuroimage. 28:635-662.

Wu J, Buchsbaum M S, Gillin J C, Tang C, Cadwell S, Wiegand M, et al. (1999): Prediction of antidepressant effects of sleep deprivation by metabolic rates in the ventral anterior cingulate and medial prefrontal cortex. Am J Psychiatry. 156:1149-1158.

EXAMPLE 1

Abstract:

Transcranial magnetic stimulation (TMS) to the left dorsolateral prefrontal cortex (DLPFC) is used clinically for the treatment of depression however outcomes vary greatly between patients. The average clinical efficacy of different left DLPFC TMS sites is related to intrinsic functional connectivity with remote regions including the subgenual cingulate. Further, we suggested that functional connectivity with these remote regions might be used to identify optimized left DLPFC TMS targets. However it remains unclear if and how this connectivity-based targeting approach should be applied to individualize therapy to specific patients. In this example we show that individual differences in DLPFC connectivity are large, reproducible across sessions, and can be used to generate individualized DLPFC TMS targets superior to those selected on the basis of group-average connectivity. Factors that may improve individualized targeting including the use of seed maps and the focality of stimulation are investigated and discussed. The techniques presented here applicable to individualized targeting of focal brain stimulation across a range of diseases and stimulation modalities.

Introduction:

Repetitive transcranial magnetic stimulation (rTMS) is a non-invasive brain stimulation technique that is showing utility in the treatment of a variety of neurological and psychiatric disorders (Burt et al., 2002; Fregni and Pascual-Leone, 2007; Hallett, 2007). Its most common use and only FDA approved therapeutic indication is excitatory stimulation to the left dorsal-lateral prefrontal cortex (DLPFC) for the treatment of medication-resistant depression (George et al., 1995; O'Reardon et al., 2007; Padberg and George, 2009; Pascual-Leone et al., 1996). Despite repeated trials demonstrating a statistically significant antidepressant effect, the clinical utility of rTMS has been limited by large heterogeneity in clinical response.

One factor known to contribute to this response heterogeneity is differences in the site of stimulation in the DLPFC (Ahdab et al., 2010; Fitzgerald et al., 2009; Herbsman et al., 2009; Herwig et al., 2001; Padberg and George, 2009). The targeting technique routinely employed in clinical practice is to center the TIVIS coil at a point 5 cm anterior to the motor cortex measured along the curvature of the scalp. This approach identifies different stimulation sites in different subjects (Ahdab et al., 2010; Herwig et al., 2001) and some sites appear to be more effective than others at producing an antidepressant response (Fitzgerald et al., 2009; Herbsman et al., 2009; Padberg and George, 2009; Paillere Martinot et al., 2010). In an effort to understand why some sites are more effective, we used intrinsic (resting state) fMRI to identify differences in functional connectivity between effective and less effective DLPFC stimulation sites at the population level (Fox et al., 2012a). Significant differences in connectivity were seen in a variety of cortical and limbic regions including the subgenual cingulate, a region repeatedly implicated in antidepressant response (Drevets et al., 2008; Mayberg, 2009; Mayberg et al., 2005). Specifically, more effective DLPFC TMS sites showed a stronger negative correlation (anticorrelation) with the subgenual. Based on these findings, we proposed a connectivity-based targeting strategy for TMS and used this technique to identify theoretically optimal TMS target coordinates in the left DLPFC at the population level (Fox et al., 2012a).

An important advantage of this connectivity-based targeting strategy is that it can be scaled from the population level down to the level of single subjects to tailor treatment to individual patients. The DLPFC varies greatly between individuals on a histological basis (Rajkowska and Goldman-Rakic, 1995) thus the population-average TMS coordinates might be suboptimal for many patients. However individualized targeting will be associated with an inherent worsening of signal to noise that could overwhelm any benefit of accounting for individual differences. For example, targeting a population-average focus of hypometabolism in the left DLPFC with TMS appears superior to the standard 5 cm technique (Fitzgerald et al., 2009), however three separate studies targeting individualized foci of hypometabolism failed to provide clinical benefit (Garcia-Toro et al., 2006; Herwig et al., 2003a; Paillere Martinot et al., 2010). In fMRI, the subgenual is a region with poor signal to noise (Ojemann et al., 1997) and intrinsic anticorrelations seem to be less reproducible than positive correlations (Shehzad et al., 2009). It therefore remains unclear if connectivity based targeting can or should be used to identify individualized TMS sites in the DLPFC for the treatment of depression.

In this example we show that individual differences in DLPFC connectivity are large, reproducible across scanning sessions, and can be translated into individualized TMS targets on the cortical surface. Further, we identify factors that improve the reproducibility of individualized targeting such as the use of seed maps and the focality of stimulation.

Methods:

Subjects and Data Collection:

This study utilized two independent datasets:

1) The first dataset was used for some initial analyses on individual differences and as an independent cohort to construct seed maps. This dataset consisted of 98 healthy right-handed subjects (48 male, ages 22±3.2 years (mean±SD)) collected in Boston, Mass. This was a subset of subjects previously used in an analysis of resting state functional connectivity (Yeo et al., 2011) and the cohort used in our recent experiment (Fox et al., 2012a). Experiments were conducted with the written consent of each subject and approved by the Partners' Institutional Review Board. Imaging was performed on a 3 T Siemens whole body MRI System with a phased array head coil. Each subject completed two 6.2 min long (124 frames) resting state fMRI scans (TR=3000 ms, TE=30 ms, FA=85°, 3×3×3 mm voxels, FOV=216, 47 axial slices with interleaved acquisition and no gap). During scanning, participants were instructed to keep their eyes open and remain still. All subjects were originally enrolled in an fMRI study on cognitive tasks; the resting state data used in this study was collected at the beginning of each subject's scan before any tasks were performed. Structural data included a high-resolution multi-echo T1-weighted magnetization-prepared gradient-echo image (TR=2200 ms, TI=1100 ms, TE=1.54 ms for image 1 to 7.01 ms for image 4, FA=7°, 1.2×1.2×1.2 mm voxels, FOV=230) (van der Kouwe et al., 2008).

2) The second dataset was used to assess reproducibility of individual differences across different scanning sessions. This dataset consisted of 42 healthy right-handed subjects (16 male, ages 20±2.0 years (mean±SD)) scanned during two different MRI sessions separated by 68±54 days (mean±SD), range 2230 days. This dataset is a subset of subjects that have been previously used in an analysis of resting state functional connectivity (Yeo et al., 2011) and has been previously used to examine the reproducibility of subject head motion (Van Dijk et al., 2012). Scan parameters were identical to the above with the exception that all subjects completed two scanning sessions on two separate days.

A Priori Defined Regions of Interest:

Two regions of interest (ROI) were defined a priori for use in the present analysis including one region in the subgenual cingulate cortex and one large ROI in the left DLPFC. The ROI in the subgenual cingulate cortex was taken from a recent intrinsic connectivity study from our lab (Fox et al., 2012a). Briefly, we identified coordinates from prior studies where a reduction in subgenual activity was associated with antidepressant response across a wide range of treatment modalities (Drevets et al., 2002; Kito et al., 2008; Kito et al., 2011; Mayberg et al., 2000; Mayberg et al., 2005; Nahas et al., 2007; Wu et al., 1999) (see Table 1 in Fox et al 2012). We converted reported subgenual coordinates (generally in Talairach space) into MNI space using tal2mni (http://imaging.inrc-cbu.cam.ac.tik/imaging/MniTalairach). For the purposes of the current study, "Talairach" refers to the atlas coordinate space as defined by Talairach and Tournoux in 1988 (Talairach and Tournoux, [988]). After conversion to MNI space, coordinates were averaged across studies (6, 16, −10). We created a 10 mm sphere centered on these coordinates and masked this ROI to exclude voxels not sampled in any of our 98 subjects or voxels falling outside of the cerebral cortex using the HarvardOxford cortical regions template available in FSL.

We also wanted to construct a large ROI covering the full range of possible stimulation targets in the left DLPFC. To do this, we first identified three important DLPFC coordinates upon which to center our ROI. The first coordinate was the average TMS target used most clinical trials identified using the 5 cm method. Since multiple studies reported the average coordinates resulting from the 5 cm targeting method (Herbsman et al., 2009; Herwig et al., 2001), these coordinates were averaged to create one set of coordinates best representing the standard 5 cm target site. To generate coordinates for Brodmann regions (BA9 and 46) the average y and z Talairach coordinates were taken from Rajkowska and Goldman-Rakic 1995 (Rajkowska and Goldman-Rakic, 1995). However this paper did not report x coordinates so this was determined from the coordinate in Talairach space on the cortical surface constrained by the y and z coordinates (Talairach and Tournoux, 1988). This complete set of Talairach coordinates was then transformed into MNI space. 25 mm radius spheres were generated centered on each of these DLPFC coordinates in MNI space. This sphere size was chosen to fully cover what is generally considered the DLPFC without extending into adjacent areas (i.e. insula or medial prefrontalcortex.) All spheres were then masked to eliminate any unsampled voxels or voxels lying outside of grey matter as defined by the standard Harvard/Oxford grey matter template in FSL thresholded at an intensity of 70. The three spheres were then combined to create a single large mask of the left DLPFC.

Data Processing:

FMRI data were processed in accordance with the strategy of Fox et al 2005 (Fox et al., 2005) as implemented in Van Dijk 2010 (Van Dijk et al., 2010). In brief, functional data were preprocessed to decrease image artifacts and between-slice timing differences. Data were then spatially smoothed using a Gaussian kernel of 6 mm full-width at half-maximum and temporally filtered (0.009 Hz<f<0.08 Hz). Next, several spurious or nonspecific sources of variance were removed by regression of the following variables: (1) six movement parameters computed by rigid body translation and rotation during preprocessing, (2) mean whole brain signal, (3) mean brain signal within the lateral ventricles, and (4) the mean signal within a deep white matter ROI. Inclusion of the first temporal derivatives of these regressors within the linear model accounted for the time-shifted versions of spurious variance.

Three "seed regions" were used in the present functional connectivity analysis, all taken from a prior study of DLPF functional connectivity and generated using an independent cohort of 98 normal subjects (Fox et al submitted). The first seed region was simply the small subgenual ROI as defined above (Subgenual ROI). The second seed was the entire subgenual functional connectivity map previously generated using random effects analysis across 98 subjects (SG-based seed map). The third seed was the entire functional connectivity map of effective versus ineffective DLPF stimulation sites, previously generated using a paired test across 98 normal subjects (Efficacy-based seed map). The later two "seed regions" cover the entire brain with the exception of the left DLPFC which was omitted to avoid biasing of results in this region. Note that each voxel in these later two seed regions has a different weight. Time courses were extracted from each seed region by computing a weighted average of all non-zero voxels within each seed. The Pearson's correlation coefficient was computed between this extracted time course and that of all other voxels. Fisher's r-to-z transformation was used to convert correlation maps into z maps.

To determine the similarity between two functional connectivity maps, a spatial correlation coefficient was computed across voxels (Fox et al., 2006). To normalize the distributions for statistical comparison, spatial correlation values were converted using Fisher r to z transform. These values are listed in the text as z(r). Although intuitive, the spatial correlation coefficient may miss some differences when comparing two maps (i.e scalar offsets or differences in magnitude) so we also compared maps using a spatial eta coefficient (Cohen et al., 2008).

Figure 11:
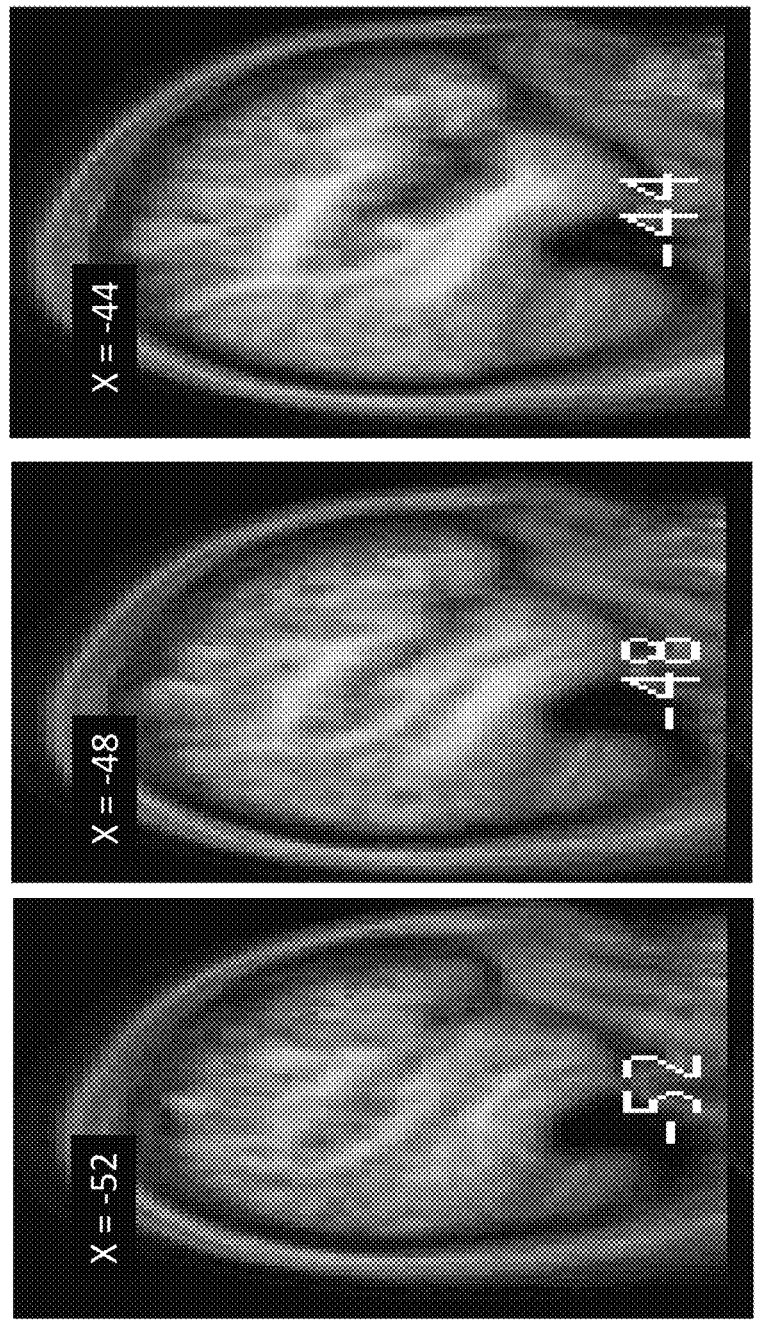
FIG. 11 illustrates brain slices showing some of the 163 nodes across the cortical surface of the left DLPFC used to generate potential TMS targets. Nodes are separated from other nodes by 3 mm in all directions.

To create a set of potential TMS target sites, we created 163 potential stimulation nodes across the surface of the left DLPFC separated from each other by—3 mm in all directions (FIG. 11). We centered spheres at each of these nodes of varying radiuses to reflect varying focality of different TMS coils (masked to exclude voxels outside the brain). For each subject, we used one session to identify the optimal node (most anticorrelated with each seed) then obtained the average value within the ROI at this node from the other session. Results were compared to those obtainable with population-based targeting, i.e. targeting the same node in all subjects selected using the group map from the independent 98 subject dataset.

All data processing, calculations, and thresholding were performed in volume space. For display purposes data were mapped to the cortical surface using CARET and the PALS atlas (Van Essen, 2005) using the average fiducial mapping option.

Results:

Functional connectivity was computed with three seed regions/seed maps to identify candidate TMS targets in the left DLPFC (FIG. 4). Regardless of whether one used the small subgenual seed region (FIG. 4A), the full subgenual-based seed map (FIG. 4B), or the efficacy-based seed map (FIG. 4C), a clear anticorrelated node was identified at the group level (black arrows). However, when examining results from single subjects, pronounced heterogeneity was apparent. The ideal group-level stimulation target may suffice for Subject 1, but is far from the ideal target for Subject 2.

Figure 9:
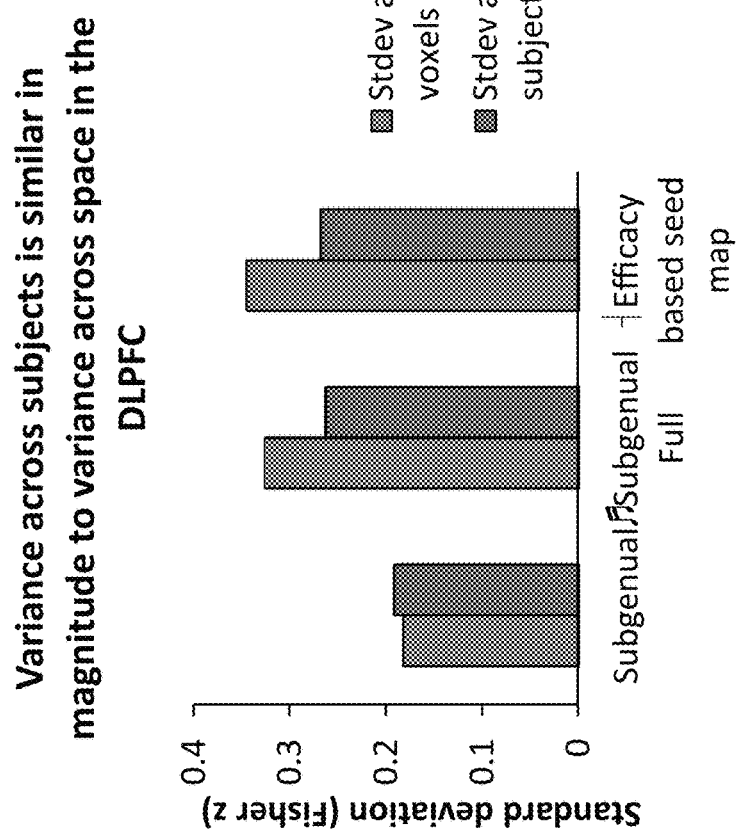
FIG. 9 illustrates variability in connectivity across subjects is similar in magnitude to variability in connectivity across space in the dorsal lateral prefrontal cortex (DLPFC). Shown is the standard deviation across subjects for all voxels in the left DLPFC (individual variability, blue) compared to the standard deviation across voxels for all subjects (spatial variability, red) for the three seed regions/seed maps considered in the present article.

To obtain an estimate of the magnitude of these individual differences in functional connectivity, the standard deviation across subjects for every voxel in the left DLPFC was computed (FIG. 9). For reference, this variance was compared to the standard deviation across space (i.e. individual DLPFC voxels) within a subject. For the subgenual seed region, the variability across subjects was actually slightly larger than the variability across space within the DLPFC (0.192 vs 0.183 z(r)). Averaged across all three seed regions/maps, the variability across subjects was 0.241 while the variability across space was 0.285 z(r). This suggests that individual differences in DLPFC connectivity are of similar magnitude to spatial differences in connectivity within the DLPFC.

Figures 5A, 5B, 5C:
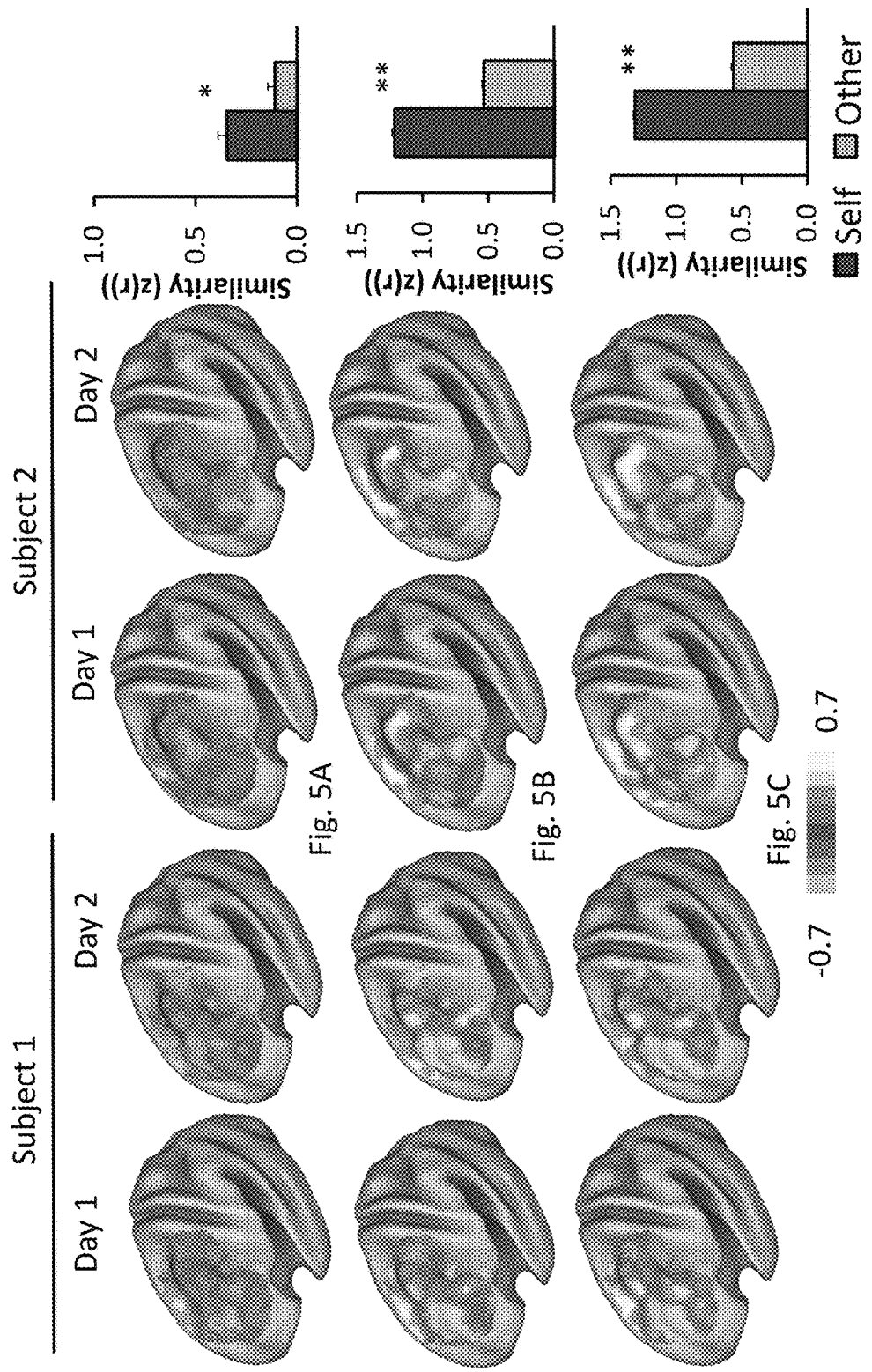
FIGS. 5A-5C illustrate individual differences in dorsal lateral prefrontal cortex (DLPFC) connectivity are reproducible across scanning sessions. Resting state functional connectivity maps are shown for two subjects (subject 1, 2) scanned on two separate days (day 1, 2) using a seed region in the subgenual cingulate (FIG. 5A) a subgenual-based seed map (FIG. 5B) and an efficacy-based seed map (FIG. 5C). Bar graphs show the similarity (spatial correlation) between maps from the same subject across different days (self) compared to the similarity between maps from different subjects (other). * $P<10^{-4}$, ** $P<10^{-17}$.

To determine if these individual differences were reproducible across time, DLPFC connectivity with the three seed regions/seed maps was computed in 42 subjects scanned on two separate days (FIGS. 5A-5C). The similarity (spatial correlation) between DLPFC connectivity maps from the same subject on two separate days was compared to the similarity between maps from different subjects. All three seed regions/maps showed significantly more consistency within a subject than between subjects including the subgenual seed region (z(r)=0.345 vs 0.11 $P<10^{-4}$), subgenual-based seed map (z(r)=1.22 vs 0.537, $P<10^{-17}$) and efficacy-based seed map (z(r)=1.32 vs 0.567, $P<10^{-21}$). DLPFC connectivity also remained reproducible within a subject even when comparing across our three different seed regions. Specifically, DLPFC connectivity within a subject with different seeds (and different sessions) was more similar than the same seed across different subjects (z(r)=0.618 versus 0.396, $P<10^{-6}$).

Importantly, not all seed regions performed equally well. Both the subgenual-based and efficacy-based seed-maps were significantly more reproducible across days than the smaller subgenual seed region ($P<10^{-16}$). In fact, connectivity with the subgenual-based seed map was a better predictor of connectivity with the small subgenual seed region on a separate day than connectivity with the subgenual seed region itself (z(r)=0.426 vs 0.345, $P<0.05$). This result held true even when the subgenual and the majority of the ventral medial prefrontal was excluded from the subgenual-based seed map (FIGS. 10A-10C).

Figure 6:
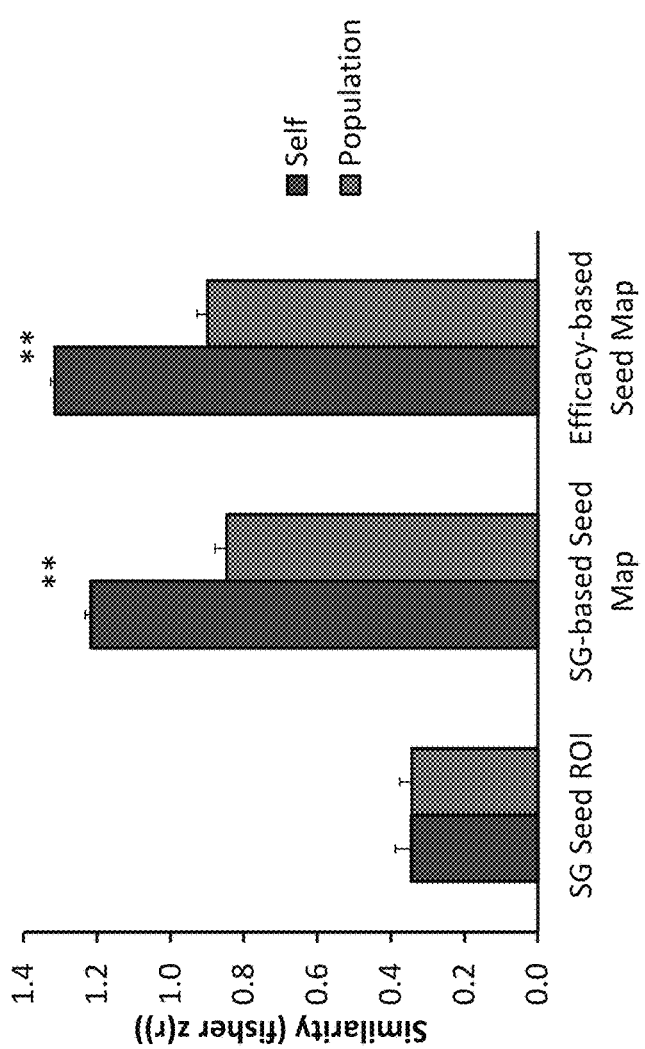
FIG. 6 illustrates similarity of single-subject maps compared to group maps. The spatial correlation coefficient is shown between maps from the same subject across different days (self) compared to the spatial correlation between single subject maps and that of the population (group) for the three seed regions/seed maps considered in the present article. ** $P<10-12$.

The above results attest to reproducibility of individual differences and indicate that subjects are more similar to themselves scanned on a different day than they are to other subjects. However, no one would propose targeting TMS in one subject based on connectivity results from another subject. A more pertinent comparison for determining the best way to target TMS is to compare single subject maps to that of the population (FIG. 6). Subjects were more similar to themselves scanned on a different day than they were to the population map for the subgenual-based seed map (z(r)= 1.22 vs 0.846, $P<10^{-13}$) and efficacy-based seed map (z(r)= 1.32 vs 0.898, $P<10^{-12}$) but not for the small subgenual seed region (z(r)=0.345 vs 0.344, $P>0.9$).

Finally, it is important to determine if these individual differences in DLPFC connectivity can actually be translated into individualized TMS targets. Since TMS is constrained to the cortical surface, 163 potential surface nodes were created that should be accessible by TMS (FIG. 11). Spheres of different sizes were centered on these various surface nodes to reflect differences in the focality of potential TMS coils. The ideal stimulation target (i.e. node with the strongest anticorrelation) was selected based on either individualized functional connectivity results from day one or the population map. These TMS targets were then "tested" on the functional connectivity results from day 2 by computing the average voxel value within each target. In this way individualized targeting can be directly compared to population-based targeting, with the superior target being the one overlying the strongest anticorrelation. As an example, we show selection of optimal TMS targets for one subject based on functional connectivity with the subgenual-based seed map for stimulation fields of radius 6 mm and 20 mm (FIGS. 7A-7C). For this subject, individualized targeting was superior to population-based targeting for both stimulation field sizes, although results were more pronounced for the 6 mm sphere compared to the 20 mm sphere.

Similar analyses were conducted for all subjects using our three possible seed regions/maps with stimulation fields ranging from 1 mm radius to 30 mm radius (FIGS. 8A-8C). Averaging across all stimulation field sizes, there was a significant advantage of individualized over population-based targeting for the small subgenual ROI ($P<0.007$) the subgenual-based seed map ($P<10^{-4}$) and the efficacy-based seed map ($P<10^{-8}$). For all three seed regions/maps, the smaller the stimulation field the greater the advantage of individualized targeting over population-based targeting. As expected based on the spatial correlation results, the two seed maps showed a greater advantage of individualized targeting overall compared to the smaller and noisier subgenual ROI.

Discussion:

There are several novel results in this example important for successful individualized targeting of TMS to the DLPFC based on functional connectivity. First, individual differences in DLPFC connectivity are large and reproducible across sessions. Second, TMS targets can be selected based on these individual differences and are generally superior to targets selected on the basis of a group map. Finally, individualized targeting might be improved through the use of a seed map over a seed region and with more focal stimulation coils.

Individualized Targeting of TMS

The idea that one should target therapeutic TMS in depression based on individual differences in anatomy or function is not new. Further, it is widely recognized that the conventional 5 cm targeting technique is insufficient (Ahdab et al., 2010; Fitzgerald et al., 2009; Herbsman et al., 2009; Herwig et al., 2001; Padberg and George, 2009). Methods to account for individual differences in anatomy have been proposed including targeting based on standardized EEG electrode positions (Herwig et al., 2003b), or specific MRI coordinates (Fitzgerald et al., 2009; Herbsman et al., 2009; Rusjan et al., 2010). A randomized trial targeting coordinates chosen based on group-level DLPFC hypometabolism failed to reach its primary endpoint but did show some clinical benefit beyond the 5 cm approach (Fitzgerald et al., 2009). Taking this approach a step further, three trials have targeted TMS based on individualized hypometabolic foci indentified with either SPECT (Garcia-Toro et al., 2006) or PET (Herwig et al., 2003a; Paillere Martinot et al., 2010). All three trials failed to show benefit beyond the conventional 5 cm approach. A question relevant to the present investigation is why targeting a group-average focus of hypometabolism would be successful while targeting individualized foci would fail. Many explanations are possible, but two will be considered here. First, hypometabolic foci may not be the ideal target for TMS, and perhaps some other property of the DLPFC is responsible for antidepressant response (such as connectivity to deep limbic regions). Given the anticorrelation between limbic regions and the DLPFC even in normal subjects, DLPFC hypometabolism could be secondary to limbic hyperactivity rather than causal in the disease process (Fox et al., 2012a). Second, individual PET maps may simply be too noisy to serve as a basis for individualized targeting of TMS, and one is better off targeting a population-average focus. Critically, none of these prior trials of individualized targeting was preceded by an analysis of the reproducibility of individualized hypometabolic foci or an investigation into techniques that might optimize their identification. This prior work serves as an important example of the challenges of translating a technique from application at the population level to clinical utility in individual subjects. Further, it highlights the importance of methodological studies such as the present work for technique validation and optimization prior to embarking on a clinical trial.

Individual Differences in Resting State Functional Connectivity MRI

Intrinsic (resting state) functional connectivity MRI is a powerful imaging technique that utilizes correlations in spontaneous fluctuations in the blood oxygenation level-dependent (BOLD) signal to assess functional relationships between regions (Biswal et al., 1995; Fox and Raichle, 2007; Van Dijk et al., 2010). This technique has several theoretical and practical advantages for clinical translation (Fox and Greicius, 2010). Accumulating evidence suggests that individual differences in intrinsic connectivity are behaviorally relevant (Baldassarre et al., 2012; Hampson et al., 2006; Koyama et al., 2011; Seeley et al., 2007; van den Heuvel et al., 2009; Zhu et al., 2011) and to some extent reproducible across scanning sessions (Braun et al., 2012; Cohen et al., 2008; Mannfolk et al., 2011; Mcindl et al., 2010; Shehzad et al., 2009; Van Dijk et al., 2010; Wang et al., 2011; Zuo et al., 2010). Recently we found that across the cortex, some of the largest individual differences in functional connectivity localize to the left DLPFC (Mueller et al., 2012), complementing known histological variability in this region (Rajkowska and Goldman-Rakic, 1995) and highlighting the potential for individualized targeting.

Only a few prior studies have used intrinsic connectivity to identify individualized TMS targets (Eldaief et al., 2011; Hoffman et al., 2007) (for review see (Fox et al., 2012b)). No study has focused on identification of individualized targets in the DLPFC, designed a systematized approach for TMS target selection, examined the reproducibility of these targets, or investigated factors to improve individualized targeting. These are all novel contributions of the present investigation and are critical steps towards making individualized connectivity-based guidance of TMS useful.

Using Seed Maps to Improve Signal to Noise

A potentially important methodological development presented here is the use of weighted seed maps rather than small seed regions to improve signal to noise in single-subject connectivity analyses. If one is attempting to identify a node in the DLPFC anticorrelated with the subgenual in a specific subject, the optimal approach is not to simply perform functional connectivity with the subgenual. Rather, more reproducible results are obtained by first computing functional connectivity with the subgenual on a large independent cohort to generate a seed map. One can then subtract the area of interest from the seed map (in this case the DLPFC) then use the seed map rather than the small subgenual seed region to assess functional connectivity in the single subject. Somewhat counter-intuitively, the result is a better prediction of subgenual connectivity than would be obtained using the subgenual seed region itself. This approach even works when the subgenual and surrounding medial prefrontal cortex is removed from the seed map, an important finding given the variability with which different scanners and MRI sequences sample this area of high susceptibility (Ojemann et al., 1997). Further work is needed to determine if this approach will be useful in other instances where single-subject functional connectivity with a small or noisy seed region is desired.

Impact of Stimulation Field Size

Another important finding from the current article is the effect of stimulation field size on the benefits of individualized versus population-based targeting. The smaller the field size, the more important individualized targeting becomes. This factor could become critical for more invasive and potentially focal DLPFC stimulation techniques such as epidural or subdural stimulation (Kopell et al., 2011). Conversely, individualized targeting becomes less important with larger stimulation field sizes. The FDA approved Neuroneticsk' Neurostar protocol uses a coil with a relatively large stimulation field (~5×6 cm). This large coil size may be part of the reason that trials have produced statistically significant results at the population level despite the lack of individualized targeting and the inaccuracies inherent in the 5 cm technique.

An important question raised by the current analysis is the ideal size of the TMS coil and stimulation field. Much of this answer will depend on whether stimulation of multiple voxels results in an average or an additive effect. If stimulation of multiple voxels is additive, there may be advantages to using a larger coil and stimulating more voxels. However if the effect is averaged, then a more focal coil directly targeting the peak anticorrelated node will likely be superior. Note that this assumes that both coils stimulate with equal peak intensity (such as 100% of motor threshold) as suggested by current safety guidelines (Rossi et al., 2009). Another critical question raised by the current results is the relative safety of TMS at different field sizes. Can one stimulate at double the intensity if one is only stimulating the number of voxels? If so, the advantages of more focal field sizes and therefore individualized targeting become more prominent.

Future Work

First, these results strongly support the utility of individualized targeting of TMS based on connectivity, and the clinical validity of this approach. Second, this example tested reproducibility in a cohort of normal subjects, not patients with depression. However, given that connectivity-based targeting identifies similar DLPFC TMS targets in patients with depression (Fox et al., 2012a), we expect our results to be relevant to this population. Third, this example was focused specifically on left DLPFC targets for depression. The reproducibility of individualized targets in other cortical regions or with alternate deep nuclei can also be validated. Finally, the ideal size of the stimulation field, an issue relevant to understanding the magnitude of benefit one might achieve through individualized targeting can be explored. Stimulation across multiple voxels can be tested to see if it results in an additive or average effect and the relative safety of increasing stimulation intensity in small versus large stimulation fields.

Conclusions:

There is significant individual variability in the connectivity of the DLPFC. This variability is stable across scanning sessions and can be used to generate individualized and reproducible TMS targets. Seed maps demonstrate more stability than a small subgenual seed region and may be an effective technique for improving signal to noise in single subject functional connectivity analyses. Finally, the more focal the stimulation field, the greater the benefit likely to come from individualized targeting. The methods presented here show the utility of individualized connectivity-based targeting of left DLPFC TMS for depression. Further, these techniques might be applicable to identification of individualized targets for focal brain stimulation across a variety of disorders and stimulation techniques.

Figures:

FIG. 4: Identification of connectivity-based TMS targets in the left dorsal lateral prefrontal cortex (DLPFC) at the group and single subject level. Resting state functional connectivity maps are shown for the population (group) and two individual subjects (subject 1, 2) for a seed region in the subgenual cingulate (FIG. 4A) a seed map based on subgenual connectivity (FIG. 4B) and a seed map based on connectivity differences between effective and ineffective DLPFC TMS sites (FIG. 4C). Surface-based maps are masked to show only voxels in the left DLPFC. Black arrows identify a potential stimulation site at the group level that is different between subjects 1 and 2.

FIG. 5: Individual differences in dorsal lateral prefrontal cortex (DLPFC) connectivity are reproducible across scanning sessions. Resting state functional connectivity maps are shown for two subjects (subject 1, 2) scanned on two separate days (day 1, 2) using a seed region in the subgenual cingulate (FIG. 5A) a subgenual-based seed map (FIG. 5B) and an efficacy-based seed map (FIG. 5C). Bar graphs show the similarity (spatial correlation) between maps from the same subject across different days (self) compared to the similarity between maps from different subjects (other). * $P<10^{-4}$, ** $P<10^{-17}$.

FIG. 6: Similarity of single-subject maps compared to group maps. The spatial correlation coefficient is shown between maps from the same subject across different days (self) compared to the spatial correlation between single subject maps and that of the population (group) for the three seed regions/seed maps considered in the present article. ** $P<10$-12.

Figure 7:
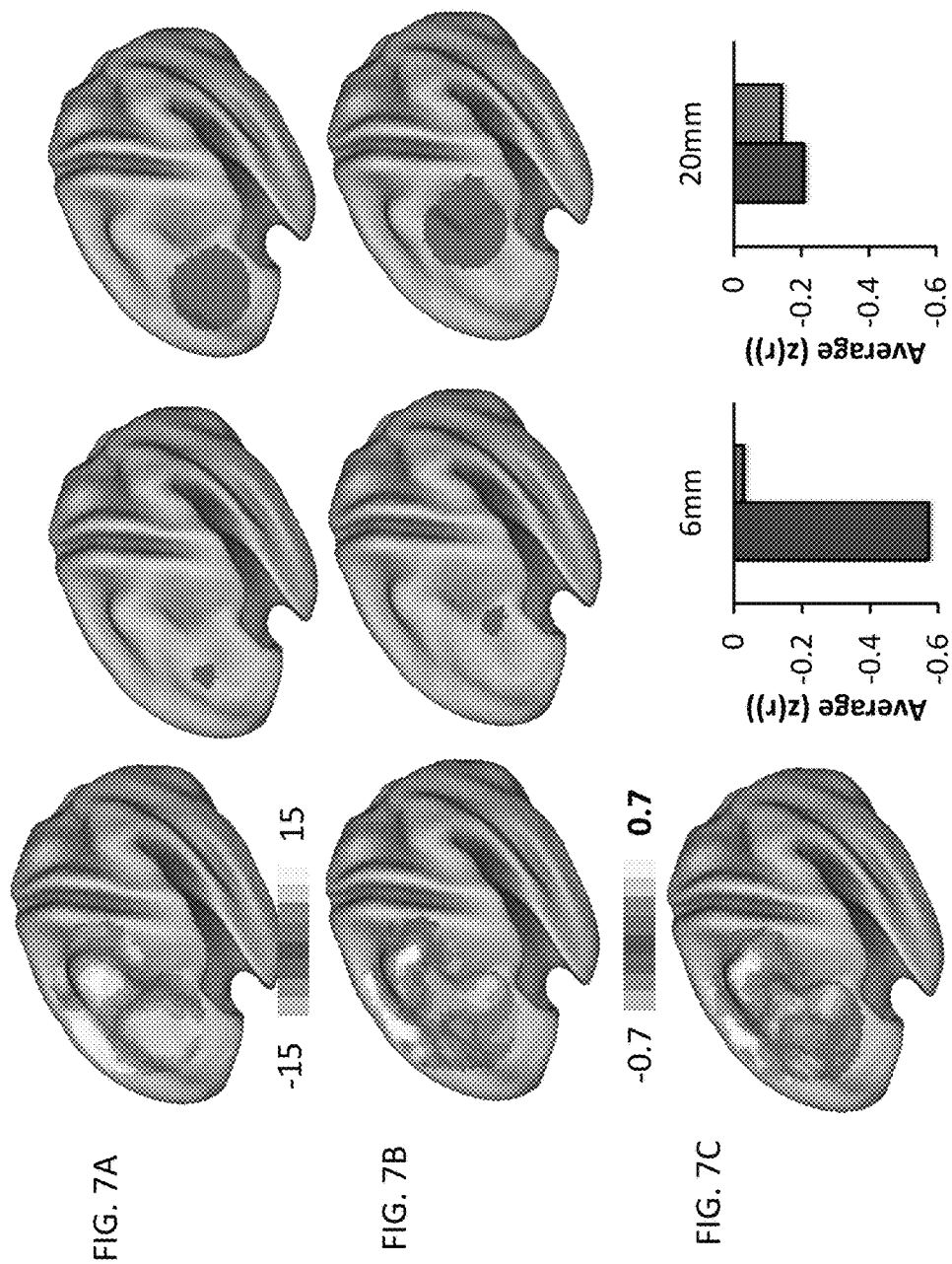
FIGS. 7A-7C illustrate identification of reproducible individualized TMS targets in the DLPFC. Functional connectivity with the subgenual-based seed map is shown for the group (FIG. 7A) or single-subject data from day 1 (FIG. 7B). Using these maps, optimal TMS targets were selected for a focal coil (6 mm radius sphere) or a more diffuse coil (20 mm radius sphere). The average voxel value within these regions was computed using the single-subject fcMRI map from day 2 (FIG. 7C). For both sphere sizes individualized targeting identified a better anticorrelated node than population-based targeting.

FIG. 7: Identification of reproducible individualized TMS targets in the DLPFC. Functional connectivity with the subgenual-based seed map is shown for the group (FIG. 7A) or single-subject data from day 1 (FIG. 7B). Using these maps, optimal TMS targets were selected for a focal coil (6 mm radius sphere) or a more diffuse coil (20 mm radius sphere). The average voxel value within these regions was computed using the single-subject fcMRI map from day 2 (FIG. 7C). For both sphere sizes individualized targeting identified a better anticorrelated node than population-based targeting.

Figure 8:
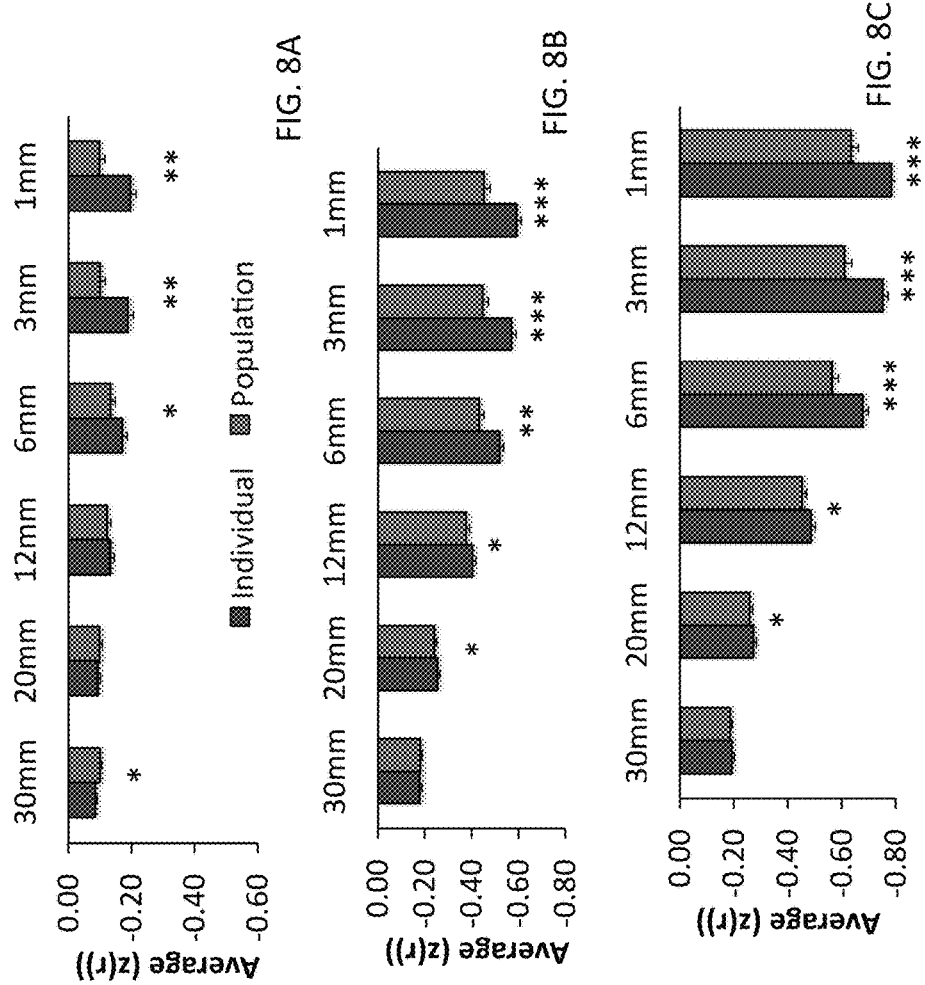
FIGS. 8A-8C illustrate an advantage of individualized versus population-based TMS targets varies with the size of the stimulation filed. Graphs show the average voxel value from day 2 within presumptive TMS target sites of various sizes identified on the basis of either individualized or population-based targeting. Results are shown for the small subgenual ROI (FIG. 8A), the subgenual-based seed map (FIG. 8B), and the efficacy based seed map (FIG. 8C). Significant differences between individualized and population-based targeting are identified. * $P<0.05$,  $P<0.0005$, * $P<10-5$.

FIG. 8: The advantage of individualized versus population-based TMS targets varies with the size of the stimulation filed. Graphs show the average voxel value from day 2 within presumptive TMS target sites of various sizes identified on the basis of either individualized or population-based targeting. Results are shown for the small subgenual ROI (FIG. 8A), the subgenual-based seed map (FIG. 8B), and the efficacy based seed map (FIG. 8C). Significant differences between individualized and population-based targeting are identified. * $P<0.05$,  $P<0.0005$, * $P<10$-5.

FIG. 9: Variability in connectivity across subjects is similar in magnitude to variability in connectivity across space in the dorsal lateral prefrontal cortex (DLPFC). Shown is the standard deviation across subjects for all voxels in the left DLPFC (individual variability, blue) compared to the standard deviation across voxels for all subjects (spatial variability, red) for the three seed regions/seed maps considered in the present article.

Figure 10:
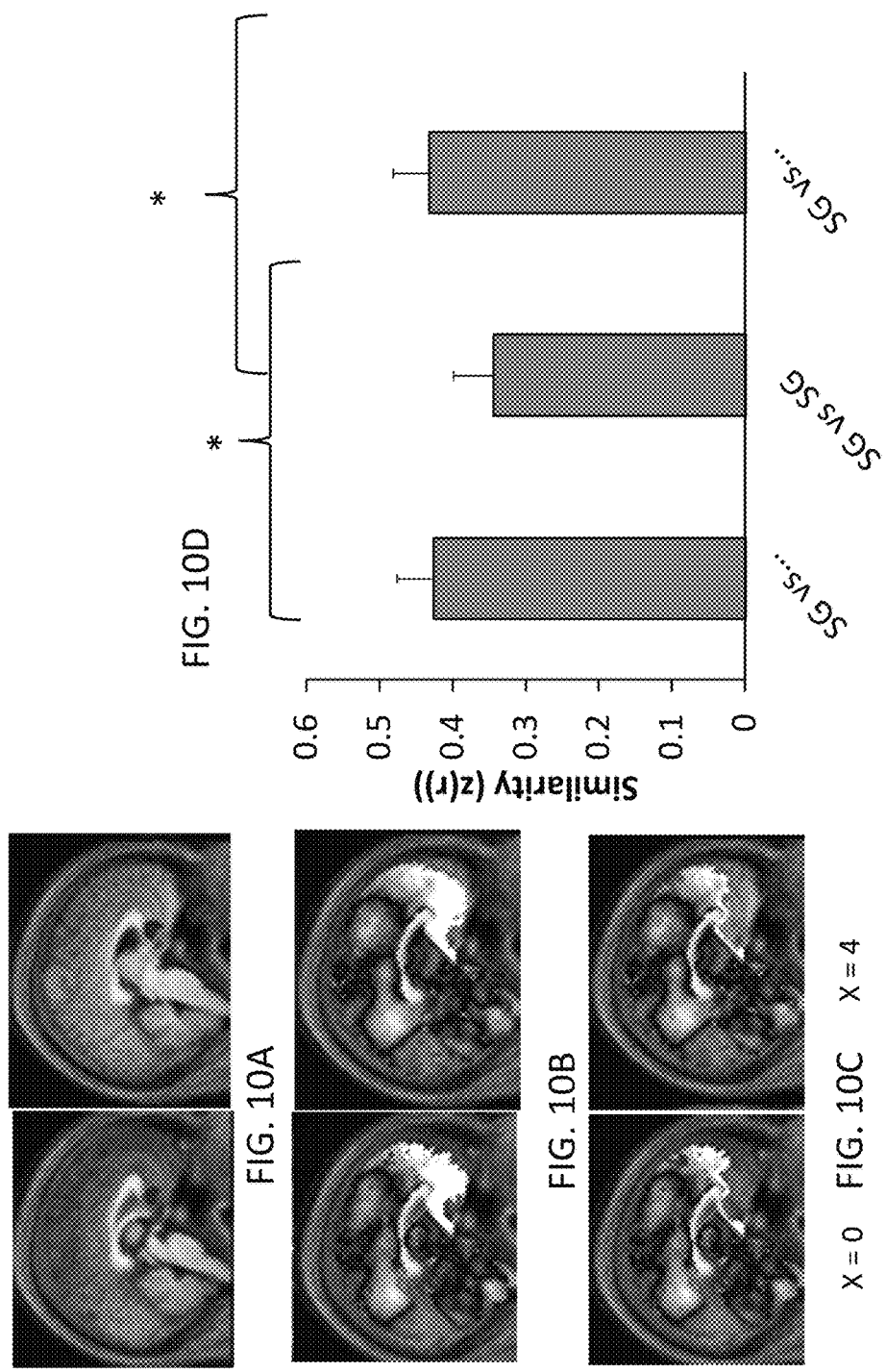
FIGS. 10A-10D illustrate benefit of using a distributed seed map for predicting subgenual connectivity. Connectivity with the subgenual based seed map (SGmap, FIG. 10B) better predicted connectivity with the small subgenual ROT (SG, FIG. 10A) on a different day than connectivity with the small subgenual ROI itself. This remained true even when most of the ventral medial prefrontal cortex was excluded from the subgenual-based seed map (SGmap_subMPF, FIG. 10C).

FIG. 10: Benefit of using a distributed seed map for predicting subgenual connectivity. Connectivity with the subgenual based seed map (SGmap, FIG. 10B) better predicted connectivity with the small subgenual ROT (SG, FIG. 10A) on a different day than connectivity with the small subgenual ROI itself. This remained true even when most of the ventral medial prefrontal cortex was excluded from the subgenualbased seed map (SGmap_subMPF, FIG. 10C).

FIG. 11: Brain slices showing some of the 163 nodes across the cortical surface of the left DLPFC used to generate potential TMS targets. Nodes are separated from other nodes by 3 mm in all directions.

References

Ahdab, R., Ayache, S. S., Brugieres, P., Goujon, C., and Lefaucheur, J.-P. (2010). Comparison of "standard" and "navigated" procedures of TMS coil positioning over motor, premotor and prefrontal targets in patients with chronic pain and depression. Neurophysiologie clinique=Clinical neurophysiology 40, 27-36.

Baldassarre, A., Lewis, C. M., Committeri, G., Snyder, A. Z., Romani, G. L., and Corbetta, M. (2012). Individual variability in functional connectivity predicts performance of a perceptual task. Proceedings of the National Academy of Sciences of the United States of America 109, 3516-3521.

Biswal, B., Yetkin, F., Haughton, V., and Hyde, J. (1995). Functional connectivity in the motor cortex of resting human brain using echo-planar MRI. Magnetic Resonance in Medicine 34, 537-541.

Braun, U., Plichta, M. M., Esslinger, C., Sauer, C., Haddad, L., Grimm, O., Mier, D., Mohnke, S., Heinz, A., Erk, S., et al. (2012). Test-retest reliability of resting-state connectivity network characteristics using fMRI and graph theoretical measures. NeuroImage 59, 1404-1412.

Burt, T., Lisanby, S. H., and Sackeim, H. A. (2002). Neuropsychiatric applications of transcranial magnetic stimulation: a meta analysis. Int I Neuropsychopharmacol 5, 73-103.

Cohen, A. L., Fair, D. A., Dosenbach, N. U., Miezin, F. M., Dierker, D., Van Essen, D. C., Schlaggar, B. L., and Petersen, S. E. (2008). Defining functional areas in individual human brains using resting functional connectivity MRI. NeuroImage 41, 45-57.

Drevets, W. C., Bogers, W., and Raichle, M. E. (2002). Functional anatomical correlates of antidepressant drug treatment assessed using PET measures of regional glucose metabolism. Eur Neuropsychopharmacol 12, 527-544.

Drevets, W. C., Savitz, J., and Trimble, M. (2008). The subgenual anterior cingulate cortex in mood disorders. CNS spectrums 13, 663-681.

Eldaief, M. C., Halko, M. A., Buckner, R. L., and Pascual-Leone, A. (2011). Transcranial magnetic stimulation modulates the brain's intrinsic activity in a frequency-dependent manner. Proceedings of the National Academy of Sciences of the United States of America 108, 21229-21234.

Fitzgerald, P. B., Hoy, K., McQueen, S., Mailer, J. J., Herring, S., Segrave, R., Bailey, M., Been, G., Kulkarni, J., and Daskalakis, Z. J. (2009). A randomized trial of rTMS targeted with MRI based neuro-navigation in treatment-resistant depression. Neuropsychopharmacology 34, 1255-1262.

Fox, M. D., Buckner, R. L., White, M. P., Greicius, M., and Pascual-Leone, A. (2012a). Efficacy of TMS targets for depression is related to intrinsic functional connectivity with the subgenual cingulate. Biological Psychiatry In press.

Fox, M. D., Corbetta, M., Snyder, A. Z., Vincent, J. L., and Raichle, M. E. (2006). Spontaneous neuronal activity distinguishes human dorsal and ventral attention systems. PNAS 103, 10046-10051.

Fox, M. D., and Greicius, M. (2010). Clinical applications of resting state functional connectivity. Front Syst Neurosci 4, 19.

Fox, M. D., Halko, M. A., Eldaief, M. C., and Pascual-Leone, A. (2012b). Measuring and manipulating brain connectivity with resting state functional connectivity magnetic resonance imaging (fcMRI) and transcranial magnetic stimulation (TMS). Neuroimage In press.

Fox, M. D., and Raichle, M. E. (2007). Spontaneous fluctuations in brain activity observed with functional magnetic resonance imaging. Nat Rev Neurosci 8, 700-711.

Fox, M. D., Snyder, A. Z., Vincent, J. L., Corbetta, M., Van Essen, D. C., and Raichle, M. E. (2005). The human brain is intrinsically organized into dynamic, anticorrelated functional networks. PNAS 102, 9673-9678. Fregni, F., and Pascual-Leone, A. (2007). Technology insight: noninvasive brain stimulation in neurology-perspectives on the therapeutic potential of rTMS and tDCS. Nat Clin Pract Neurol 3, 383-393.

Garcia-Toro, M., Salva, J., Daumal, J., Andres, J., Romera, M., Lafau, O., Echevarria, M., Mestre, M., Bosch, C., Collado, C., et at. (2006). High (20-Hz) and low (1-Hz) frequency transcranial magnetic stimulation as adjuvant treatment in medication-resistant depression. Psychiatry research 146, 53-57. George, M. S., Wassermann, E. M., Williams, W. A., Callahan, A., Ketter, T. A., Basser, P., Hallett, M., and Post, R. M. (1995). Daily repetitive transcranial magnetic stimulation (rTMS) improves mood in depression. Neuroreport 6, 1853-1856.

Hallett, M. (2007). Transcranial magnetic stimulation: a primer. Neuron 55, 187-199.

Hampson, M., Driesen, N. R., Skudlarski, P., Gore, J. C., and Constable, R. T. (2006). Brain connectivity related to working memory performance. J Neurosci 26, 13338-13343.

Herbsman, T., Avery, D., Ramsey, D., Holtzheimer, P., Wadjik, C., Hardaway, F., Haynor, D., George, M. S., and Nahas, Z. (2009). More lateral and anterior prefrontal coil location is associated with better repetitive transcranial magnetic stimulation antidepressant response. Biol Psychiatry 66, 509-515.

Herwig, U., Lampe, Y., Juengling, F. D., Wunderlich, A., Walter, H., Spitzer, M., and Schonfeldt-Lecuona, C. (2003a). Add-on rTMS for treatment of depression: a pilot study using stereotaxic coil-navigation according to PET data. J Psychiatr Res 37, 267-275.

Herwig, U., Padberg, F., Unger, J., Spitzer, M., and Schonfeldt-Lecuona, C. (2001). Transcranial magnetic stimulation in therapy studies: examination of the reliability of "standard" coil positioning by neuronavigation. Biol Psychiatry 50, 58-61.

Herwig, U., Satrapi, P., and Schonfeldt-Lecuona, C. (2003b). Using the international 10-20 EEG system for positioning of transcranial magnetic stimulation. Brain Topogr 16, 95-99.

Hoffman, R. E., Hampson, M., Wu, K., Anderson, A. W., Gore, J. C., Buchanan, R. J, Constable, R. T., Hawkins, K. A., Sahay, N., and Krystal, J. H. (2007). Probing the pathophysiology of auditory/verbal hallucinations by combining functional magnetic resonance imaging and transcranial magnetic stimulation. Cereb Cortex 17, 2733-2743.

Kito, S., Fujita, K., and Koga, Y. (2008). Regional cerebral blood flow changes after low-frequency transcranial magnetic stimulation of the right dorsolateral prefrontal cortex in treatment-resistant depression. Neuropsychobiology 58, 29-36.

Kito, S., Hasegawa, T., and Koga, Y. (2011). Neuroanatomical correlates of therapeutic efficacy of low-frequency right prefrontal transcranial magnetic stimulation in treatment-resistant depression. Psychiatry Clin Neurosci 65, 175-182.

Kopell, B. H., Halverson, J., Butson, C. R., Dickinson, M., Bobholz, J., Harsch, H., Rainey, C., Kondziolka, D., Howland, R., Eskandar, E., et al. (2011). Epidural cortical stimulation of the left dorsolateral prefrontal cortex for refractory major depressive disorder. Neurosurgery 69, 1015-1029; discussion 1029.

Koyama, M. S., Di Martino, A., Zuo, X. N., Kelly, C., Mennes, M., Jutagir, D. R., Castellanos, F. X., and Milham, M. P. (2011). Resting-state functional connectivity indexes reading competence in children and adults. The Journal of neuroscience: the official journal of the Society for Neuroscience 31, 8617-8624.

Mannfolk, P., Nilsson, M., Hansson, H., Stahlberg, F., Fransson, P., Weibull, A., Svensson, J., Wirestam, R., and Olsrud, J. (2011). Can resting-state functional MRI serve as a complement to task-based mapping of sensorimotor function? A test-retest reliability study in healthy volunteers. Journal of magnetic resonance imaging: JMRI.

Mayberg, H. S. (2009). Targeted electrode-based modulation of neural circuits for depression. J Clin Invest 119, 717-725.

Mayberg, H. S., Brannan, S. K., Tekell, J. L., Silva, J. A., Mahurin, R. K., McGinnis, S., and Jerabek, P. A. (2000). Regional metabolic effects of fluoxetine in major depression: serial changes and relationship to clinical response. Biol Psychiatry 48, 830-843.

Mayberg, H. S., Lozano, A. M., Voon, V., McNeely, H. E., Seminowicz, D., Hamani, C., Schwalb, J. M., and Kennedy, S. H. (2005). Deep brain stimulation for treatment-resistant depression. Neuron 45, 651-660.

Meindl, T., Teipel, S., Elmouden, R., Mueller, S., Koch, W., Dietrich, O., Coates, U., Reiser, M., and Glaser, C. (2010). Test-retest reproducibility of the default-mode network in healthy individuals. Human brain mapping 31, 237-246.

Mueller, S., Lu, J., Wang, D., Yeo, T., Sabuncu, M. R., Sepulcre, J., Fox, M. D., Li, K., and Liu, H. (2012). Intra-subject and Inter-subject Variability of Intrinsic Functional Connectivity. Human Brain Mapping Annual Conference.

Nahas, Z., Teneback, C., Chae, J. H., Mu, Q., Molnar, C., Kozel, F. A., Walker, J., Anderson, B., Koola, J., Kose, S., et al. (2007). Serial vagus nerve stimulation functional MRI in treatment-resistant depression. Neuropsychopharmacology 32, 1649-1660.

O'Reardon, J. P., Solvason, H. B., Janicak, P. G., Sampson, S., Isenberg, K. E., Nahas, Z., McDonald, W. M., Avery, D., Fitzgerald, P. B., Loo, C., et al. (2007). Efficacy and safety of transcranial magnetic stimulation in the acute treatment of major depression: a multisite randomized controlled trial. Biol Psychiatry 62, 1208-1216.

Ojemann, J. G., Akbudak, E., Snyder, A. Z., McKinstry, R. C., Raichle, M. E., and Conturo, T. E. (1997). Anatomic localization and quantitative analysis of gradient refocused echo-planar fMRI susceptibility artifacts. NeuroImage 6, 156-167.

Padberg, F., and George, M. S. (2009). Repetitive transcranial magnetic stimulation of the prefrontal cortex in depression. Exp Neurol 219, 2-13.

Paillere Martinot, M.-L., Galinowski, A., Ringuenet, D., Gallarda, T., Lefaucheur, J.-P., Bellivier, F., Picq, C., Bruguiere, P., Mangin, J.-F., Riviere, D., et al. (2010). Influence of prefrontal target region on the efficacy of repetitive transcranial magnetic stimulation in patients with medication-resistant depression: a [(18) F)-fluorodeoxyglucose PET and MRI study. The international journal of neuropsychopharmacology official scientific journal of the Collegium Internationale Neuropsychopharmacologicum (CINP) 13, 45-59.

Pascual-Leone, A., Rubio, B., Pallardo, F., and Catala, M. D. (1996). Rapid-rate transcranial magnetic stimulation of left dorsolateral prefrontal cortex in drug-resistant depression. Lancet 348, 233-237. Rajkowska, G., and Goldman-Rakic, P. S. (1995). Cytoarchitectonic definition of prefrontal areas in the normal human cortex: II. Variability in locations of areas 9 and 46 and relationship to the Talairach Coordinate System. Cereb Cortex 5, 323-337.

Rossi, S., Hallett, M., Rossini, P. M., and Pascual-Leone, A. (2009). Safety, ethical considerations, and application guidelines for the use of transcranial magnetic stimulation in clinical practice and research. Clin Neurophysiol 120, 2008-2039.

Rusjan, P. M., Barr, M. S., Farzan, F., Arenovich, T., Mailer, J. J., Fitzgerald, P. B., and Daskalakis, Z. J. (2010). Optimal transcranial magnetic stimulation coil placement for targeting the dorsolateral prefrontal cortex using novel magnetic resonance image-guided neuronavigation. Human brain mapping 31, 1643-1652. Seeley, W. W., Menon, V., Schatzberg, A. F., Keller, J., Glover, G. H., Kenna, H., Reiss, Al., and Greicius, M. D. (2007). Dissociable intrinsic connectivity networks for salience processing and executive control. J Neurosci 27, 2349-2356.

Shehzad, Z., Kelly, A. M., Reiss, P. T., Gee, D. G., Gotimer, K., Uddin, L. Q., Lee, S. H., Margulies, D. S., Roy, A. K., Biswal, B. B., et al. (2009). The resting brain: unconstrained yet reliable. Cereb Cortex 19, 22092229.

Talairach, J., and Tournoux, P. (1988). Co-Planar Stereotaxic Atlas of the Human Brain (New York, Thieme Medical Publishers, Inc.).

van den Heuvel, M. P., Stam, C. J., Kahn, R. S., and Hulshoff Pol, H. E. (2009). Efficiency of functional brain networks and intellectual performance. The Journal of neuroscience: the official journal of the Society for Neuroscience 29, 7619-7624.

van der Kouwe, A. J., Benner, T., Salat, D. H., and Fisch, B. (2008). Brain morphometry with multiecho MPRAGE. NeuroImage 40, 559-569.

Van Dijk, K. R., Hedden, T., Venkataraman, A., Evans, K. C., Lazar, S. W., and Buckner, R. L. (2010). Intrinsic functional connectivity as a tool for human connectomics: theory, properties, and optimization. Journal of neurophysiology 103, 297-321.

Van Dijk, K. R., Sabuncu, M. R., and Buckner, R. L. (2012). The influence of head motion on intrinsic functional connectivity MRI. NeuroImage 59, 431-438.

Van Essen, D. C. (2005). A population-average, landmark- and surface-based (PALS) atlas of human cerebral cortex. Neuroimage 28, 635-662.

Wang, J.-H., Zuo, X.-N., Gohel, S., Milham, M. P., Biswal, B. B., and He, Y. (2011). Graph theoretical analysis of functional brain networks: test-retest evaluation on short- and long-term resting-state functional MRI data. PloS one 6, e21976.

Wu, J., Buchsbaum, M. S., Gillin, J. C., Tang, C., Cadwell, S., Wiegand, M., Najafi, A., Klein, E., Hazen, K., Bunney, W. E., Jr., et al. (1999). Prediction of antidepressant effects of sleep deprivation by metabolic rates in the ventral anterior cingulate and medial prefrontal cortex. Am J Psychiatry 156, 1149-1158. Yeo, B. T., Krienen, F. M., Sepulcre, J., Sabuncu, M. R., Lashkari, D., Hollinshead, M., Roffman, J. L., Smaller, J. W., Zollei, L., Polimeni, J. R., et al. (2011). The Organization of the Human Cerebral Cortex Estimated By Functional Connectivity. Journal of neurophysiology.

Zhu, Q., Zhang, J., Luo, Y. L., Dilks, D. D., and Liu, J. (2011). Resting-state neural activity across face-selective cortical regions is behaviorally relevant. The Journal of neuroscience: the official journal of the Society for Neuroscience 31, 10323-10330.

Zuo, X.-N., Kelly, C., Adelstein, J. S., Klein, D. F., Castellanos, F. X., and Milham, M. P. (2010). Reliable intrinsic connectivity networks. test-retest evaluation using ICA and dual regression approach. Neuroimage 49, 2163-2177.

EXAMPLE 2

Abstract

Both resting state functional magnetic resonance imaging (fcMRI) and transcranial magnetic stimulation (TMS) are increasingly popular techniques that can be used to non-invasively measure brain connectivity in human subjects. TMS shows additional promise as a method to manipulate brain connectivity. In this example we discuss how these two complimentary tools can be combined to optimally study brain connectivity and manipulate distributed brain networks. Important clinical applications include using resting state fcMRI to guide target selection for TMS and using TMS to modulate pathological network interactions identified with resting state fcMRI. The combination of TMS and resting state fcMRI provides a new approach to the diagnosis and treatment of neurological and psychiatric diseases that demonstrate network pathology.

Introduction

It is becoming increasingly recognized that many behavioral manifestations of neurological and psychiatric disease are not solely the result of abnormality in one isolated brain region but represent alterations in brain networks and connectivity. Examples include spatial neglect with imbalance in intraparietal sulcus activity (Corbetta at al., 2005; He et al., 2007), hemiparesis worsened by transcallosal inhibition (Carter et al., 2010; Duque et al., 2005; Grefkes et al., 2008; Murase et al., 2004), memory deficits in Alzheimer's due to distributed network pathology (Buckner et al., 2005), and depression associated with limbic hyperactivity and prefrontal hypoactivity (Mayberg, 2007; Mayberg, 2009; Padberg and George, 2009). As such, much neuroscience research has shifted from focusing on the properties of individual brain regions to the interactions and connections between regions.

Brain connectivity has been non-invasively assessed in human subjects using techniques focused on three general network properties: anatomical connectivity, functional connectivity, and response to perturbation/stimulation. The first of these, anatomical connectivity, has relied predominantly on diffusion tensor imaging (DTI), a technique which measures the asymmetric diffusion of water molecules along white matter fiber tracks (Assaf and Pasternak, 2008). The second network property, functional connectivity, is defined as a correlation between remote neuro-physiological events in the temporal domain (Friston et al., 1993; Horwitz, 2003) and has been assessed using a wide variety of techniques including electro- and magnetoencephalography (EEG/MEG), positron emission tomography (PET), near infrared spectroscopy (NIRS), and functional magnetic resonance imaging (fMRI). Given the variety of approaches used to assess functional connectivity it is important to remember that this is a broad term with some inherent ambiguity (Horwitz, 2003; Rogers et al., 2007). Derivations of functional connectivity include effective connectivity, which uses a priori models to assume directional influence (Stephan and Friston, 2010), and Granger causality, which uses data driven methods to determine whether signals in one region can be predicted by preceding signals in another (Roebroeck et al., 2005). Finally, the third network property which has served as a basis for non-invasive assessment of human brain connectivity is the brain's response to perturbation/stimulation. This approach utilizes techniques such as transcranial magnetic stimulation (TMS), focused pulsed ultrasound (Bystritsky et al., 2011), and transcranial direct current stimulation (TDCS) which can be used alone or in combination with other modalities to measure distributed brain changes occurring as a result of focal brain manipulation.

In this example we focus on two of these techniques for assessing human brain connectivity, namely resting state functional connectivity MRI (fcMRI) and TMS. This focus is motivated by the fact that resting state fcMRI is rapidly becoming the most popular of the correlational techniques for assessing functional connectivity, TMS is the most widely used perturbation approach, and the combination of the two techniques holds great promise for addressing several important clinical issues. Individual reviews have recently been written on both resting state fcMRI (Deco et al., 2011; Fox and Raichle, 2007; van den Heuvel and Hulshoff Pol, 2010) and connectivity assessed with TMS (Hampson and Hoffman, 2010; Reithler and Peters, 2011). Therefore the focus of this example is on the overlap between the two techniques and the ways in which they can be combined. First we review how resting state fcMRI and TMS have been used individually to measure brain connectivity. Second, we highlight some important similarities and differences in connectivity measured using the two techniques. Third we discuss using connectivity including resting state fcMRI to guide TMS target selection. Finally, we explain that TMS can be used to manipulate connectivity and discuss the potential of TMS to correct resting state fcMRI abnormalities in neurological and psychiatric disease.

Measuring Connectivity with Resting State fcMRI Resting state fcMRI examines correlations in spontaneous fluctuations in the blood oxygen level dependent (BOLD) signal (for recent reviews see Deco et al., 2011; Fox and Rachel, 2007; van den Heave and Hulshof Pol, 2010). In contrast to traditional task-based IMRI studies, resting state functional connectivity (fcMRI) studies examine BOLD fluctuations in the absence of any explicit input or output, while subjects simply rest in the scanner. A consistent observation is that regions with similar functional properties, such as the left and right somatomotor cortices, exhibit coherent BOLD fluctuations even in the absence of movement under resting conditions (Biswal et al., 1995; Cordes et al., 2000; De Luca et al., 2005; Fox et al., 2006b; Lowe et al., 1998) (FIG. 12A). Similar findings have been reported in multiple other brain networks including visual, auditory, language, default mode, and corticothalamic networks (Fox and Raichle, 2007). Anticorrelations between regions with apparent opposing functional properties have also been observed (Chang and Clover, 2009; Fox et al., 2005; Fox et al., 2009; Fransson, 2005; Greicius et al., 2003) (FIG. 13D), although some debate exists surrounding the appropriate interpretation of these findings (Anderson et al., 2011; Fox et al., 2009; Murphy et al., 2009). Spontaneous BOLD fluctuations can predict the task-response properties of brain regions (De Luca et al., 2005; Vincent et al., 2006), identify subjects' aptitude for different cognitive tasks (Baldassarre et al., 2012; Hampson et al., 2006; Koyama et al, 2011; Seeley et al., 2007; van den Heuvel et al., 2009b; Zhu et al., 2011), facilitate refinement of neuro-anatomical models (Dosenbach and Fair, 2007; Fox et al., 2006a), and account for trial-to-trial variability in behavior (Fox et al., 2007; Sadaghiani et al., 2010). Resting state fcMRI correlation patterns are very robust and can be observed under sleep (Fukunaga et al., 2006; Horovitz et al., 2009; Larson-Prior et al., 2009) and sedation (Greicius et al., 2008; Kiviniemi et al., 2003; Peltier et al., 2005; Vincent et al., 2007)

allowing for comparisons across development (Dosenbach et al., 2010; Fair et al., 2007) and even species (Vincent et al., 2007).

Importantly, resting state fcMRI may enjoy several practical and theoretical advantages over task based fMRI for clinical applications, including improved signal to noise, reduced need for patient compliance, avoidance of task performance confounds, and expanded patient populations (Fox and Greicius, 2010). Leveraging these advantages, significant resting state fcMRI abnormalities have been identified across almost every major neurological and psychiatric dis-ease (for reviews see Fox and Greicius, 2010; Greicius, 2008; Zhang and Raichle, 2010). These fcMRI abnormalities have been correlated with the severity of disease in depression (Greicius et al., 2007), schizophrenia (Bluhm et al., 2007; Vercammen et al., 2010a), neglect (Carter et al., 2010; He et al., 2007), and hemiparesis (Carter et al., 2010), and can differentiate normal controls from patients with Alzheimer's disease (Greicius et al., 2004; Li et al., 2002; Supekar et al., 2008; Wang et al., 2006) or depression (Craddock et al., 2009).

Despite its potential, there are important limitations to measuring connectivity with resting state fcMRI. First, because patients are not performing a specific task there is no clear measure of performance or mental state. Second, resting state fcMRI is purely correlational in nature, not causal, limiting the conclusions that can be drawn. Third, it is difficult to separate coincidence task-evoked modulation from true connectivity. For example if one hears a beep and sees a flash at the same time the measured correlation between the visual and auditory cortex will increase, but this does not mean the synaptic strength of the connection between the regions has changed. Finally, resting state fcMRI is purely a way to measure, not manipulate functional connectivity. As resting state fcMRI abnormalities continue to be replicated, refined, and clarified, the next step will be translating this information into practical clinical interventions. In such an effort, fcMRI can offer valuable guidance and assessment tools, but combination with methods to manipulate connectivity will be critical.

Measuring Connectivity with TMS

TMS is a noninvasive technique that utilizes short, rapidly changing magnetic field pulses to induce electrical currents in underlying cortical tissue (for reviews see Hallett, 2007; Kobayashi and Pascual-Leone, 2003; Wagner et al., 2007). Single pulses can be used to briefly disrupt or excite underlying cortical tissue while repeated pulses (rTMS) at different frequencies can be used to create changes in cortical excitability that outlast the duration of the stimulation itself. Such lasting modulation of cortical excitability depends on the stimulation parameters and can resemble long-term potentiation (when rTMS is applied in higher frequency, bursting patterns, e.g. in burst of 4 stimuli at 20 Hz with inter-burst pauses of 28 s) or long-term depression (when rTMS is applied at lower frequency as a continuous train, e.g. 20 min of continuous 1 Hz rTMS). The duration of these changes varies depending on the duration of the rTMS train, and can be extended to 90 min of modulation after only a few minutes of stimulation with special stimulation protocols, such as theta-burst stimulation (triplets of stimuli at 50 Hz applied at 5-Hz frequency either continuously or intermittently (Thut and Pascual-Leone, 2010)). Such rTMS-induced modulation of cortical excitability can be done safely if published recommendations and established safety standards are followed (Rossi et at, 2009). In addition to being a powerful research tool, significant clinical effects have been observed across a wide variety of neurological and psychiatric conditions (Burt et al., 2002; Fregni and Pascual-Leone, 2007; Hallett, 2007), and Neuroneticse' Neurostar TMS protocol has been approved by the US Food and Drug Administration (FDA) for the treatment of certain patients with medication-resistant depression (Padberg and George, 2009). Accumulating evidence, from human and animal studies, suggests that TMS modulates neuronal activity beyond the site of stimulation, impacting a distributed network of brain regions (Ferreri et al., 2011; Ruff et al., 2009; Siebner et al., 2009; Valero-Cabre et al., 2005; Valero-Cabre et al., 2007) and that therapeutic and behavioral effects of TMS are mediated by such distributed network effects. Given that TMS effects can propagate beyond the site of stimulation, it has become a powerful tool for measuring brain connectivity.

A simple example of a TMS-based connectivity measure involves delivering a single TMS pulse to primary motor cortex then measuring the induced contralateral muscle contraction in the form of a motor evoked potential (MEP). Note that for the TMS pulse to reach muscle it must cross synapses in the anterior horn of the spinal cord and at the neuromuscular junction. By analyzing the time it takes the TMS pulse to travel this path one can derive central conduction time, a TMS connectivity measure with some clinical utility in spinal injury (Brunholzl and Claus, 1994), multiple sclerosis (Hess et al., 1986), and amyotrophic lateral sclerosis (Floyd et at, 2009).

Connectivity between separate cortical areas can be measured with TMS by pairing stimulations together with two TMS coils, aptly referred to as dual-coil experiments. In the classic example, a conditioning pulse (usually subthreshold) is applied to the primary motor cortex of one hemisphere followed by a test pulse to the motor cortex of the opposite hemisphere (FIG. 12F). If the MEP induced by the test stimulus changes with the addition of the conditioning stimulus this suggests a functional connection between the two sites. Both cortico-cortical inhibition and facilitation can be observed between motor cortices depending on the relative timing of the conditioning and test stimulus (Ferbert et at, 1992; Hanajima et al., 2001). Similar effects on primary motor cortex have been observed with conditioning pulses to cerebellar and frontal sites (Civardi et al., 2001; Ugawa et al., 1991). Dual coil experiments can also be used to assess connectivity with primary and extrastriate visual cortex, where a single TMS pulse can induce the perception of a brief flash of light, called a phosphene. Phosphene perception can be altered based on precisely timed conditioning pulses to other visual areas, frontal eye fields, or parietal cortex (Pascual-Leone and Walsh, 2001; Silvanto et al., 2006; Silvanto et al., 2009). Properly employed, dual-coil methods can be a powerful technique for probing the timing and directionality of the connectivity between cortical regions (Pascual-Leone and Walsh, 2001; Silvanto et al., 2005).

Figure 13A:
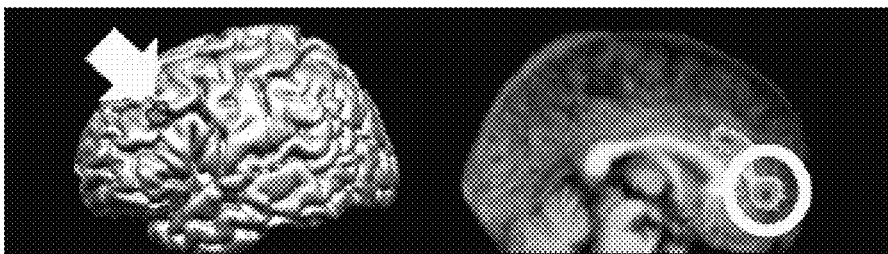
FIGS. 13A-13D illustrate functional connectivity between the left dorsal lateral prefrontal cortex (DLPFC, yellow arrows) and ventral medial prefrontal cortex (yellow circles) assessed with TMS/Imaging and resting state functional connectivity MRI.
Figure 13B:
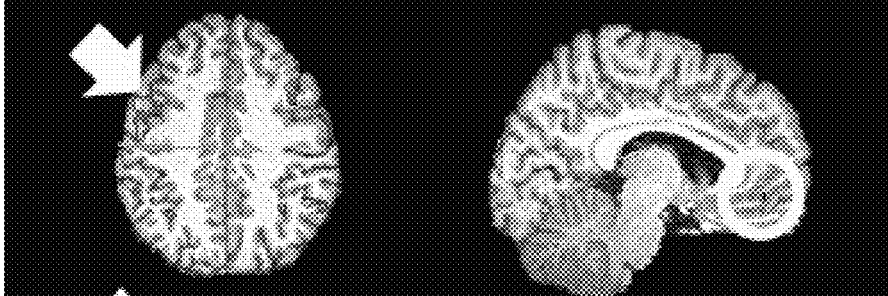
Figure 13C:
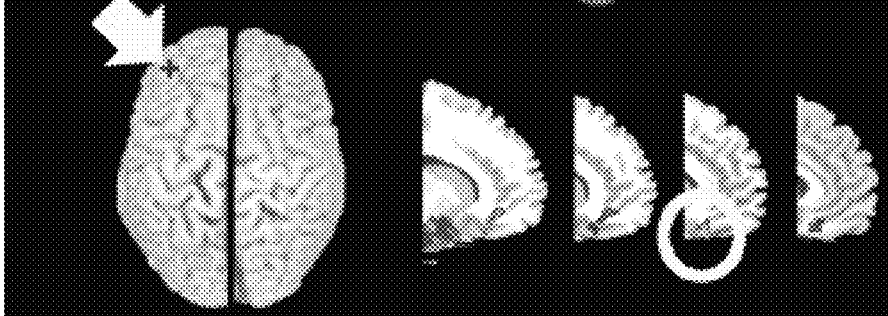
Figure 13D:
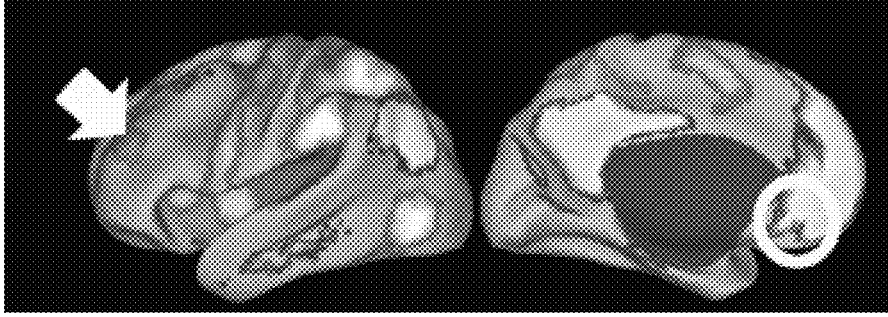

Rather than using two TMS coils, brain connectivity can also be assessed by combining TMS with a second methodology to measure remote effects of stimulation in connected brain regions. This approach has resulted in an increasing number of TMS-EEG, TMS-PET, and TMS-fMRI experiments (Bestmann et al., 2008; Hampson and Hoffman, 2010; Reithler and Peters, 2011; Ruff et al., 2009). Remote effects can be measured simultaneously with TMS in an online approach, or before and after rTMS in an offline approach. While a full review of this extensive literature is beyond the scope of this example, we highlight a few examples to illustrate the strengths of various multi-modal TMS-based connectivity approaches. For example, the temporal resolution of EEG has been utilized to time the spread of ex-citation to connected brain regions following focal TMS to the prima-rye sensorimotor cortex (Ilmoniemi et al., 1997). The spatial resolution of PET has been used to show remote cerebral blood flow (CBF) in-creases in the parietal/occipital cortex in response to frontal eye field stimulation (Pans et al., 1997) and remote CBF decreases in the peri-cingulate region in response to stimulation to the dorsolateral prefrontal cortex (DLPFC) (Pans et al., 2001) (FIG. 13A). Using PET radioligands specific to neurotransmitter binding sites, excitatory TMS to the left (but not right) DLPFC has been shown to cause dopamine release in the subgenual cingulate cortex (Cho and Strafella, 2009) (FIG. 13C).

Further improving on spatial resolution with fMRI, inhibitory TMS to the left dorsal premotor cortex has been shown to reduce activation in the left premotor cortex, but increase activation in the right dorsal premotor cortex and medial motor areas when subjects perform a subsequent motor task, resembling adaptive changes observed post stroke (O'Shea et al., 2007). While technically challenging, simultaneous TMS-fMRI can provide both good spatial and temporal resolution (Bestmann et al., 2008). For example, one can examine both the distributed activation pattern and time-course of TMS to the left DLPFC (Li et al., 2004) (FIG. 13B). Using this simultaneous approach, TMS to the frontal eye fields has been shown to increase activity in retinotopic representations of the peripheral visual field, but decrease activity in the central field, a result that matches psycho-physical changes in contrast perception (Ruff, Blankenburg, et al, 2006).

There are several important limitations to connectivity assessed with TMS. First, it stimulates neuronal tissue exogenously and artificially, thus connectivity revealed by TMS may be different than connectivity present under more physiological conditions. Second, TMS can only selectively target areas along the cortical surface, thus assessing connectivity to or between deep brain structures becomes difficult or impossible. Presently available 'deep TMS coils' such as the H-coil can enable penetration to deeper brain structures, but also stimulate surface cortex immediately under the coil and thus do not allow for selective deep stimulation (Deng and Peterchev, 2008; Roth et al., 2007). Eventually, multi-coil TMS arrays may offer technical solutions to this limitation. Third, connectivity measured with TMS alone (e.g. dual coil paradigms) can only be assessed in cortex with a clear TMS output effect (e.g. motor or visual cortices) and connectivity between other structures necessitates the addition of a secondary monitoring method (e.g. EEG or neuroimaging). Fourth, remote changes observed in response to TMS with EEG or neuroimaging could reflect other factors besides propagation of TMS activity along cortical connections creating some interpretive ambiguity. These factors could include associated effects of TMS (e.g. tapping sensation or clicking noise), behavioral or cognitive consequences of the TMS leading to changes in brain activity, or neuronal adaptation to the TMS perturbation. Finally, the selection of an appropriate stimulation target is an ongoing clinical problem in TMS, an issue that will be discussed further in our section on using functional connectivity to guide TMS target selection.

Does Connectivity Measured with fcMRI and TMS Reflect the Same Underlying Phenomenon?

TMS and resting state fcMRI are complimentary techniques that if combined can compensate for the limitations of either technique alone, providing insight into a variety of neuroscience questions and facilitating the translation of both techniques into clinical care. A first step towards combining these techniques is to determine if con-nativity assessed with resting state fcMRI is the same as connectivity assessed with TMS. By comparing results across different studies some useful insights can be gained.

As one might expect, connectivity assessed using either resting state fcMRI or TMS is related to and constrained by underlying anatomical connectivity. DTI, a noninvasive measure of anatomical connectivity, has been shown to relate well to both functional connectivity measured with resting state fcMRI (De Luca et al., 2006; Greicius et al., 2009; Honey et al., 2009; Koch et al., 2002; Lowe et al., 2008; Skudlarski et al., 2008; van den Heuvel et al., 2008; van den Heuvel et al., 2009a; Zhang et al., 2010) and connectivity as assessed with TMS (Voineskos et al., 2010; Wahl et al., 2007). Some of the strongest evidence comes from studies relating individual differences in transcallosal connectivity measured with DTI to that measured with resting state fcMRI (Lowe et al., 2008), paired pulse TMS (Wahl et al., 2007; Wahl et al., 2011), and TMS-EEG (Voineskos et al., 2010). Surgical sectioning of the corpus callosum disrupts interhemispheric connectivity assessed with resting state fcMRI (Johnston et al., 2008) and individuals with agenesis of the anterior trunk of the corpus callosum show disrupted transcallosal inhibition with paired pulse TMS (Meyer et al., 1995). It is important to note that connectivity assessed with either technique involves poly-synaptic connections. For example, resting slate fcMRI is present between regions in the monkey visual system with no direct anatomical connections (Vincent et al., 2007), and the simple presence of a muscle twitch after TMS to the motor cortex implies polysynaptic transmission.

An advantage of both fcMRI and TMS over purely anatomical con-nativity measures is that they can provide information on the functional consequences of anatomical connections. Both resting state fcMRI and TMS have revealed results potentially consistent with ex-citatory versus inhibitory connections, however interpretation of these results and the relationship between techniques is likely to be complicated. For example, the bilateral somatomotor cortices are positively correlated when connectivity is assessed with resting state fcMRI (FIG. 12A). This is consistent with inter-hemispheric facilitation using dual-coil TMS (Hanajima et al., 2001), changes in motor cortex excitability matching excitatory/inhibitory rTMS to the opposite side (Gorsler et al., 2003), and some TMS-PET findings showing a contra-lateral increase in activity in response to excitatory M1 stimulation (Ferrarelli et al., 2004; Siebner et al., 2000), However dual-coil TMS can also produce transcallosal inhibition (Ferbert et al., 1992) (FIG. 1B) and other TMS-PET studies have reported contralateral decreases in motor cortex activity in response to ipsilateral stimulation (Fox et al. 1997; Fox et al., 2006c).

In a second example of how these techniques may provide insight into the functional consequences of anatomical connections, we consider the relationship between the left dorsal lateral prefrontal cortex (DLPFC) and the ventral medial prefrontal cortex (FIG. 13). TMS-fMRI (Li et al., 2004), TMS-PET measuring CBF (George et al., 1999; Paus et al., 2001), TMS-PET measuring dopamine binding (Cho and Strafella, 2009), and resting state fcMRI (Fox et al., 2005) all suggest a functional connection between these two regions (FIG. 13) which may have some precedence in track tracing results in monkeys (Petrides and Pandya, 1999; Vogt and Pandya, 1987). Interestingly, TMS-fMRI (Li et al., 2004), TMS-PET measuring CBF (George et al., 1999; Paus et al., 2001), and resting state fcMRI (Fox et al., 2005) all (Petrides and Pandya, 1999; Vogt and Pandya, 1987). Interestingly, TMS-fMRI (Li et al., 2004), TMS-PET measuring CBF (George et al., 1999; Paus et al., 2001), and resting state fcMRI (Fox et al., 2005) all suggest that this interaction may be inhibitory, such that when the DLPFC is stimulated with TMS or activity in the DLPFC increases spontaneously, activity in the ventral medial prefrontal cortex is suppressed. Obviously there is significant heterogeneity in the DLPFC and combined studies are needed before any real conclusions can be drawn, however this convergence across techniques could have important implications for network models of depression (Mayberg, 2007). Further, there has been substantial debate surrounding the interpretation of anticorrelations observed with resting state fcMRI (Anderson et al., 2011; Fox et al., 2009; Murphy et al., 2009), and evidence showing that stimulation to one region could causally suppresses activity in an anticorrelated region would go far in validating the functional importance of this relationship.

An important area where the relationship between resting state fcMRI and TMS is unclear is in context dependence-of the measured connectivity. The idea that neuronal networks reorganize in the con-text of different task conditions has a strong precedent (Marder and Weimann, 1991), and animal studies have shown context-dependent changes in neuronal synchrony (Engel et al., 2001; Varella et al., 2001). Similarly, accumulating evidence suggests that connectivity assessed with TMS depends on the task context (Koch and Rothwell, 2009; Ruff et al., 2009). For example, in an elegant dual-coil TMS study connectivity was assessed between the left dorsal premotor cortex (conditioning pulse) and right primary motor cortex (test pulse) during a task in which subjects were cued to move either their right or left hand (Koch et al., 2006). A facilitatory connection was observed 75 ms after a tone indicating left hand movement (but not right hand movement), while an inhibitory connection was observed 100 ms after a tone indicating right hand movement (but not left hand movement). This shows that the strength and sign of the functional connection between these two regions varies with both time and task context.

Due to its poorer temporal resolution and inability to exert causal perturbations, the context dependence of connectivity assessed with fcMRI remains less clear. Many groups have reported changes in fcMRI between rest conditions and task performance Arfanakis et al., 2000; Bartels and Zeki, 2005; Cordes, et al., 2000; Fransson, 2006; Hampson et al., 2002: Hampson et al., 2004; Jiang et al., 2004; Lowe et al., 2000; Morgan and Price, 2004; Nir et al., 2006; Sun et al., 2006), generally reporting an increase in the correlation between regions similarly activated by the task and a decrease between regions not similarly activated. However, interpretation of these results is confounded by the superposition of task-evoked activity on top of resting state fluctuations (Fox et al, 2006b) and apparent context-dependent changes in connectivity can disappear after correction for task-evoked activity (Arfanakis et al., 2000). Examining resting state fcMRI before and after tasks can circumvent this confound, an approach that has been used to document modulation of resting state functional connectivity by learning tasks (Albert et al., 2009; Lewis et al., 2009; Tambini et al., 2010).

Finally, both techniques have identified connectivity changes across a range of altered states including neurological and psychiatric conditions with both concordant and discordant results (Burt et al., 2002; Fox and Greicius, 2010; Fregni and Pascual-Leone, 2007; Greicius, 2008; Hallett, 2007; Zhang et al., 2010). For example, both measures agree that there is a decrease in connectivity with sleep (Horovitz et al., 2009: Massimini et al., 2005), sedation (Ferrarelli et al., 2010; Greicius et al., 2008), and across the corpus callosum in patients with multiple sclerosis (Lowe et al., 2008; Wahl et al., 2011). However in blind subjects TMS-PET suggests increased connectivity between primary somatosensory and visual cortices (Wittenberg et al., 2004) while resting state fcMRI suggests that con-nativity is decreased (Liu et al., 2007; Yu et al., 2008). Further work combining both measures in the same subjects and patient populations is needed to help understand the similarities and differences in these two connectivity techniques.

Using Connectivity to Guide TMS

The recognition that one is manipulating a network and not just a single brain region with TMS complicates an ongoing difficulty: How does one select the optimal site for stimulation? For example, clinical TMS for treatment of depression identifies the dorsal-lateral prefrontal cortex (DLPFC) stimulation site by moving 5 cm anterior to the motor cortex (George et al., 1996; Pascual-Leone et al., 1996), a technique which frequently misses the DLPFC completely (Ahdab and Ayache, 2010; Herwig et al., 2001) and contributes to variability in clinical response (Herbsman et al., 2009; Padberg and George, 2009). TMS effects can be improved by targeting based on individual MRI anatomy (Fitzgerald et al., 2009; Gugino et al., 2001) and even further augmented using individual fMRI derived activation foci (Sack et al., 2009). However, these approaches have translated into only modest clinical improvements. For example, anatomical DLPFC targeting improved depression scores more than standard targeting, but the study's primary outcome measure failed to reach significance (Fitzgerald et al., 2009). Similarly, three depression trials targeting TMS based on foci of hypometabolism in the prefrontal cortex failed to improve patient outcomes beyond standard targeting (Garcia-Toro et al., 2006; Herwig et al., 2003; Paillere Martinot et al., 2010). One of the critical limitations of these efforts to improve TMS targeting may be that they have focused on the stimulation site alone and have not taken into account the distributed network properties of the targeted region.

Despite its potential, surprisingly few studies have used distributed network connectivity to guide TMS target selection. In an excellent example of how connectivity can guide TMS, diffusion tensor imaging (DTI) was used to identify subject-specific targets in the middle frontal gyrus that were connected to a particular portion of primary somatosensory cortex (Hannula et al., 2010). TMS to this focus improved tactile working memory, but not TMS to non-connected portions of the middle frontal gyrus located just 18 mm away.

A few studies have used task-based fcMRI measures (as opposed to resting state fcMRI) to identify stimulation targets (Bien and Roebroeck. 2009; de Graaf et al., 2009; Zanto et al., 2011), In perhaps the best example of this approach, functional connectivity with extra-striate visual areas (V4 and V5) during the encoding phase of a selective-attention delayed-recognition task was used to identify subject-specific targets in the inferior frontal junction (IFJ) thought to be involved in top-down modulation (Zanto et al., 2011). Inhibitory TMS to this site disrupted both behavioral performance and EEG measures of top-down influence. Further, the magnitude of the TMS-induced change in EEG was related to the strength of functional connectivity between IFJ and V4 across subjects. Similar studies have used task-based functional connectivity to target frontal TMS targets correlated with posterior parietal cortex during a visuospatial judgment task (de Graaf et al., 2009) or correlated with regions involved in a set of imitation tasks (Bien and Roebroeck, 2009) with similar disruption in task performance. Although these studies certainly speak to the potential of functional connectivity to guide TMS target selection, an issue that complicates interpretation of these findings is the fact that the frontal targets are themselves activated by the task. It is therefore difficult to determine if it is truly the connectivity to other regions that mediates the frontal TMS effect, or if these regions could be identified just as well using traditional activation mapping. If the latter is true, the observed TMS effect could simply be the result of disrupting another region involved in the task without any clear dependence on connectivity. Further efforts linking the magnitude of TMS-induced changes to the strength of the functional connectivity between regions (Zanto et al., 2011), or showing, that TMS to a connected region not modulated by the task has an effect on task performance will be important in clarifying these issues.

Figures 14A, 14B, 14C, 14D:
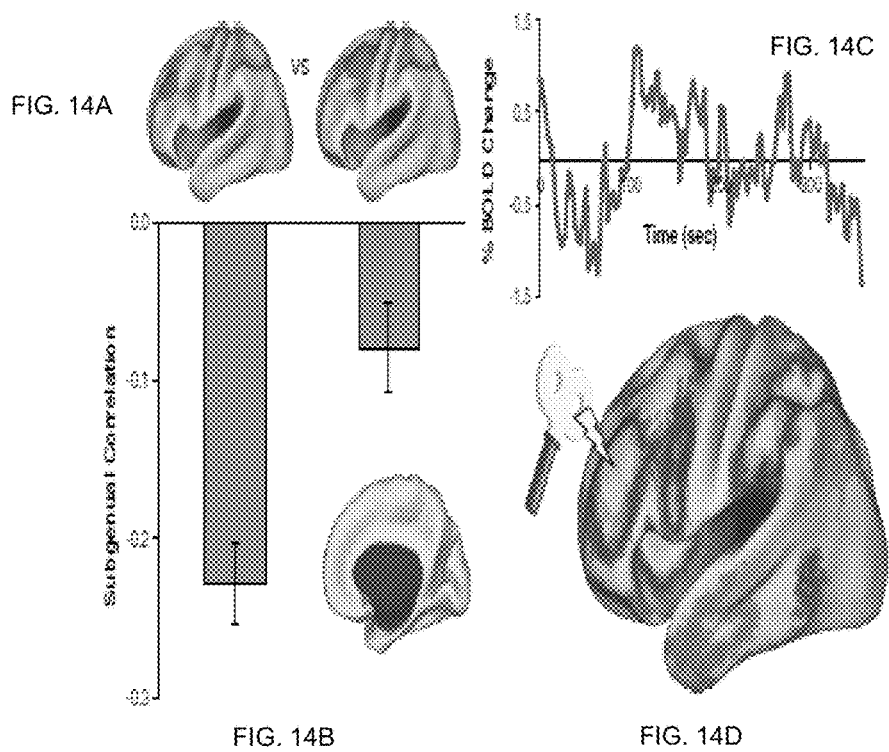
FIG. 14A illustrates using resting state fcMRI to target therapeutic TMS. TMS targets in the left dorsal lateral prefrontal cortex (DLPFC) known to be more effective (left) versus less effective (right) at producing an antidepressant response.
FIG. 14B illustrates using resting state fcMRI to target therapeutic TMS. Resting state functional connectivity reveals that the more effective target is more negatively correlated (anticorrelated) with the subgenual (inset) compared to the less effective target.
FIG. 14C illustrates using resting state fcMRI to target therapeutic TMS. Resting state BOLD time course extracted from the subgenual.
FIG. 14D illustrates using resting state fcMRI to target therapeutic TMS. Resting state functional connectivity identifies a theoretically optimal stimulation target in the left DLPFC based on anticorrelation with the subgenual. (Modified from Fox et al., 2012).

Finally, a handful of studies have begun using resting state fcMRI to guide TMS target selection. Eldaief and colleagues recently used resting state fcMRI with the posterior cingulate to target rTMS to a connected region of the lateral parietal cortex in order to modulate activity within the default mode network (Eldaief et al., 2011). In an early example of using resting state fcMRI to guide therapeutic TMS, Hampson and colleagues targeted inhibitory TMS to regions correlated with Wernikes area in a small set of patients with schizophrenia and continuous auditory hallucinations (Hoffman et al., 2007). Unfortunately rTMS to these targets did not lead to symptomatic improvement. Recently, we have examined the utility of resting state fcMRI to address the above referenced clinical problem of determining where to target rTMS in the DLPFC to improve antidepressant response (Fox et al., 2012). We first identified DLPFC target coordinates known to be more effective versus less effective based on prior TMS clinical studies (Fitzgerald et al., 2009) (FIG. 14A). We then examined differences in fcMRI between these two targets and found that more effective sites were more negatively correlated (anticorrelated) with the subgenual cingulate cortex, a region thought to play a key role in the pathophysiology of depression and antidepressant response (Drevets et al., 2008; Mayberg, 2009; Mayberg et al., 2005) (FIG. 14B). Based on these results, we extracted the BOLD time course from the subgenual cingulate (FIG. 14C) then used fcMRI to identify a theoretically optimal target site in the DLPFC (FIG. 14D). While this initial analysis was performed on a population of subjects, this approach could be similarly used to identify individualized TMS targets for specific patients. Obviously, clinical trials are needed to determine the clinical utility of this approach, but this connectivity-based targeting paradigm has the potential to improve therapeutic stimulation across a range of diseases with distributed network pathology.

Moving forward, we anticipate great value in targeting TMS based on individualized connectivity with distributed brain networks. The following issues need to be considered:
1) Identification of a remote region or network to be manipulated;
2) Connection between the region or network one is trying to manipulate and a target on the cortical surface accessible by TMS;
3) Spatial heterogeneity of the connectivity in the targeted region (for targeting based on connectivity to be advantageous over anatomy alone);
4) Subject to subject heterogeneity of the connectivity of the targeted region (for individualized targeting to be advantageous over average coordinates);
5) Reproducibility of individualized target identification across sessions.

Manipulating Connectivity with TMS

A unique advantage of TIVIS compared to fcMRI, and every other noninvasive approach for assessing connectivity, is that TMS can also be used to manipulate connectivity. In fact, it is becoming apparent that some of the clinical effects of rTMS may be due more to TMS induced changes in connectivity between brain regions than local effects on the stimulated region itself (Grefkes et al., 2010). Further, as techniques such as resting state fcMRI continue to identify reproducible pathological abnormalities in connectivity the ability of TMS to manipulate connectivity will become increasingly important.

Two different TMS-based approaches have been employed to alter connectivity, repetitive TMS (rTMS), by far the most popular approach, and paired associative stimulation (PAS), which will be dis-cussed later. While it can be argued that the local effects of rTMS on cortical excitability are due to changes in connectivity within the stimulated region itself, the current example is focused on connectivity between brain regions, rTMS induced changes in connectivity between regions have been studied using a wide variety of connectivity measurement techniques including dual-coil TMS (Pal et al., 2005), TMS-PET (Paus et at, 2001), EEG coherence (Fuggetta et al., 2008; ling and Takigawa, 2000; Oliviero et al., 2003; Strens et al., 2002; Zanto et al., 2011), task-based effective connectivity with PET (Lee et al., 2003), task-based effective connectivity with fMRI (Graces et al., 2010; Pleger et al, 2006), and finally resting state fcMRI (Eldaief et al., 2011; van der Werf et al., 2010; Vercammen et al., 2010b) (Table 1).

Given the variety of different connectivity measurement techniques used in the above studies, rTMS can be used to alter cortico-cortical connectivity. Each of these different approaches offers unique advantages and disadvantages; however taken collectively they raise several important points regarding assessing rTMS-induced connectivity changes.

First, it is important to consider whether an observed change in connectivity actually reflects a change in connection strength between remote areas or whether it could be explained by local effects of the rTMS alone. This is particularly problematic if TMS perturbation to the area just stimulated with rTMS is part of the connectivity measure (Paus et al., 2001; Pal et al., 2005). Pal et al. showed appropriate concern for this issue in their dual-coil paradigm by adjusting the conditioning stimulus to maintain motor evoked potential amplitude; however this cannot completely exclude local effects not measured by the MEP. Even if one is not using TMS as part of the connectivity measure, differentiating changes in connectivity from purely local effects remains difficult. Studies that find a change in connectivity be-tween remote regions that have not been stimulated make an important advance in this regard (Davare et al., 2010; Grefkes et al., 2010; van der Werf et al., 2010). Second, when connectivity is being assessed during a task, it is important to determine if the measured change in connectivity is actually due to a change in behavior (as opposed to the change in behavior being due to a change in connectivity). Studies in which the stimulation does not change task performance are helpful in excluding this possibility (Lee et al., 2003), but note that a change in cognitive or behavioral strategy could alter brain activity while not being captured by task performance. Third, it is important to control for as many non-specific effects as possible. An ideal study would vary stimulation frequency, stimulation site, and the networks examined to show maximal specificity of an rTMS induced connectivity change. For example, excitatory rTMS over primary motor cortex decreased ipsilateral cortico-cortical alpha band coherence (Oliviero et al., 2003) while inhibitory stimulation increased it (Sirens et al., 2002), showing specificity of the observed connectivity change for the stimulation frequency, Finally, in the case of effective connectivity it is important to recognize that results will be constrained by the model applied. Other regions or connections not included in the model could be significantly altered and would be missed by the model-driven analysis.

Figure 15:
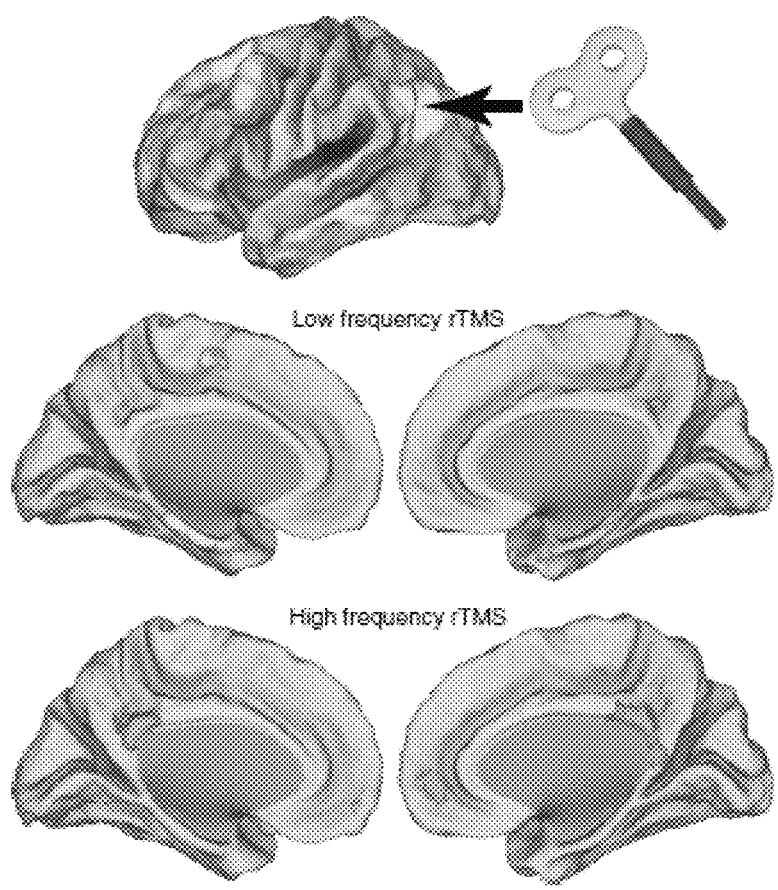
FIG. 15. illustrates modulating resting state functional connectivity networks using TMS. Both inhibitory and excitatory TMS were applied to the left inferior parietal lobule, part of the default mode network (top row). Inhibitory TMS resulted in pronounced increases in functional connectivity between the stimulation site and the medial temporal lobe (middle row) while excitatory TMS resulted in decreased correlation between the stimulation site and other nodes of the default mode network (bottom row). (Modified from Eldaief et al., 2011).

Assessing rTMS induced connectivity changes with resting state fcMRI may help avoid some of the above interpretive difficulties; therefore we expect studies in this area to increase. An early study to examine such effects acquired resting state fcMRI data following low frequency rTMS to left DLPFC and sham stimulation (van der Werf et al., 2010). In an analysis restricted to the default mode network, they showed that rTMS resulted in a reduction in functional connectivity between the default mode network and lateral temporal cortices with a trend towards reduced functional connectivity with the bilateral hippocampus. Although sham controlled, they did not show specificity of the effect to their network of interest, stimulation site, or stimulation frequency. A recent study incorporating some of these additional controls acquired resting state fcMRI data before and after low and high frequency stimulation to the left posterior inferior parietal lobule, a node of the default mode network (Eldaief et al., 2011). Following low frequency rTMS, intrinsic correlations were increased between the stimulation site and the hippocampal formation. Following high frequency stimulation, correlations be-tween multiple nodes of the default node network were decreased but correlations with the hippocampus were unchanged (FIG. 15). No significant effects were seen in other networks such as somatomotor, visual, or auditory. While this study was again limited to one stimulation site, they showed specificity for their network of interest and stimulation frequency. Comparing results across these two rTMS-resting state fcMRI studies, low frequency stimulation appears to have opposite effects on functional connectivity between the default mode network and the hippocampus depending on the stimulation site. Interestingly, resting state fcMRI correlations observed between the two stimulation sites and the hippocampus are also opposite; the DLPFC is negatively correlated with the hippocampus while the inferior parietal lobule is positively correlated (FIG. 13D) (Fox et al., 2005). Whether this observation is anything more than coincidence will require future work.

The ability of rTMS to manipulate connectivity as measured by resting state fcMRI shows that it may be used to modify resting state fcMRI abnormalities observed in disease states that might result in behavioral gains for the patient. The above rTMS-induced manipulations of resting state fcMRI in the default mode network may prove valuable in disorders where fcMRI abnormalities in this network have been observed, including schizophrenia (Whitfield-Gabrieli et al., 2009), depression (Greicius et al, 2007) and Alzheimer's disease (Greicius et al., 2004). To our knowledge, only one study of rTMS-induced changes in connectivity has been aimed at rectifying resting state fcMRI abnormalities in patients (Vercammen et al., 2010b). Based on prior work relating the severity of auditory hallucinations to reduced resting state connectivity between the left temporal parietal junction (TPJ) and bilateral cingulate and amygdala (Vercammen et al., 2010a) and evidence that inhibitory rTMS to the left TPJ could improve these symptoms (Freitas et al., 2009), it was hypothesized that rTMS might normalize functional connectivity between these regions. In a study of 18 patients with schizophrenia there was a trend towards symptomatic benefit but no rTMS-induced change in resting state connectivity between the left TPJ and bilateral cingulate or amygdala (Vercammen et al., 2010b). However there was an rTMS-induced increase in connectivity between the left TPG and right insula not seen with sham stimulation.

The above study in patients with auditory hallucinations represents an excellent example of how one might combine resting state fcMRI with TMS to identify then correct abnormalities in brain connectivity, however, it is important to realize that in the pathological brain, restoring a normal pattern of activity within a given neural network may not be the most effective way to suppress symptoms. Instead, what might need to be done is induce other changes that may prove behaviorally more adaptive. In addition, the study by Vercammen et al. (2010b) also highlights a potentially important limitation of rTMS. While rTMS does appear to alter connectivity, it currently seems to do so in unpredictable ways, often between unexpected regions. One alternative approach that may help understand this issue is termed paired associative stimulation and uses Hebbian principles of synaptic plasticity to modify connectivity in a highly controlled manner.

TABLE 1

Connectivity changes in the human brain observed in response to focal rTMS.

| Connectivity measurement | Stimulation | Connectivity change | Comments | References |
|---|---|---|---|---|
| Dual-coil TMS during rest | Inhibitory rTMS to primary motor cortex | Decreased inter-hemispheric inhibition with contralateral M1 | Difficult to exclude local effects (although persists when the strength of the conditioning stimulus is adjusted) | Pal et al. (2005) |
| Dual-coil TMS during rest and task | Inhibitory rTMS (continuous theta burst) to the anterior intraparietal area | Decreased connectivity between ventral premotor and M1 during grasp preparation | Effects were context dependent (not seen during rest) | Davare et al. (2010) |
| Resting state EEG coherence | Excitatory rTMS to primary motor cortex | Decreased ipsilateral cortico-cortical alpha band coherence | | (Fuggetta et al., 2008; Oliviero et al., 2003) |
| Resting state EEG coherence | Inhibitory rTMS to primary motor cortex | Increased ipsilateral cortico-cortical alpha band coherence | Effects observed up to 25 min post stimulation | Strens et al. (2002) |
| Resting state EEG coherence | Excitatory rTMS to the left frontal area | Increased directed coherence from stimulated site to other cortical nodes (especially parietal) | Intra-hemispheric change more pronounced than the inter-hemispheric change | Jing and Takigawa (2000) |

TABLE 1-continued

Connectivity changes in the human brain observed in response to focal rTMS.

| Connectivity measurement | Stimulation | Connectivity change | Comments | References |
|---|---|---|---|---|
| Task-based EEG coherence | Inhibitory rTMS to the premotor area | Increase in task related coherence between motor regions | | Chen et al. (2003) |
| Task-based EEG coherence | Inhibitory rTMS to the right inferior frontal junction | Decreased ipsilateral alpha band coherence during task | | Zanto et al. (2011) |
| Resting state TMS-PET | Excitatory rTMS to the left DLPFC | Increased connectivity from DLPFC to cingulate regions | Difficult to exclude local effect of rTMS on the DLPFC | Paus et al. (2001), |
| Resting state functional connectivity with PET | Inhibitory rTMS to the left temporal+31 parietal junction | Decreased connectivity between the stimulated node and a wide variety of regions | Difficult to exclude local effect of rTMS on the TPJ, performed in patients with schizophrenia and auditory hallucinations | Horacek et al. (2007) |
| Task-based effective connectivity with PET | Inhibitory rTMS to primary motor cortex | Decreased connectivity between stimulated M1 and premotor/mesial motor areas. Increased coupling between an inferomedial portion of M1 and anterior motor areas. | | Lee et al. (2003) |
| Task-based effective connectivity with fMRI | Excitatory rTMS to primary sensory cortex | Increased effective connectivity from S1 to M1 | Persists up to 120 min; correlated with behavioral improvement in tactile discrimination | Pleger et al. (2006) |
| Task-based effective connectivity with fMRI | Inhibitory rTMS to contralesional M1 in stroke patients | Increased effective connectivity between ipsilesional M1 and ipsilesional SMA | Related to clinical improvement in the movement of the paretic hand | Grefkes et al. (2010) |
| Resting state fcMRI | Inhibitory rTMS to the left TPJ versus sham | Increased connectivity between the left TPJ and the right insula | Performed in patients with schizophrenia and auditory hallucinations | Vercammen et al. (2010b) |
| Resting state fcMRI | Inhibitory rTMS to the left DLPFC versus sham stimulation | Decreased connectivity between the DMN and lateral temporal cortices; trend towards decreased connectivity with the hippocampus. | | van der Werf et al. (2010) |
| Resting state fcMRI | Excitatory and Inhibitory rTMS to the left inferior parietal lobule | Excitatory: Decreased connectivity within the DMN Inhibitory; Increased connectivity with hippocampus | | Eldaief et al. (2011) |

The original studies of paired associative stimulation dealt not with cortical-cortical connections, but connections between cortex and peripheral nerve (Stefan et al., 2000; Wolters et al., 2003). If stimuli to the median nerve and motor cortex are paired with an ISI of 25 ms (such that they arrive nearly simultaneously at the motor cortex) a phenomenon similar to long-term potentiation occurs. A subsequent TMS pulse to the motor cortex will result in a larger motor evoked potential in median innervated muscles suggesting that the connection strength has been increased. If the ISI is changed to 10 ms (such that there is an offset of 15 ms at the motor cortex) a phenomenon similar to long-term depression occurs and subsequent MEPs will be decreased. Derivations of this technique have used endogenous motor activity rather than median nerve stimulation (Thabit et al., 2010) or timed stimuli to arrive with specific offsets in the spinal cord rather than the motor cortex (Cortes et al., 2011) with similar effects. However, the most pertinent derivation of this technique for the present discussion is the use of paired associative stimulation to specifically modulate corticocortical connections (Buch et al., 2011; Plewnia et al., 2008; Rizzo et al., 2009).

In the first paper to use this approach, two TMS coils were used to apply simultaneous 10 Hz stimulation to both the left primary motor cortex and the visual cortex at the occipital pole, with the goal of enhancing polysynaptic connectivity between the two regions (Plewnia et al., 2008). An increase in EEG coherence was seen specifically on the stimulated side that was not seen with M1 stimulation alone. While provocative, this study did not vary the timing of the stimuli to show specificity to simultaneous stimulation versus independent effects of rTMS at the two sites. A subsequent study applied single pulses to the left then right motor cortices at a delay of 8 ms. and frequency of 1 Hz (Rizzo et al., 2009). Following 90 of these paired pulses, but only at this specific delay, there was a marked reduction in inter-hemispheric inhibition. While solidifying the importance of timing, it remains unclear why this study resulted in a decrease rather than an increase in connectivity. Finally, in perhaps the clearest example of this approach, paired associative stimulation was used to modulate connectivity strength between the ventral premotor cortex and M1 (Buch et al., 2011). Applying pulses first to ventral premotor cortex followed by M1 at an appropriate delay led to an increase in the connection strength between these two regions. The effect was anatomically specific and reversing the order of the paired stimuli led to a reversal of the effect (i.e. a decrease in connectivity). Particularly promising for improving the duration of therapeutic TMS, residual effects on connectivity could be seen up to 3 h after the stimulation (Buch et al., 2011). Although currently limited to TMS accessible sites on the cortical surface, the technique of cortico-cortical paired associate stimulation shows great promise for selectively increasing or decreasing connectivity between specific brain regions. Future work is needed to determine if this approach can lead to behavioral manifestations and whether it will be useful for modifying connectivity abnormalities observed with resting state fcMRI in neuropsychiatric disorders in order to promote symptomatic relief.

Conclusions

TMS and resting state fcMRI are complimentary approaches for assessing brain connectivity that can be combined. Areas of particular value include using connectivity to guide TMS target selection and using TMS to modulate abnormal network interactions identified with resting state fcMRI. Together, they provide insight into a variety of interesting neuroscience questions, and provide a reliable, noninvasive method for controlled, individualized neural network modulation.

References

Ahdab, R., Ayache, S. S., 2010. Comparison of "standard" and "navigated" procedures of TMS coil positioning over motor, premotor and prefrontal targets in patients with chronic pain and depression. Neurophysiol. Clin. (Clin. Neurophysiol.) 40, 27-36.

Albert, N. B., Robertson, E. M., et al., 2009. The resting human brain and motor learning. Curr. Biol. 19 (12), 1023-1027.

Anderson, J. S., Druzgal, T. J., Lopez-Larson, M., Jeong, E. N., Desai, I C, Yurgelun-Todd, D., 2011. Network anti-correlations, global regression, and phase-shifted soft tissue correction. Hum. Brain Mapp. 32, 919-934.

Arfanakis, K., Cordes, D., et al., 2000. Combining independent component analysis and correlation analysis to probe interregional connectivity in flVIRI task activation datasets. Magn. Reson. Imaging 18, 921-930.

Assaf, Y., Pasternak, 0., 2008. Diffusion tensor imaging (DTI)-based white matter mapping in brain research: a review, J. Mel. Neurosci. 34 (1), 51-61.

Baldassarre, A., Lewis, C. M., et al., 2012. Individual variability in functional connectivity predicts performance of a perceptual task. Proc. Natl. Acad. Sci. U.S.A. 109 (9), 3516-3521.

Bartels, A., Zeki, S., 2005. Brain dynamics during natural viewing conditions—a new guide for mapping connectivity in vivo. Neuroimage 24, 339-349.

Bestmann, S., Ruff, C C., et al., 2008. Mapping causal interregional influences with concurrent TMS-IMRI. Exp. Brain Res. 191 (4), 383-402.

Bien, N., Roebroeck, A., 2009. The brain's intention to imitate: the neurobiology of intentional versus automatic imitation, Cereb. Cortex (New York, N.Y.: 1991) 19, 2338-2351.

Biswal, B., Yetkin, F., et al., 1995, Functional connectivity in the motor cortex of resting human brain using echo-planar MRI. Magn. Reson. Med. 34, 537-541.

Bluhm, R. L. Miller, j., et al., 2007. Spontaneous low-frequency fluctuations in the BOLD signal in schizophrenic patients: anomalies it's the default network. Schizophr. Bull. 33 (4), 1004-1012.

Brunholzl, C., Claus, D., 1994, Central motor conduction time to upper and lower limbs in cervical cord lesions. Arch. Neurol. 51 (3), 245-249.

Buch, E. R., Johnen, V. M, et al, 2011. Noninvasive associative plasticity induction in a corticocortical pathway of the human brain. J. Neurosci. Off. J. Soc. Neurosci. 31 (48), 17669-17679.

Buckner, R. L., Snyder. A. Z., et al., 2005, Molecular, structural. and functional characterization of Alzheimer's disease: evidence for a relationship between default activity, amyloid, and memory. J. Neurosci. 25 (34), 7709-7717.

Burt. T., Lisanby, S.1-1., et al., 2002. Neuropsychiatric applications of transcranial magnetic stimulation: a meta analysis. Int. J. Neuropsychopharmacol. 5 (1), 73-103.

Bystritsky, A., Korb, A. S., et al., 2011. A review of tow-intensity focused ultrasound pulsation. Brain Stirnul. 4 (3), 125-136.

Carter. A. R., Astafiev, S. V., et al., 2010. Resting interhemispheric functional magnetic resonance imaging connectivity predicts performance after stroke. Ann. Neurol. 67 (3), 365-375.

Chang, C., Glover, G. H., 2009. Effects of model-based physiological noise correction on default mode network anti-correlations and correlations. Neuroimage 47, 1448-1459, Chen, W. H., Mima, T., et al, 2003, Low-frequency rTMS over lateral premotor cortex in¬ duces lasting changes in regional activation and functional coupling of cortical motor areas, Clin. Neurophystol, Off, J. tat. Fed. Clin. Neurophysiol. 114(9), 1628-1637.

Cho, S. S., Strafella, A. P., 2009, rTMS of the left dorsolaterat prefrontal cortex modulates dopamine release in the ipsilateral anterior cingulate cortex and orbitofrontal cortex. PLoS One 4, e6725.

Civardi, C., Cantello, R., et al., 2001. Transcranial magnetic stimulation can be used to test connections to primary motor areas from frontal and medial cortex in humans, Neuroimage 14 (6), 1444-1453.

Corbetta, M., Kincade, M. J., et al., 2005, Neural basis and recovery of spatial attention deficits in spatial neglect. Nat, Neurosci. 8 (11), 1603-1610.

Cordes, D., Naughton, V. M., et al., 2000. Mapping functionally related regions of brain with functional connectivity MR imaging. Am. J. Neuroradiol. 21, 1636-1644.

Cortes, M., Thickbroom, G M., Valls-Sole, J., Pascual-Leone, A., Edwards, D. J., 2011. Spinal associative stimulation: a non-invasive stimulation paradigm to modulate spinal excitability. Clin. Neurophysiol. Off. J, Int. Fed. Clin, Neurophysiol. 122, 2254-2259.

Craddock, R. C., Holtzheimer III P. E., et al., 2009. Disease state prediction from resting state functional connectivity. Magn. Reson. Med. 62 (6), 1619-1628.

Davare, M., Rothwell, J. C, et al., 2010. Causal connectivity between the human anterior intraparietal area and premotor cortex during grasp. Curr. Biol. 20 (2), 176-181.

de Graaf, T. A., Jacobs, C., et al., 2009. FMRI effective connectivity and TMS chronometry: complementary accounts of causality in the visuospatial judgment network. PLoS One 4 (12), e8307.

De Luca, M., Smith, S. M., et al., 2005. Blood oxygenation level dependent contrast resting state networks are relevant to functional activity in the neocortical sensorimotor system. Exp. Brain Res, 167, 587-594.

De Luca, M., Beckmann, C. F., et al., 2006, fMRI resting state networks define distinct modes of long-distance interactions in the human brain. Neuroimage 29 (4), 1359-1367.

Deco, G., Jirsa, V. N. et al., 2011. Emerging concepts for the dynamical organization of resting-state activity in the brain. Nat, Rev. Neurosci. 12 (1), 43-56.

Deng, Z. D., Peterchey, A. V., 2008. Coil design considerations for deep-brain transcranial magnetic stimulation (dIMS). Conf Proc IEEE Eng. Med. Biol. Soc., pp. 5675-5679.

Dosenbach, N. U., Fair, D. A., 2007. Distinct brain networks for adaptive and stable task control in humans, P.N.A.S. 104(26), 11073-11078.

Dosenbach, N. U. F., Nardos, B., et al., 2010. Prediction of individual brain maturity using fMRI. Science 329, 1358-1361.

Drevets, W. C., Savitz. J., et al., 2008. The subgenual anterior cingulate cortex in mood disorders. CNS Spectr. 13, 663-681.

Duque, J., Hummel, F., et al., 2005, Transcallosal inhibition in chronic subcortical stroke. Neuroimage 28 (4). 940-946.

Eldaief, M. C., Halko, M. A. et al., 2011. Transcranial magnetic stimulation modulates the brain's intrinsic activity in a frequency-dependent manner, Proc. Natl. Acad. Sci, U.S.A. 108 (52), 21229-21234.

Engel, A. K., Fries, P., et al., 2001. Dynamic predictions: oscillations and synchrony in top-down processing. Nat. Rev. Neurosci. 2, 704-716.

Fair, D. A., Dosenbach, N. U., Church, J. A., Cohen, A. L., Brahmbhatt, S., Miezin, F. M., Batch, D. M., Raichle, M. E., Petersen, S. E., Schlaggar, B. L., 2007. Development of distinct control networks through segregation and integration. Proc. Natl. Acad. Sci, U.S.A. 104.13507-13512.

Ferbert, A., Priori, A., et al., 1992. Interhemispheric inhibition of the human motor cortex, J. Physiol, 453, 525-546.

Ferrarelli, F., Haraldsson, H. M. et al., 2004. A 117F1-fluoromethane PET/TMS study of effective connectivity. Brain Res. Bull. 64 (2), 103-113.

Ferrarelli, F., Massimini, M., et al. 2010. Breakdown in cortical effective connectivity during midazolam-induced loss of consciousness. Proc. Natl. Acad. Sci. U.S.A. 107 (6), 2681-2686

Ferreri, F., Pasqualetti, P., Maatta, S., Ponzo, D., Ferrarelli, F., Tononi, G., Mervaala, E., Miniussi, C., Rossini, P. M., 2011. Human brain connectivity during single and paired pulse transcranial magnetic stimulation. Neuroimage 54, 90-102.

Fitzgerald, P. B., Hoy, K., et al., 2009. A randomized trial of rTMS targeted with MRI based neuro-navigation in treatment-resistant depression. Neuropsychopharma-cology 34 (5), 1255-1262.

Floyd, A. G., Yu, Q. P., et al., 2009. Transcranial magnetic stimulation in ALS: utility of central motor conduction tests. Neurology 72 (6), 498-504.

Fox, M. D., Greicius, M., 2010. Clinical applications of resting state functional connectivity, Front. Syst, Neurosci. 4.19.

Fox, M. D., Raichle, M. E., 2007. Spontaneous fluctuations in brain activity observed with functional magnetic resonance imaging. Nat Rev. Neurosci. 8 (9), 700-711.

Fox, P., Ingham, R., et al. 1997, Imaging human intracerebral connectivity by PET during TMS. Neuroreport 8 (12), 2787-2791.

Fox, M. D., Snyder, A. Z., et al., 2005. The human brain is intrinsically organized into dynamic, anticorrelated functional networks, P.N.A.S. 102 (27), 9673-9678.

Fox, M. D., Corbetta, M., Snyder, A. Z., Vincent, J. L., Raichle, M. E., 2006. Spontaneous neuronal activity distinguishes human dorsal and ventral attention systems. P.N.A.S. 103, 10046-10051.

Fox, M. D., Snyder, A., Zacks, J. M., Raichle, M. E., 2006. Coherent spontaneous activity accounts for trial-to-trial variability in human evoked brain responses. Nat. Neurosci. 9, 23-25.

Fox, R., Narayana, S., Tandon, N., Fox, S. P., Sandoval, Kochunov, P., Capaday, C., Lancaster, J. L., 2006. Intensity modulation of TMS-induced cortical excitation: primary motor cortex. Hum. Brain Mapp. 27, 478-487.

Fox, M. D., Snyder, A. Z., et al., 2007. Intrinsic fluctuations within cortical systems account for intertrial variability in human behavior. Neuron 56 (1), 171-184.

Fox, M. D, Zhang, D, et al., 2009a, The global signal and observed anticorrelated resting state brain networks. J. Neurophysiol. 101 (6), 3270-3283, Fox, M. D., Buckner, R. L., et al., 2012. Intrinsic functional connectivity with the subgenual cingulate predicts clinical efficacy of TMS targets for depression. American Academy of Neurology Annual Meeting, New Orleans.

Fransson, P., 2005. Spontaneous low-frequency BOLD signal fluctuations: an fMRI investigation of the resting-state default mode of brain function hypothesis. Hum. Brain Mapp. 26 (1), 15-29, Fransson, P. 2006. How default is the default mode of brain function? Further evidence from intrinsic BOLD signal fluctuations. Neuropsychologia 44 (14), 2836-2845.

Fregni, F., Pascual-Leone, A., 2007. Technology insight: noninvasive brain stimulation in neurology-perspectives on the therapeutic potential of rTMS and tDCS. Nat. Clin. Pract. Neurol. 3 (7), 383-393.

Freitas, C., Fregni, F, et al, 2009. Meta-analysis of the effects of repetitive transcranial magnetic stimulation (rTMS) on negative and positive symptoms in schizophrenia. Schizophr. Res. 108 (1-3), 11-24.

Friston, N. J., Frith, C. D., et al., 1993. Functional connectivity: the principal component analysis of large (PET) data sets. J. Cereb. Blood Flow Metab, 13, 5-14, Fuggetta, G., Pavone, E. F. et al., 2008. Acute modulation of cortical oscillatory activities during short trains of high-frequency repetitive transcranial magnetic stimulation of the human motor cortex: a combined EEG and TMS study. Hum, Brain Mapp. 29 (1), 1-13.

Fukunaga, M., Horovitz, S. G., et al, 2006, Large-amplitude, spatially correlated fluctuations in BOLD fMRI signals during extended rest and light sleep. Magn. Reson. Imaging 24, 979-992.

Garcia-Toro, M., Salva, J., et al., 2006. High (20-Hz) and low (1-Hz) frequency transcranial magnetic stimulation as adjuvant treatment in medication-resistant depression. Psychiatry Res. 146 (1), 53-57.

George, M S., Wassermann, E. M., et al., 1996. Changes in mood and hormone levels after rapid-rate transcranial magnetic stimulation (rTMS) of the prefrontal cortex. J. Neuropsychiatry Clin, Neurosci. 8 (2), 172-180.

George, M S., Stallings, L E, et al., 1999. Prefrontal repetitive transcranial magnetic stimulation (CMS) changes relative perfusion locally and remotely. Hum. Psycho-pharmacol. Clin. Exp. 14, 161-170.

Gorsler, A., Baumer, T. et al., 2003. Interhemispheric effects of high and low frequency rTMS in healthy humans. Olin. Neurophysiol, 114 (10), 1800-1807.

Grefkes, C., Nowak, D. A., et al., 2008. Cortical connectivity after subcortical stroke assessed with functional magnetic resonance imaging. Ann. Neurol. 63 (2), 236-246.

Grefkes, C., Nowak, D. A., et al., 2010. Modulating cortical connectivity in stroke patients by rTMS assessed with fMRI and dynamic causal modeling. Neuroimage 50 (1), 233-242.

Greicius, M., 2008, Resting-slate functional connectivity in neuropsychiatric disorders. Curt. Opin. Neural. 21 (4), 424-430.

Greicius, M. D., Flores, B. H., Menai, V., Glover, G. H., Solvason, H. B., Kenna, H., Reiss, Al., Schatzberg, A. F., 2007. Resting-state functional connectivity in major depression: abnormally increased contributions from subgenual cingulate cortex and thalamus. Biol, Psychiatry 62, 429-437.

Greicius, M. D., Krasnow, B., et al., 2003. Functional connectivity in the resting brain: a network analysis of the default mode hypothesis. Proc. Natl. Acad. Sci. U.S.A. 100, 253-258.

Greicius, M. D., Srivastava, G., et al., 2004. Default-mode network activity distinguishes Alzheimer's disease from healthy aging: evidence from functional MRI. Proc. Natl. Acad. Sci. U.S.A. 101, 4637-4642.

Greicius, M. D., Kiviniemi, V. et al., 2008. Persistent default-mode network connectivity during light sedation. Hum. Brain Mapp. 29 (7), 839-847, Greicius, M. D, Supekar, K., et al., 2009. Resting-state functional connectivity reflects structural connectivity in the default mode network. Cereb. Cortex (New York, N.Y.: 1991) 19, 72-78.

Gugino, L. D, 'Romero, J. R., et al., 2001. Transcranial magnetic stimulation coregistered with MRI: a comparison of a guided versus blind stimulation technique and its effect on evoked compound muscle action potentials. Chin. Neurophysiol. 112 (10), 1781-1792.

Hallett, M, 2007, Transcranial magnetic stimulation: a primer. Neuron 55 (2), 187-199.

Hampton, M., Hoffman, E., 2010, Transcranial magnetic stimulation and connectivity mapping: tools for studying the neural bases of brain disorders. Front, Syst. Neurosci. 4, 1-8.

Hampton, M., Peterson, B. S., et al., 2002. Detection of functional connectivity using temporal correlations in MR images. Hum, Brain Mapp. 15, 247-262.

Hampton, M., Olson, R., et al., 2004. Changes in functional connectivity of human MT/V5 with visual motion input. Neuroreport 15, 1315-1319.

Hampton, M., Driesen, H. R., et al., 2006. Brain connectivity related to working memory performance. J. Neurosci. 26 (51), 13338-13343.

Hanajima, R., Ugawa, Y., et al., 2001. Interhemispheric facilitation of the hand motor area in humans. J. Physiol. 531 (Pt 3), 849-859.

Hannula, H., Neuvonen, T., et al., 2010. Increasing top-down suppression from prefrontal cortex facilitates tactile working memory. Neuroimage 49, 1091-1098.

He, B. J., Snyder, A. Z., et al., 2007. Breakdown of functional connectivity in frontoparietal networks underlies behavioral deficits in spatial neglect. Neuron 53 (6), 905-918.

Herbsman, T., Avery, D., et al., 2009. More lateral and anterior prefrontal coil location is associated with better repetitive transcranial magnetic stimulation antidepressant response. Biol. Psychiatry 66 (5), 509-515.

Herwig, U., Padberg, F., et al., 2001. Transcranial magnetic stimulation in therapy studies: examination of the reliability of "standard" coil positioning by neuronavigation. Biol. Psychiatry 50 (1), 58-61, Herwig, U., Lampe, Y., et al., 2003, Add-on rTMS for treatment of depression: a pilot study using stereotaxic coil-navigation according to PET data. J. Psychiatr. Res, 37 (4), 267-275.

Hess, C. W., Mills, K. R, et al, 1986, Measurement of central motor conduction in multiple sclerosis by magnetic brain stimulation. Lancet 2 (8503), 355-358.

Hoffman, R E., Hampton, M., et al., 2007. Probing the pathophysiology of auditory/verbal hallucinations by combining functional magnetic resonance imaging and transcranial magnetic stimulation. Cereb. Cortex 17 (11), 2733-2743, Honey, C. I., Sporns, O., Cammoun, L., Gigandet, X., Thiran, J. P., Meuli, R., Hagmann, P., 2009. Predicting human resting-state functional connectivity from structural connectivity, Proc. Natl. Acad. Sci. USA 106, 2035-2040.

Horacek, J., Brunovsky, M., et al., 2007. Effect of low-frequency rTMS on electromagnetic tomography (LORETA) and regional brain metabolism (PET) in schizophrenia patients with auditory hallucinations. Neuropsychobiology 55 (3-4), 132-142, Horovitz, S. G., Braun, A. R., et al., 2009, Decoupling of the brain's default mode network during deep sleep. Proc. Natl. Acad. Sci. U.S.A. 106 (27), 11376-11381, Horwitz, B., 2003. The elusive concept of brain connectivity. Neuroimage 19, 466-470.

Ilmoniemi, R. J., Virtanen, J., et al., 1997. Neuronal responses to magnetic stimulation reveal cortical reactivity and connectivity. Neuroreport 8 (16), 3537-3540.

Jiang, T., He, Y., et al., 2004. Modulation of functional connectivity during the resting state and the motor task. Hum. Brain Mapp. 22, 03-71.

Jing, H., Takigawa, M., 2000. Observation of EEG coherence after repetitive transcranial magnetic stimulation. Clin. Neurophysiol. 111 (9), 1620-1631.

Johnston, J. M., Vaistmavi, S. N., et al., 2008. Loss of resting interhemispheric functional connectivity after complete section of the corpus callosum. J. Neurosci. 28 (25), 6453-6458.

Kiviniemi, V, Kantola, J. H, et al., 2003. Independent component analysis of nondeterministic fMRI signal sources. Neuroimage 19, 253-260.

Kobayashi, M., Pascual-Leone, A., 2003. Transcranial magnetic stimulation in neurology, Lancet Neurol. 2 (3), 145-156.

Koch, G., Rothwell, J. C., 2009. TMS investigations into the task-dependent functional interplay between human posterior parietal and motor cortex. Behav. Brain Res. 202, 147-152.

Koch, M. A., Norris, D. G., et al., 2002. An investigation of functional and anatomical connectivity using magnetic resonance imaging. Neuroimage 16, 241-250.

Koch, G., Franca, M., et al., 2006. Time course of functional connectivity between dorsal premotor and contralateral motor cortex during movement selection. J. Neurosci. 26 (28), 7452-7459.

Koyama, M. S., Di Martino, A., et al., 2011. Resting-state functional connectivity indexes reading competence in children and adults, J. Neurosci, Off. J. Soc. Neurosci, 31 (23), 8617-8624.

Larson-Prior, L. J., Zempel, J. M, et al., 2009. Cortical network functional connectivity in the descent to sleep. Proc. Natl. Acad. Sci. U.S.A. 106 (11), 4489-4494.

Lee, L., Siebner, H. R., et al., 2003. Acute remapping within the motor system induced by low-frequency repetitive transcranial magnetic stimulation. J. Neurosci. 23 (12), 5308-5318.

Lewis, C. M., Baldassarre, A., et al., 2009. Learning sculpts the spontaneous activity of the resting human brain. Proc., Nat., Acad. Sci., USA. 106 (41), 17558-17563.

Li, S. J., Li, Z., et al., 2002. Alzheimer disease: evaluation of a functional MR imaging index as a marker. Radiology 225 (1), 253-259.

Li, X., Nahas, Z., et al., 2004. Acute left prefrontal transcranial magnetic stimulation in depressed patients is associated with immediately increased activity in prefrontal cortical as well as subcortical regions. Biol. Psychiatry 55, 882-890.

Liu, Y., Yu, C., Liang, M., Li, J., Tian, U, Zhou, Y., Qin W., Li, K., Jiang, I., 2007. Whole brain functional connectivity in the early blind. Brain 130, 2085-2096.

Lowe, M. J., Mock, B J, et al., 1998, Functional connectivity in single and multislice echo planar imaging using resting-state fluctuations, Neuroimage 7, 119-132.

Lowe, M. J. Dzernidzic, M., et al., 2000. Correlations in low-frequency BOLD fluctuations reflect cortico-cortical connections, Neuroimage 12, 582-587.

Lowe, M. J., Beall, E. B., et al., 2008. Resting state sensorimotor functional connectivity in multiple sclerosis inversely correlates with transcallosal motor pathway transverse diffusivity. Hum. Brain Mapp. 29, 818-827.

Marder, E. and J. M. Weimann (1991). Modulatory control of multiple task processing in the stomatogastric nervous system. Neurobiology of Motor Program Selection: New Approaches to Mechanisms of Behavioral Choice. J. Kien, C. McCrohan and B. Winlow. Manchester, U. K., Manchester University Press: 3-19.

Massimini, M., Ferrarelli, F, et al., 2005. Breakdown of cortical effective connectivity during sleep. Science 309 (5744), 2228.-2232.

Mayberg, H. S., 2007. Defining the neural circuitry of depression: toward a new nosology with therapeutic implications. Biol. Psychiatry 61 (6), 729-730.

Mayberg, H. S., 2009. Targeted electrode-based modulation of neural circuits for depression, J. Clin. Invest, 119 (4), 717-725.

Mayberg, H. S., Lozano, A. M., et al., 2005. Deep brain stimulation for treatment-resistant depression. Neuron 45, 651-660.

Meyer, B. U., Roricht, S. et al., 1995. Inhibitory and excitatory interhemispheric transfers between motor cortical areas in normal humans and patients with abnormalities of the corpus callosum. Brain 118 (Pt 2), 429-440.

Morgan, V. L., Price, R. R., 2004. The effect of sensorimotor activation on functional connectivity mapping with fMRI. Magn. Reson. Med. 22, 1069-1075.

Murase, N., Duque, J., et al., 2004, Influence of interhemispheric interactions on motor function in chronic stroke. Ann. Neurol. 55 (3), 400-409.

Murphy, K., Bins, R. M., et al., 2009. The impact of global signal regression on resting state correlations: are anti-correlated networks introduced? Neuroimage 44 (3), 893-905.

Nir, Y., Hasson, U. et al., 2006. Widespread functional connectivity and fMRI fluctuations in human visual cortex in the absence of visual stimulation. Neuroimage 30 (4), 1313-1324.

Oliviero, A., Stress, L H., et al., 2003. Persistent effects of high frequency repetitive TMS on the coupling between motor areas in the human. Exp, Brain Res. 149 (1), 107-113.

O'Shea, J., Johansen-Berg, H., et al., 2007. Functionally specific reorganization in human premotor cortex. Neuron 54 (3), 479-490.

Padberg, F., George, M. S., 2009. Repetitive transcranial magnetic stimulation of the prefrontal cortex in depression. Exp. Neurot. 219 (1), 2-13.

Paillere Martinot, M. L, Galinowski, A, Ringuenet, D., Gallarda, T., Lefaucheur, J. P., Bellivier, F., Picq, C, Bruguiere, P., Mangin, Riviere, D., Willer, J. C., Falissard, Leboyer, M., Olie, J. P., Artiges, Martinot, J. L, 2010. Influence of prefrontal target region on the efficacy of repetitive transcranial magnetic stimulation in patients with medication-resistant depression: a [(18)F]-fluorodeoxyglucose PET and MRI study. Int. J. Neuropsychopharmacol. Off, Sci. J., Collegium Int. Neuropsychopharmacol. 13, 45-59.

Pal, P. K., Hanajima, R., et al., 2005. Effect of low-frequency repetitive transcranial magnetic stimulation on interhemispheric inhibition. J. Neurophysiol, 94 (3), 1668-1675.

Pascual-Leone, A., Walsh, V., 2001. Fast back projections from the motion to the primary visual area necessary for visual awareness, Science 292 (5516), 510-512.

Pascual-Leone, A, Rubio, B., et al., 1996. Rapid-rate transcranial magnetic stimulation of left dorsolateral prefrontal cortex in drug-resistant depression. Lancet 348 (9022), 233-237.

Paus, T., Castro-Alamancos, M A., et al., 2001. Corticocortical connectivity of the human mid-dorsolateral frontal cortex and its modulation by repetitive transcranial magnetic stimulation. Eur. J. Neurosci. 14, 1405-1411.

Pars, T., Jech, R., et al., 1997. Transcranial magnetic stimulation during positron emission tomography: a new method for studying connectivity of the human cerebral cortex. J. Neurosci. 17 (9), 3178-3184.

Peltier, S. J., Kerssens, C., et al., 2005. Functional connectivity changes with concentration of sevoflurane anaesthesia. Neuroreport 16 (3), 285-288.

Petrides, M., Pandya, D. N., 1999. Dorsolateral prefrontal cortex: comparative cytoarchitectonic analysis in the human and the macaque brain and corticocortical connection patterns. Eur. J. Neurosci, 11, 1011-1036.

Blankenburg, F., et al., 2006. Repetitive transcranial magnetic stimulation-induced changes in sensorimotor coupling parallel improvements of somatosensation in humans. J. Neurosci. 26 (7), 1945-1952.

Plewnia, C., Rilk, A. J., et al., 2008. Enhancement of long-range EEG coherence by synchronous bifocal transcranial magnetic stimulation. Eur. J. Neurosci. 27 (6), 1577-1583.

Reithler, I., Peters, J. C., 2011. Multimodal transcranial magnetic stimulation: using concurrent neuroimaging to reveal the neural network dynamics of noninvasive brain stimulation. Prog, Neurobiol. 1-17.

Rizzo, V., Siebner, H. S., et al., 2009. Paired associative stimulation of left and right human motor cortex shapes interhemispheric motor inhibition based on a Hebbian mechanism. Cereb. Cortex 19 (4), 907-915.

Roebroeck, A., Formisano, E., et al., 2005. Mapping directed influence over the brain using Granger causality and fMRI. Neuroimage 25 (1), 230-242.

Rogers, B. P., Morgan, V. L., Newton, A. T., Gore, J. C., 2007. Assessing functional connectivity in the human brain by fMRI. Magn. Reson. Imaging 25, 1347-1357.

Rossi, S., Hallett, M., et al., 2009. Safety, ethical considerations, and application guidelines for the use of transcranial magnetic stimulation in clinical practice and research. Clin. Neurophysiol. 120 (12), 2008-2039.

Roth, Y., Amir, A., et al., 2007. Three-dimensional distribution of the electric field induced in the brain by transcranial magnetic stimulation using figure-8 and deep H-coils, J. Clin. Neurophysiol. 24 (1), 31-38.

Ruff, C. C., Blankenburg, F. et al., 2006. Concurrent TMS-fMRI and psychophysics reveal frontal influences on human retinotopic visual cortex, Curr. Biol. 16 (15), 1479-1488.

Ruff, C. C., Driver, J., el al., 2009: Combining TMS and (MRI: from 'virtual lesions' to functional-network accounts of cognition. Cortex 45 (9), 1043-1049.

Sack, A. T., Cohen Kadosh, R., et al., 2009. Optimizing functional accuracy of TMS in cognitive studies: a comparison of methods. J. Cogn. Neurosci. 21 (2), 207-221.

Sadaghiani, S., Hesselmann, G., et at, 2010. The relation of ongoing brain activity, evoked neural responses, and cognition. Front. Syst. Neurosci. 4, 20.

Seeley, W. W., Meson; V., et al., 2007, Dissociable intrinsic connectivity networks for salience processing and executive control. J, Neurosci, 27 (9), 2349-2356.

Siebner, H. R., Petler, M, et al., 2000. Lasting cortical activation after repetitive TMS of the motor cortex: a glucose metabolic study. Neurology 54 (4), 956-963.

Siebner, H. R., Bergmann, T. O., et al., 2002 Consensus paper: combining transcranial stimulation with neuroimaging. Brain Stimul, 2 (2), 58-80.

Silvanto, J., Cowey, A., et al., 2005. Striate cortex (V1) activity gates awareness of motion. Nat. Neurosci. 8 (2), 143-144.

Silvanto, J., Lavie, N., et al., 2006. Stimulation of the human frontal eye fields modulates sensitivity of extrastriate visual cortex. J. Neurophysiol. 96 (2), 941-945.

Silvanto, J., Muggleton, N., et al., 2009. The perceptual and functional consequences of parietal top-down modulation on the visual cortex. Cereb. Cortex 19 (2), 327-330.

Skudlarski, P. Jagannathan, K., el. al., 2008. Measuring brain connectivity: diffusion tensor imaging validates resting state temporal correlations. Neuroimage 43 (3), 554-561.

Stefan, K., Kunesch, E., et al., 2000. Induction of plasticity in the human motor cortex by paired associative stimulation. Brain 123 (Pt 3), 572-584.

Stephan, K. E., Friston, K. J, 2010. Analyzing effective connectivity with fMRI. Wiley Interdiscip, Rev. Cogn. Sci. 1 (3), 446-459.

Strens, L H., Oliviero, A., et al., 2002. The effects of subthreshold 1 Hz repetitive TMS on cortico-cortical and interhemispheric coherence. Chin. Neurophysiol. 113 (8), 1279-1285.

Sun, F. T., Miller, L. M., et al., 2006. Functional connectivity of cortical networks involved in bimanual motor sequence learning, Cereb. Cortex 17 (5), 1227-1234.

Supekar, K., Meson, V., et al., 2008, Network analysis of intrinsic functional brain connectivity in Alzheimer's disease. PLoS Comput. Biol. 4 (6), e1000100.

Tambini, A., Ketz, N, et al, 2010, Enhanced brain correlations during rest are related to memory for recent experiences. Neuron 65 (2), 280-290.

Thabit, M. N., Ueld, Y., et al., 2010. Movement-related cortical stimulation can induce human motor plasticity. J. Neurosci. Oft J. Soc. Neurosci. 30 (34), 11529-11536.

Thut, G., Pascual-Leone, A., 2010. A review of combined TMS-EEG studies to characterize lasting effects of repetitive TMS and assess their usefulness in cognitive and clinical neuroscience. Brain Topogr. 22 (4), 219-232.

Ugawa, Y., Day, B. L, et al., 1991. Modulation of motor cortical excitability by electrical stimulation over the cerebellum in man. J. Physiol. 441, 57-72.

Valero-Cabre, A., Payne, B. R. et al., 2005. Impact of repetitive transcranial magnetic stimulation of the parietal cortex on metabolic brain activity: a 14C-2DG tracing study in the cat. Exp. Brain Res. 163 (1), 1-12.

Valero-Cabre, A., Payne, B. R., et al, 2007: Opposite impact on 14C-2-deoxyglucose brain metabolism following patterns of high and low frequency repetitive transcranial magnetic stimulation in the posterior parietal cortex. Exp. Brain Res. 176 (4), 603-615.

van den Heuvel, M. P., Hulshoff Pol, H. E., 2010. Exploring the brain network: a review on resting-state fMRI functional connectivity. Eur. Neuropsychopharmacol. 20 (8), 519-534.

van den Heuvel, M., Mandl, R., et al., 2008. Microstructural organization of the cingulum tract and the level of default mode functional connectivity. J. Neurosci, 28 (43), 10844-10851.

van den Heuvel, M. P., Mandl, R. C., Kahn, R. S., Hulshoff Pol, H. E., 2009a. Functionally linked resting-state networks reflect the underlying structural connectivity architecture of the human brain. Hum. Brain Mapp, 30, 3127-3141.

van den Heuvel, M. P., Siam, C. J., Kahn, R. S., Hulshoff Pol, H. E., 2009b, Efficiency of functional brain networks and intellectual performance, J. Neurosci. Off. J. Soc. Neurosci. 29, 7619-7624.

van der Werf, Y. D., Sanz-Arigita, E. J., et al., 2010. Modulating spontaneous brain activity using repetitive transcranial magnetic stimulation. BMC Neurosci. 11, 145.

Varella, F., Lachaux, J.-P., et al., 2001. The brainweb: phase synchronization and large-scale integration. Nat. Rev. Neurosci, 2, 229-239.

Vercammen, A., Knegtering, H., den Boer, J. A., Liemburg, E. J., Aleman, A., 2010a. Auditory hallucinations in schizophrenia are associated with reduced functional connectivity of the temporo-parietal area. Biol. Psychiatry 67, 912-918.

Vercammen, A., Knegtering, H., Liemburg, E. J., den Boer, J. A., Aleman, A., 2010b, Functional connectivity of the temporo-parietal region in schizophrenia: effects of rTMS treatment of auditory hallucinations. J. Psychiatr. Res. 44, 725-731.

Vincent, J. L., Snyder, A. Z., et al., 2006. Coherent spontaneous activity identifies a hippo-campal-parietal mnemonic network. J. Neurophysiol. 96 (6), 3517-3531.

Vincent, J. L, Patel, G. H., Fox, M. D., Snyder, A. Z., Baker, J. T., Van Essen, D. C., Zempel, J. M., Snyder, L. H., Corbetta, M., Raichle, M. E., 2007. Intrinsic functional architecture in the anaesthetized monkey brain. Nature 447, 83-86, Vogt, B. A., Pandya, D. N., 1987. Cingulate cortex of the rhesus monkey: II. Cortical afferents. J. Comp. Neurol. 262, 271-289.

Voineskos, A. N., Farzan, F., et al., 2010. The role of the corpus callosum in transcranial magnetic stimulation induced interhemispheric signal propagation. Biol. Psychiatry 68, 825-831.

Wagner, T., Valero-Cabre, A., et al., 2007, Noninvasive human brain stimulation, Annu. Rev, Biomed. Eng. 9, 527-565.

Wahl, M., Lanterbach-Soon, B., et al., 2007. Human motor corpus callosum: topography, somatotopy, and link between microstructure and function. J. Neurosci. 27 (45). 12132-12138.

Wahl, M., Hubers, A., et al., 2011. Motor callosal disconnection in early relapsing-remitting multiple sclerosis. Hum. Brain Mapp. 32 (6), 846-855.

Wang, K., Jiang, T, Liang, M., Wang, L, Tian, L, Zhang, X, Li, K., Liu, Z., 2006. Discriminative analysis of early Alzheimer's disease based on two intrinsically anti-correlated networks with resting-state fMRI. Med. Image Comput, Comput. Assist. Interv. Int. Conf. Med. Image Comput. Comput. Assist. Interv., 9, 340-347.

Whitfield-Gabrieli, S., Thermenos, H. W., et al., 2009, Hyperactivity and hyperconnectivity of the default network in schizophrenia and in first-degree relatives of persons with schizophrenia. Proc. Natl. Acad. Sci. U.S.A. 106 (4), 1279-1284.

Wittenberg, G. F., Werhahn, K. J., et al., 2004. Functional connectivity between somatosensory and visual cortex in early blind humans. Eur. J. Neurosci. 20 (7), 1923-1927.

Wolters. A., Sandbrink, F., et al., 2003. A temporally asymmetric Hebbian rule governing plasticity in the human motor cortex. J. Neurophysiol. 89 (5), 2339-2345.

Yu, C., Liu, Y., et al., 2008. Altered functional connectivity of primary visual cortex in early blindness. Hum. Brain Mapp. 29 (5), 533-543.

Zanto, T. P., Rubens, M. T., et al., 2011, Causal role of the prefrontal cortex in top-down modulation of visual processing and working memory. Nat. Neurosci. 14 (5), 656-661.

Zhang, D., Raichle, M. E., 2010. Disease and the brain's dark energy. Nat, Rev. Neural. 6, 15-28.

Zhang, D., Snyder, A. Z., et al., 2010. Noninvasive functional and structural connectivity mapping of the human thalamocortical system. Cereb. Cortex 20 (5), 1187-1194.

Zhu, Q., Zhang, J., et al., 2011. Resting-state neural activity across face-selective cortical regions is behaviorally relevant. J. Neurosci. Off. J. Soc. Neurosci. 31 (28), 10323-10330.

EXAMPLE 3

Abstract:

BACKGROUND: Transcranial magnetic stimulation (TMS) to the left dorsal-lateral prefrontal cortex (DLPFC) is used clinically for the treatment of depression. However the antidepressant mechanism remains unknown and its therapeutic efficacy have been limited. Recent data suggests that some left DLPFC targets are more effective than others; the reasons for this heterogeneity and how to capitalize on this information remain are studied.

METHODS: Intrinsic (resting state) fMRI data from 98 normal subjects were used to compute functional connectivity with various left DLPFC TMS targets employed in the literature. Differences in functional connectivity related to differences in previously reported clinical efficacy were identified. This information was translated into a connectivity-based targeting strategy to identify optimized left DLPFC TMS coordinates. Results in normal subjects were tested for reproducibility in an independent cohort of 13 patients with depression.

RESULTS: Differences in functional connectivity were related to previously reported differences in clinical efficacy across a distributed set of cortical and limbic regions. DLPFC TMS sites with better clinical efficacy were more negatively correlated (anticorrelated) with the subgenual cingulate. Optimum connectivity-based stimulation coordinates were identified in BA46. Results were reproducible in patients with depression.

CONCLUSIONS: Reported antidepressant efficacy of different left DLPFC TMS sites is related to the anticorrelation of each site with the subgenual cingulate, potentially lending insight into the antidepressant mechanism of TMS and suggesting a role for intrinsically anticorrelated networks in depression. These results are translated into a connectivity-based targeting strategy for focal brain stimulation that might be used to optimize clinical response.

Introduction:

Transcranial magnetic stimulation (TMS) is a noninvasive technique that utilizes short, rapidly changing magnetic field pulses to induce electrical currents in underlying cortical tissue (for reviews see (1-3)). By applying repeated pulses (rTMS) at low frequencies (e.g. 1 Hz) one can suppress underlying cortical activity and high-frequency stimulation (e.g. 20 Hz) can result in excitatory changes (1-3). Further, the effects of TMS can propagate beyond the site of stimulation, impacting a distributed network of brain regions (4-10).

One of the first clinical uses of TMS and its only FDA-approved therapeutic indication is high-frequency stimulation to the left dorsal lateral prefrontal cortex (DLPFC) for the treatment of medication resistant depression (11-14). Depression involves a distributed network of cortical and limbic regions including the DLPFC (especially the left), hippocampus, and subgenual cingulate among others (15, 16). Of these, the subgenual region has shown some of the most reproducible abnormalities. The subgenual decreases its activity in response to multiple treatment modalities (Table 1) and is a successful target of deep brain stimulation (DBS) (16-18). Unfortunately TMS is largely limited to the cortical surface and deeper limbic regions including the subgenual cannot be directly or selectively stimulated with traditional stimulation cods. TIVIS studies have therefore focused on the left DLPFC as one accessible node of this depression network. It has been hypothesized that left DLPFC TMS might have distributed effects on deeper limbic regions such as the subgenual (12, 13, 19), however combined TMS imaging studies designed to investigate this hypothesis have produced conflicting results (20-34). It therefore remains unclear how TMS to the DLPFC exerts its antidepressant effect.

Paralleling our limited understanding of the antidepressant mechanism of TMS, its therapeutic efficacy, while statistically significant, also remains limited (11-14). One problem known to contribute to limited average clinical efficacy is difficulty identifying the appropriate stimulation target in the left DLPFC (12, 35-38). The FDA approved Neuronetics® Neurostar protocol along with the majority of TMS depression studies identifies the left DLPFC stimulation site by moving 5 cm anterior to the motor cortex along the curvature of the scalp (11-14, 39). However this technique frequently misses the DLPFC (37, 38). Alternative approaches to DLPFC target identification have been examined including standardized EEG electrode positions (40), a variety of anatomical MRI coordinates focused around Brodmann areas 9 and 46 (35, 36, 41), and individualized hypometabolic foci (42-44) (Table 1 B). These alternative targeting strategies have not led to substantial clinical improvements beyond the 5 cm approach, however data from these studies suggests that some DLPFC stimulation sites are more effective than others (12, 35, 36, 42), Unfortunately, it remains unclear why some sites are more effective, and it would be desirable to capitalize on this information to optimize target selection or clinical effect.

In the current example, we hypothesize that previously reported differences in clinical efficacy of different left DLPFC stimulation sites are related to differences in the connectivity of these sites to deeper limbic regions, especially the subgenual cingulate. We tested this hypothesis using intrinsic (resting state) functional connectivity MRI, a powerful imaging technique that utilizes correlations in spontaneous fluctuations in the blood oxygenation level-dependent (BOLD) signal to assess functional relationships between regions (45-47). We first examined a large cohort of normal subjects to detect subtle differences in connectivity between adjacent regions, then confirmed these findings in a smaller cohort of patients with major depressive disorder.

Methods:

Full methodological details can be found in the supplementary material. Two datasets collected at different sites were used in the present analysis. The first consisted of 98 healthy right-handed subjects (48 male, ages 22+3.2 years (mean+SD)). The second dataset consisted of 13 right-handed subjects with major depressive disorder (3 male, mean age 40.2 years, mean HAM-D 23.8) and eleven healthy controls (5 male, mean age 29 years, mean HAM-D 0.4). These cohorts differed in age, gender ratio, and MRI scanner parameters and therefore cannot be directly compared to look for cohort differences; however they can be used to test for reproducibility across cohorts. All subjects completed one or more resting state fcMRI scans. fcMRI data were processed in accordance with the strategy of Fox et al. 2005 (48) as implemented in Van Dijk 2010 (47) including global signal regression. An a-priori region of interest (ROI) was defined in the subgenual cingulate cortex (FIGS. 20A-20B, FIG. 18A) based on coordinates from prior studies showing reductions in subgenual activity tied to antidepressant response (17, 23, 24, 49-52) (Table 1). Additionally, a-priori ROIs were defined in the left DLPFC based on coordinates previously used or proposed as TMS targets for depression (FIG. 16, FIGS. 17A-17F), Table 1) (25, 35-37, 41, 42, 53, 54).

Figure 16:
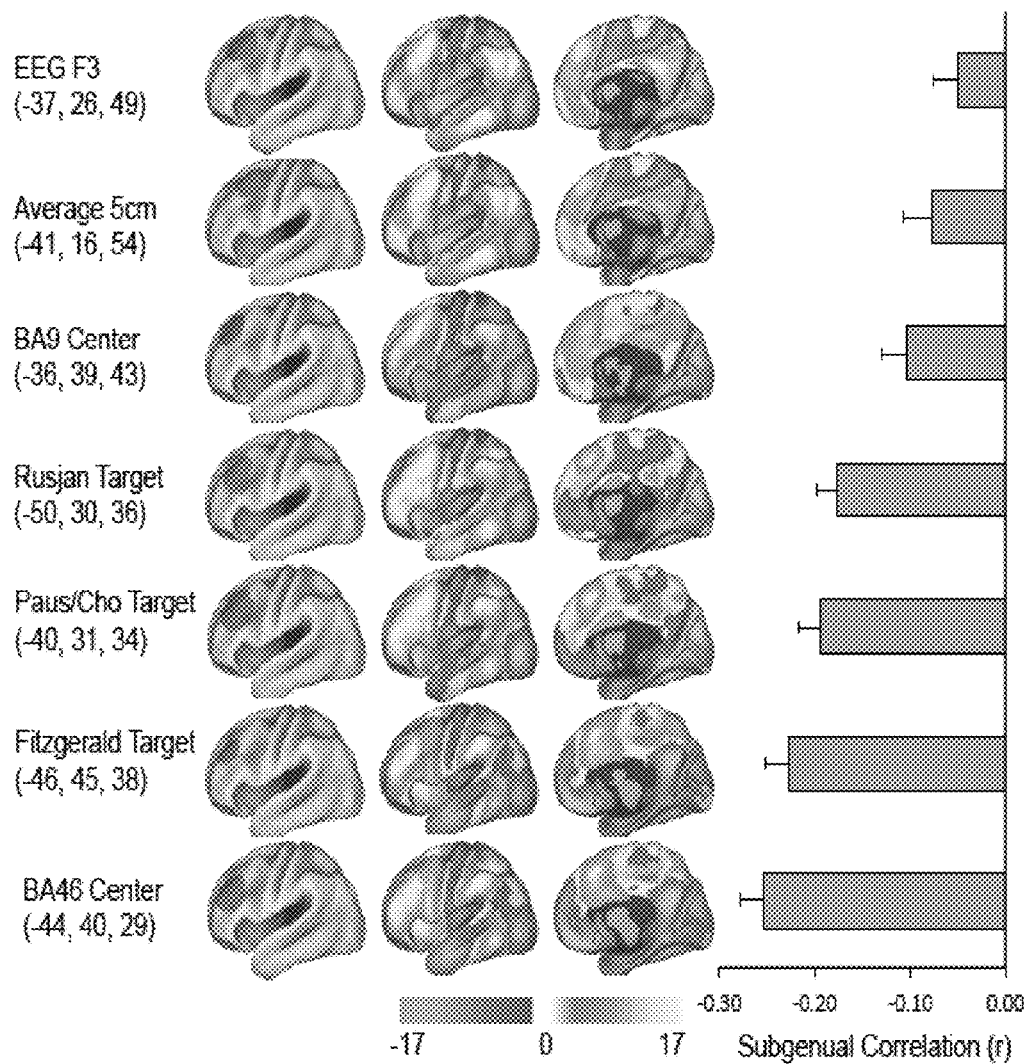
FIG. 16 illustrates different left DLPFC TMS targets show variability in resting state functional connectivity, especially with the subgenual cingulate. The left hand column shows the coordinates and regions of interest for various left DLPFC TMS targets employed in the literature. The middle columns show resting state functional connectivity maps for each DLPFC region of interest. The border of our a-priori defined subgenual region of interest is show for reference. The right hand column is the correlation coefficient between the time course from each DLPFC region of interest and that of the subgenual cingulate.

Results:

We first determined whether the different left DLPFC stimulation sites suggested in the literature showed heterogeneity in their underlying functional connectivity, both on a voxelwise basis and specifically with our a priori defined region of interest in the subgenual cingulate (FIG. 16). Clear differences in functional connectivity were observed across multiple regions in the subgenual, medial prefrontal cortex, insula, and anterior cingulate. Interestingly, all DLPFC sites tested showed a significant negative correlation (anticorrelation) with the subgenual ranging from $p<0.01$ for the F3 site to $p<10^{-26}$ for BA46. All sites except F3 remained significantly anticorrelated ($p<10^{-3}$) after Bonferroni correction for multiple comparisons. Stimulation sites relying

TABLE 1

Coordinates used to generate a priori regions of interest (ROIs). A) Coordinates of treatment related decreases in the subgenual cingulate tied to antidepressant effect, the treatment modality used, and finally the average coordinates used to generate our a priori ROI. B) Coordinates of various left dorsal-lateral prefrontal cortex transcranial magnetic stimulation targets suggested in the literature. For all prior studies (A and B), we show the published coordinates are shown in either Talairach (Tx, Ty, Tz) or MNI (MNIx, MNIy, MNIz) space along with the transformed MNI coordinates used in the present study.

A) SUBGENUAL REGION

| Study | Tx | Ty | Tz | MNIx | MNIy | MNIz | Treatment |
|---|---|---|---|---|---|---|---|
| Wu et al. 1999 | 7 | 17 | −4 | 7 | 18 | −4 | Sleep Deprivation |
| Mayberg et al. 2000 | 4 | 2 | −4 | 4 | 2 | −5 | SSRI |
| Drevets et al. 2002 | 3 | 31 | −10 | 3 | 32 | −10 | SSRI |
| Mayberg et al. 2005 | −2 | 8 | −10 | −2 | 9 | −11 | DBS |
| Mayberg et al. 2005 | 10 | 20 | −4 | 10 | 21 | −4 | DBS |
| Kito et al. 2008 | 17 | 16 | −14 | 17 | 17 | −16 | TMS |
| Kito et al. 2011 | 8 | 21 | −9 | 8 | 22 | −9 | TMS |
| Nahas et al. 2007 | 0 | 8 | −16 | 0 | 9 | −19 | VNS |
| AVERAGE | | | | 5.9 | 16.3 | −9.8 | |

B) DLPFC REGIONS

| Study/Site | Tx | Ty | Tz | MNIx | MNIy | MNIz |
|---|---|---|---|---|---|---|
| Herwig 2001 5 cm Stim. Site | −42 | 17 | 52 | | | |
| Herbsman 2009 5 cm Stim. Site | −42 | 20 | 49 | | | |
| Herbsman 2009 5 cm Sham Site | −39 | 17 | 47 | | | |
| AVERAGE 5 cm Coordinates | −41 | 18 | 49 | −41 | 16 | 54 |
| Herbsman 2009 Responders | −46 | 25 | 44 | −46 | 23 | 49 |
| Herbsman 2009 Nonresponders | −41 | 19 | 50 | −41 | 17 | 55 |
| Herwig 2003 EEG (F3) Site | −37 | 27 | 44 | −37 | 26 | 49 |
| Rajkowska 1995 BA46 Definition | −44 | 40 | 25 | −44 | 40 | 29 |
| Rajkowska 1995 BA9 Definition | −36 | 40 | 38 | −36 | 39 | 43 |
| Paus 2001 TMS Target | −40 | 32 | 30 | −40 | 31 | 34 |
| Cho 2009 TMS Target | −40 | 32 | 30 | −40 | 31 | 34 |
| Fitgerald 2009 TMS Target | −46 | 45 | 35 | −46 | 45 | 38 |
| Rusjan 2010 TMS Target | −50 | 31 | 32 | −50 | 30 | 36 |

Three different analyses were used to relate functional connectivity of various left DLPFC TMS sites to previously reported clinical efficacy: 1) Paired comparison of functional connectivity between two TMS sites previously shown to differ in clinical efficacy (35, 36). 2) Correlation between functional connectivity and clinical efficacy as predicted by a previously reported equation (36): HDRS drop=−0.84+ (X*−0.022)+(Y*0.012). 3) Correlation between functional connectivity and clinical efficacy as previously reported in individual patients (42).

Motivated by the results of the above analyses, coordinates were identified in the left DLPFC that could potentially serve as optimized TMS targets by computing seed-based functional connectivity with our a priori ROI in the subgenual and our effective-ineffective map. Principal findings in normal subjects were confirmed in patients with depression.

on external skull-based landmarks including the 5 cm method and the EEG electrode method showed the weakest anticorrelation with the subgenual. Sites with strong physiological data showing distributed effects of TMS in the medial prefrontal cortex (25, 53) revealed a stronger anticorrelation. While both our BA9 and BA46 ROIs were anticorrelated, the stronger effect was for BA46. Finally, anatomical sites with either proven (35) or suggested (41) enhancement in clinical antidepressant response showed some of the strongest levels of anticorrelation.

Direct Comparison of Effective and Ineffective TMS Sites

Figure 17A:
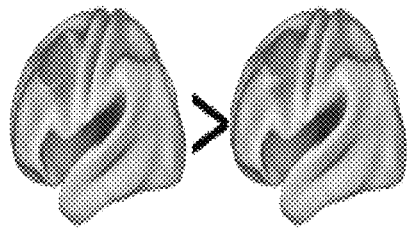
FIG. 17 illustrates differences in resting state functional connectivity between more effective versus less effective DLPFC stimulation sites. Coordinates are taken from Herbsman et al. 2009 (FIGS. 17A-17C) and Fitzgerald et al. 2009 (FIG. 17D-17F). The top row (17A, 17D) shows the DLPFC regions of interest compared in each study. The middle row (17B, 17E) shows significant differences in resting state functional connectivity between the two sites (more effective-less effective). The border of our a-priori defined subgenual region of interest is shown for reference. The bottom row (17C, 17F) shows bar graphs of the correlation of each DLPFC site with the subgenual cingulate. In both cases the more effective DLPFC site is significantly more anticorrelated with the subgenual cingulate than the less effective site.
Figure 17D:
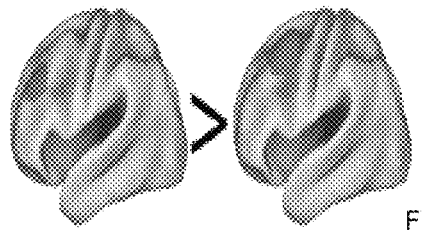
Figure 17B:
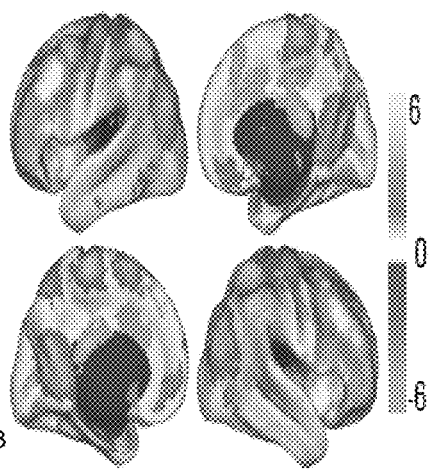
Figure 17E:
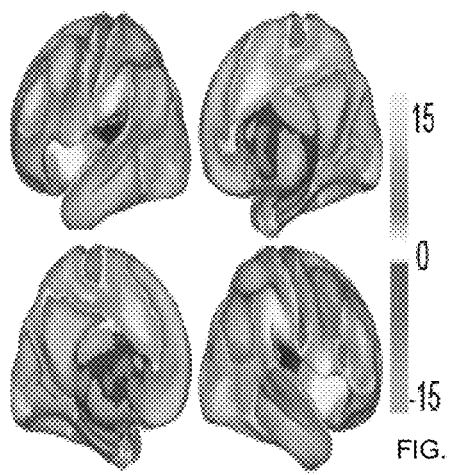
Figure 17C:
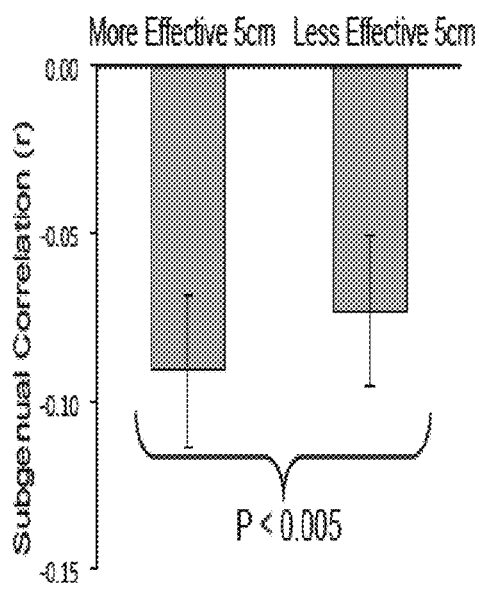
Figure 17F:
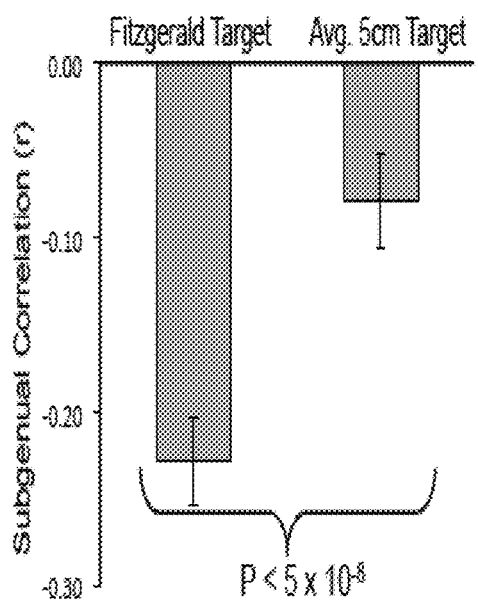

Next we directly compared the functional connectivity between pairs of coordinates from prior studies documenting that one coordinate was clinically superior to another for producing an antidepressant effect. In the first study (FIG. 17A), Herbsman et al. recorded the stimulation coordinates from 54 subjects treated with the 5 cm method (36). They averaged the stimulation sites for responders (−46, 23, 49) and showed this was anterior and lateral to the average stimulation site for non-responders (−41, 17, 55). Despite the fact that these coordinates are very close to one another, significant differences in functional connectivity were apparent (FIG. 17B). The more effective stimulation site was significantly more anticorrelated with the subgenual cingulate compared to the less effective site (FIG. 17C, P<0.005). In the second study (FIG. 17D) Fitzgerald et al. targeted a specific anatomical coordinate (−46, 45, 38) based on evidence from the depression neuroimaging literature and showed (in secondary analyses) that this was superior to the standard 5 cm target (−41, 16, 54, from our analysis) (35). The voxelwise distribution of significant differences in functional connectivity between these two targets (FIG. 17E) is similar to that in FIG. 17B, although more robust given the larger separation in the DLPF coordinates. Also similar to the comparison using the Herbsman et al.'s coordinates, the more effective stimulation site was significantly more anticorrelated with the subgenual cingulate compared to the less effective site (FIG. 17F, P<0.0001).

We combined results across these two pair-wise comparisons to generate a single map of voxels showing significant differences in functional connectivity between more effective versus less effective DLPFC stimulation sites (FIGS. 21A-21D). Peaks in this map were identified (23 positive, 29 negative) and include the subgenual cingulate in addition to several other regions implicated in depression including the medial prefrontal cortex, orbitofrontal cortex, subgenual cingulate, insula, thalamus, hypothalamus, and hippocampus (Suppl. Table 1).

Correlation Between fcMRI and Equation-based Clinical Efficacy

In addition to the above pair-wise comparisons, we examined the relationship between functional connectivity and the clinical efficacy of different DLPFC stimulation sites on a continuous basis. First, we computed the average clinical efficacy expected across a group of subjects based on the coordinates of each stimulation site using an equation empirically derived by Herbsman et al (2009) (36). We then plotted the predicted group-level clinical efficacy of all DLPFC stimulation sites considered in the current study (see Table 1) versus the resting state correlation of each site with the subgenual cingulate (FIG. 18A). Similar to the paired comparisons, DLPFC sites with higher predicted clinical efficacy showed stronger anticorrelation with the subgenual (r=−0.842, P<0.001 two-tailed). In fact, anticorrelation with the subgenual cingulate accounted for over 70% of the variance in clinical efficacy as predicted by Herbsman's empirically-derived equation.

Correlation Between fcMRI and Clinical Efficacy from Individual Patients

Moving beyond estimated group-level clinical efficacy using an equation, we next determined whether the above relationship held true for data from individual patients. To test this, we utilized a published table of left DLPFC stimulation coordinates and changes in the Montgomery & Asberg Depression Rating Scale for 27 individual patients receiving therapeutic TMS for depression (42). For each patient, we plotted their antidepressant response versus the resting state correlation between their specific stimulation site and the subgenual cingulate (FIG. 18B). Note that resting state correlation values in this analysis are average values across our 98 normal subjects, not values from these specific patients as no resting state fMRI data was collected in this prior study. Despite this limitation, left DLPFC sites with higher clinical efficacy in individual patients again showed stronger anticorrelation with the subgenual (r=−0.355, p<0.05 one-tailed). Interestingly, when applied to this independent cohort there was not a significant relationship between clinical efficacy measured in individual patients and group-level clinical efficacy as predicted by the Herbsman equation (r=0.122, p>0.25 one-tailed, FIG. 18C). This suggests that anticorrelation with the subgenual captures important variance not captured by the Herbsman equation alone.

Identification of Optimized TMS Targets

The above results are potentially of interest for understanding the antidepressant mechanism of TMS (see discussion), but perhaps more importantly this information can be directly translated into a method to identify connectivity-based coordinates in the left DLPFC that serve as an optimized TMS target. For example, the above results suggest that anticorrelation with the subgenual is related to antidepressant response. We can therefore use the subgenual ROI as a seed region and identify the peak anticorrelation in the left DLPFC (−44 38 34, FIG. 18A). Similarly, the above results provide a map of voxels more functionally connected to effective compared to less effective stimulation sites (see FIG. 21), One can use this map as a weighted seed region (minus the left DLPFC to avoid biasing results and inverted to maintain consistency with the subgenual results) to identify an optimized left DLPFC target (−38 44 26, FIG. 18B). Note that despite some difference in the coordinates of the peak anticorrelation, these two maps are very similar both across all grey matter voxels (spatial r=0.630) and specifically within the left DLPFC (spatial r=0.806). Interestingly there were several other nodes, besides the DLPFC, that were anticorrelated with the subgenual including parietal cortex/intraparietal sulcus, anterior insula, anterior SMA, and thalamus which could potentially serve as novel targets of focal brain stimulation for the treatment of depression (Suppl Table 1) (55, 56).

Replication of Results in Depression:

Since resting state functional connectivity can differ between normal subjects and patients with depression (57), we confirmed our results in an independent cohort of 13 patients with depression using both our subgenual seed region and our efficacy-based seed map. Similar to normal subjects, we found a significant anticorrelation between the subgenual and multiple left DLPFC TMS targets, including the optimized targets identified above (P<0.05, FIG. 19A). In paired comparisons, more effective sites showed a trend towards stronger anticorrelation with the subgenual and the optimized left DLPFC site was significantly more anticorrelated with the subgenual than the standard 5 cm target (P<0.05, FIG. 19B). As in normal subjects, there was a robust relationship between clinical efficacy as predicted by the Herbsman equation and anticorrelation with the subgenual (r=−0.812, P<0.005, FIG. 19C). Results were even more robust using our distributed efficacy-based seed map rather than the smaller and noisier subgenual ROI (FIGS. 19D-19F). Similar to the subgenual, many DLPFC targets including our optimized sites showed a significant negative correlation with the seed map (FIG. 19E). In paired comparisons, more effective sites were significantly more anticorrelated than less effective sites, including the Herbsman regions (P<0.05), the Fitzgerald regions (P<$10^{-4}$), and our new optimized site compared to the standard 5 cm target (P<$10^{-6}$). Finally, there was a highly significant relationship between predicted clinical efficacy and correlation with our efficacy-based seed map (r=−0.875, P<0.001).

Analyses were also replicated on the 11 control subjects from the same dataset as the 13 patients with depression (FIGS. 23A-23F). There were no significant differences between these control subjects and patients with depression.

Discussion:

In the current example, we used a novel connectivity-based approach to gain insight into why some left DLPFC TMS targets have proven more clinically effective than others. We identified robust differences in functional connectivity related to previously reported differences in clinical efficacy, particularly anticorrelation with the subgenual cingulate. We then demonstrated how one could translate this information into a connectivity-based targeting technique to identify coordinates in the left DLPFC that could potentially be used to optimize clinical response.

These results are relevant to understanding network models of depression, the antidepressant effect of TMS, and the functional relevance of intrinsic anticorrelations in resting state fMRI. Most importantly, the current results suggest that the clinical efficacy of focal brain stimulation might be optimized by targeting based on connectivity, and could find broad applicability across a number of diseases and stimulation techniques.

Relevance to Network Models of Depression

Depression is becoming increasingly recognized as a network disorder associated with alterations in a distributed set of regions including DLPFC (especially left), medial prefrontal, orbitofrontal, subgenual cingulate, insula, thalamus, hypothalamus, and hippocampus (15, 16). Of these regions, the left DLPFC and the subgenual cingulate have received the most attention due to the consistency of their depression-related abnormalities, their modulation with treatment across a range of therapies, and their use as targets of focal brain stimulation (58). Although depression functional imaging studies have produced heterogeneous results (16, 59-61), on average the abnormalities in these two regions have been opposite one another (58). The subgenual has been observed to be hyperactive in depression and a decrease in this hyperactivity is associated with antidepressant response (16, 17, 58) (see Table 1). Conversely, the left DLPFC tends to be hypoactive in depression and an increase in activity is associated with antidepressant response (58, 59). Consistent with this dichotomy, lesions of the ventral medial prefrontal cortex can improve depression while lesions of the dorsal lateral prefrontal cortex can exacerbate it (62).

The current finding that the subgenual and DLPFC are intrinsically anticorrelated during the resting state mirrors this dichotomy and shows that there is a link between the depression-related abnormalities in these two regions. There are several implications of this result. First, observed depression-related abnormalities in one region could be due solely to pathology in the opposing region. Primary hyperactivity in the subgenual might result in secondary hypoactivity of the DLPFC without anything being abnormal in the DLPFC and vice versa. Second, this anticorrelation could mediate compensatory responses. The DLPFC could increase its activity in response to subgenual hyperactivity in an attempt to suppress or normalize activity in this region, a mechanism that could explain the occasional finding of DLPFC hyperactivity in depression (15, 59, 60). Finally, focal inhibition/excitation of one region could be expected to respectively enhance/suppress activity of the other region. Indeed, DBS of the subgenual (which suppresses activity locally) results in an increase in activity in the DLPFC (17).

While the above discussion focused on the subgenual and the DLPFC, it is important to remember that the current results include several other regions previously implicated in the pathology of depression (15, 61). Our results show two anticorrelated groups of regions. The first includes the subgenual, medial prefrontal, superior frontal, hippocampus, posterior cingulate/precuneus, middle temporal gyrus, and cerebellar tonsils while the second includes the DLPFC, anterior insula, dorsal anterior cingulate/pre-SMA, thalamus, DLPFC, and parietal cortex.

Understanding the Antidepressant Mechanism of TMS

There has been much research into the antidepressant mechanism of DLPFC TMS in the hopes that this knowledge would facilitate optimization of the effect and improve clinical utility. Many hypotheses have been proposed (12, 63), however one idea that has been pursued aggressively is the propagation of TMS effects through anatomical connections to deeper limbic regions (12). A number of groups have attempted to localize the remote effects of DLPFC TMS by pairing it with neuroimaging techniques both in normal subjects and patients with depression. A full review of these heterogeneous results is beyond the scope of this article, however given the current findings we examined the results of these studies with respect to changes in the subgenual cingulate or adjacent medial prefrontal cortex (Suppl. Table 2). Although many studies found TMS-induced decreases in subgenual activity (20-24) or adjacent medial prefrontal activity (25-27), other studies found no significant changes in these regions (28, 29, 31-33), and one study observed increased medial prefrontal activity (29). The present findings using a novel connectivity-based approach are consistent with eight of the above thirteen studies and suggest that part of the antidepressant mechanism of DLPFC TMS may be remote suppression of activity in the subgenual cingulate and other limbic regions.

Relevance to the Debate Surrounding Anticorrelations

There has been substantial debate surrounding the appropriate interpretation of anticorrelations observed with resting state fcMRI in the setting of a preprocessing step termed global signal regression (47, 64-67). This processing can improve the specificity of resting state correlations and the correspondence with anatomy (65), however there are mathematical concerns that anticorrelations could emerge as "processing artifact." While the technical issues surrounding processing strategy and anticorrelations may be beyond the scope of this example (see Fox et al. 2009 for discussion), the current results add information to be considered in the ongoing debate. First, the fact that the resting state anticorrelation between the subgenual and DLPFC is recapitulated in patterns of pathological abnormalities seen in depression provides additional evidence that anticorrelations may reflect functionally meaningful relationships. Second, the focal brain stimulation interventions used in depression might serve as a causal test of the functional importance of anticorrelations. If stimulation/inhibition of one node suppresses/augments the activity of the anticorrelated node in a spatially specific manner and in proportion to the strength of the anticorrelation this would support the biological importance of anticorrelations.

An interesting issue is determining how anticorrelations observed with resting state fcMRI are mediated. In the case of the subgenual and DLPFC, the anticorrelation is unlikely to be the result of direct inhibitory connections. Monkey track tracing studies suggest that there are not direct anatomical connections between BA46 and BA25 (68, 69). However there are direct anatomical connections between the subgenual (BA25) and the anterior insula and mediodorsal nucleus of the thalamus, both of which are anticorrelated with the subgenual in the current analysis. Previous studies have implicated the fronto-insular cortex as a potential node mediating anticorrelations (70), and other studies have suggested the thalamus, especially the mediodorsal nucleus, as the site of integration of otherwise separate cortical-subcortical loops (71).

Targeting Focal Brain Stimulation Based on Connectivity

The idea that targets for focal brain stimulation should be selected at least partly based on their connectivity to other regions is not new, however implementing this strategy in practice has been difficult and empiric evidence supporting the utility of this approach has been limited (for review see (10)). It has been suggested that stimulation should be targeted to the portion of the DLPFC with connectivity to deeper limbic regions (12, 19). Unfortunately, the connectivity between the DLPFC and various limbic regions is complicated even in monkeys (68, 69), and the DLPFC is one of the areas that has expanded the most throughout evolution (54, 72). It has remained unclear which part of the human DLPFC should be stimulated and which limbic regions are important even if the human connectivity between the DLPFC and limbic regions was well established.

In the present example, we use intrinsic fcMRI with the subgenual and our efficacy-based seed map to identify left DLPFC TMS coordinates designed to optimize antidepressant response. These coordinates might serve as the basis for a clinical trial, however this connectivity-based targeting approach can be taken further. First, our results show the existence of other connectivity-based TMS targets for depression besides the DLPFC (see FIGS. 18A-18E, Suppl Table 1). Of these, the cerebellum and parietal cortex have previously been suggested as potential TMS targets in depression based on mood effects in normal subjects (56). A recent trial of low-frequency parietal stimulation failed to show a significant response beyond sham (55), however the present results show that high-frequency stimulation to the peak parietal node anticorrelated with the subgenual may be more effective. Second, the present example reports average group-level coordinates. Although average coordinates have previously been used in clinical trials of TMS for depression (35), an advantage of the current targeting approach is it can be applied at the single subject level. Given cross-subject heterogeneity in the location of the DLPFC (54), the full potential of connectivity-based targeting may be realized with identification of individualized TMS targets tailored to individual patients. Finally, the current targeting approach is potentially applicable across other diseases and brain stimulation techniques. Cortical correlates of deep brain stimulation sites based on fcMRI could serve as important TMS targets in Parkinson's disease, dystonia, obsessive compulsive disorder, or any other disease for which DBS provides clinical benefit (73). The converse of this approach also holds promise. Specifically, intrinsic fcMRI could be used to identify optimized DBS sites in individual patients based on connectivity with distributed cortical networks know to be impacted by disease.

Future Work

First, our results were generated on normal subjects then confirmed in a small cohort of patients with depression. Second, measures of clinical efficacy in the current example were based on previously published data and not obtained de novo. However, the fact that our connectivity results in normal subjects predicted clinical efficacy in an independent set of patients suggests that future work measuring both parameters in the same cohort should only increase the strength of the relationship. Finally, the current findings show that the antidepressant effect of TMS might be optimized through connectivity-based targeting.

Figures:

FIG. 16: Different left DLPFC TMS targets show variability in resting state functional connectivity, especially with the subgenual cingulate. The left hand column shows the coordinates and regions of interest for various left DLPFC TMS targets employed in the literature. The middle columns show resting state functional connectivity maps for each DLPFC region of interest. The border of our a-priori defined subgenual region of interest is show for reference. The right hand column is the correlation coefficient between the time course from each DLPFC region of interest and that of the subgenual cingulate.

FIG. 17: Differences in resting state functional connectivity between more effective versus less effective DLPFC stimulation sites. Coordinates are taken from Herbsman et al. 2009 (FIGS. 17A-17C) and Fitzgerald et al. 2009 (FIG. 17D-17F). The top row (17A, 17D) shows the DLPFC regions of interest compared in each study. The middle row (17B, 17E) shows significant differences in resting state functional connectivity between the two sites (more effective-less effective). The border of our a-priori defined subgenual region of interest is shown for reference. The bottom row (17C, 17F) shows bar graphs of the correlation of each DLPFC site with the subgenual cingulate. In both cases the more effective DLPFC site is significantly more anticorrelated with the subgenual cingulate than the less effective site.

FIG. 18: Identification of optimized left DLPFC TMS targets for depression respectively). Peak anticorrelations were identified in the left DLPFC that could serve as optimized targets for focal brain stimulation. fMRI time courses from the subgenual region of interest (red) and the anticorrelated left dorsal lateral prefrontal cortex (green) are shown for a representative subject (r=−0.23). based on functional connectivity. Regional time courses were extracted from our seed region in the subgenual cingulate (FIG. 18A) and our efficacy-based seed map (FIG. 18B) and used to generate resting state functional connectivity maps (FIGS. 18C and 18D respectively). Peak anticorrelations were identified in the left DLPFC that could serve as optimized targets for focal brain stimulation. fMRI time courses from the subgenual region of interest (red) and the anticorrelated left dorsal lateral prefrontal cortex (green) are shown for a representative subject (r=−0.23).

FIG. 19: Replication of principal findings in patients with major depressive disorder. Time course correlations are shown between regions of interest in the dorsal lateral prefrontal cortex (DLPFC) and the subgenual seed region (FIGS. 19A-19C) or the efficacy-based seed map (FIGS. 19D-19F). Similar to normal subjects, there is an anticorrelation between TMS targets in the DLPFC and the subgenual (FIG. 19A). Paired comparisons of effective versus less effective DLPFC targets show the same trend as normal subjects and a significant difference between the optimized DLPF target identified using the subgenual seed region (SG Target) and the average 5 cm target (FIG. 19B). Also similar to normal subjects, there is a strong relationship between estimated clinical efficacy (using the Herbsman equation) and anticorrelation with the subgenual (FIG. 19C; r2=0.66, P<0.005). Using the efficacy-based seed map rather than the small subgenual seed region produces similar but more robust results including examination of regional time course correlations (FIG. 19D), paired comparisons (FIG. 19E), and the correlation between functional connectivity and estimated clinical efficacy (FIG. 19F; $r^2$=0.76, P<0.001). Labels for DLPFC ROIs are as in FIGS. 16 and 17A-17F with the addition of optimized DLPFC targets identified in normal subjects using the subgenual seed region (SG Target) and the efficacy-based seed map (SM Target). *P<0.05, P<0.001, *P<10$^{-4}$.

REFERENCES

1. Wagner T, Valero-Cabre A, Pascual-Leone A (2007): Noninvasive human brain stimulation. *Annu Rev Biomed Eng.* 9:527-565.
2. Kobayashi M, Pascual-Leone A (2003): Transcranial magnetic stimulation in neurology. *Lancet Neurol.* 2:145-156.
3. Hallett M (2007): Transcranial magnetic stimulation: a primer. *Neuron.* 55:187-199.
4. Valero-Cabre A, Payne B R, Rushmore J, Lomber S G, Pascual-Leone A (2005): Impact of repetitive transcranial magnetic stimulation of the parietal cortex on metabolic brain activity: a 14C-2D G tracing study in the cat. *Experimental brain research Experimentelle Hirnforschung.* 163:1-12.
5. Valero-Cabre A, Payne B R, Pascual-Leone A (2007): Opposite impact on 14C-2-deoxyglucose brain metabolism following patterns of high and low frequency repetitive transcranial magnetic stimulation in the posterior parietal cortex. *Experimental brain research Experimentelle Hirnforschung.* 176:603-615.
6. Siebner H R, Bergmann T O, Bestmann S, Massimini M, Johansen-Berg H, Mochizuki H, et al. (2009): Consensus paper: combining transcranial stimulation with neuroimaging. *Brain Stimul.* 2:58-80.
7. Ruff C C, Driver 1, Bestmann S (2009): Combining TMS and fMRI: from 'virtual lesions' to functional-network accounts of cognition. *Cortex.* 45:1043-1049.
8. Ferreri F, Pasqualetti P, Maatta 5, Ponzo D, Ferrarelli F, Iononi G, et al. (2010): Human brain connectivity during single and paired pulse transcranial magnetic stimulation. *Neuroimage.*
9. Lisanby S H, Belmaker R H (2000): Animal models of the mechanisms of action of repetitive transcranial magnetic stimulation (RIMS): comparisons with electroconvulsive shock (ECS). *Depress Anxiety.* 12:178-187.
10. Fox M D, Halko M A, Eldaief M C, Pascual-Leone A (2012): Measuring and manipulating brain connectivity with resting state functional connectivity magnetic resonance imaging (fcMRI) and transcranial magnetic stimulation (TMS). *Neuroimage.* In press.
11. O'Reardon J P, Solvason H B, Janicak P G, Sampson S, Isenberg K E, Nahas Z, et al. (2007): Efficacy and safety of transcranial magnetic stimulation in the acute treatment of major depression: a multisite randomized controlled trial. *Biol Psychiatry.* 62:1208-1216.
12. Padberg F, George M S (2009): Repetitive transcranial magnetic stimulation of the prefrontal cortex in depression. *Exp Neural.* 219:2-13.
13. George M S, Wassermann E M, Williams W A, Callahan A, Ketter T A, Basser P, et al. (1995): Daily repetitive transcranial magnetic stimulation (rTMS) improves mood in depression. *Neuroreport.* 6:1853-1856.
14. Pascual-Leone A, Rubio B, Pallardo F, Catala M D (1996): Rapid-rate transcranial magnetic stimulation of left dorsolateral prefrontal cortex in drug-resistant depression. *Lancet.* 348:233-237.
15. Mayberg H S (2007): Defining the neural circuitry of depression: toward a new nosology with therapeutic implications. *Biol Psychiatry.* 61:729-730.
16. Drevets W C, Savitz J, Trimble M (2008): The subgenual anterior cingulate cortex in mood disorders. *CNS spectrums.* 13:663-681.
17. Mayberg H S, Lozano A M, Voon V, McNeely H E, Seminowicz D, Hamani C, et al. (2005): Deep brain stimulation for treatment-resistant depression. *Neuron.* 45:651-660.
19. Mayberg H S (2009): Targeted electrode-based modulation of neural circuits for depression. *J Clin Invest.* 119:717-725.
20. George M S, Wassermann E M, Kimbrell T A, Little J T, Williams W E, Danielson A L, et al. (1997): Mood improvement following daily left prefrontal repetitive transcranial magnetic stimulation in patients with depression: a placebo-controlled crossover trial. The American Journal of Psychiatry. 154:1752-1756.
21. George M S, Stallings L E, Speer A M, Nahas Z, Spicer K M, Vincent D J, et al. (1999): Prefrontal repetitive transcranial magnetic stimulation (rTMS) changes relative perfusion locally and remotely. *Human Psychopharmacology: Clinical and Experimental.* 14:161-170.
22. Kimbrell Ta, Dunn R T, George M S, Danielson A L, Willis M W, Repella J D, et al. (2002): Left prefrontal-repetitive transcranial magnetic stimulation (rTMS) and regional cerebral glucose metabolism in normal volunteers. *Psychiatry research.* 115:101-113.
23. Narushima K, McCormick L M, Yamada T, Thatcher R W, Robinson R G (2010): Subgenual cingulate theta activity predicts treatment response of repetitive transcranial magnetic stimulation in participants with vascular depression. *The Journal of neuropsychiatry and clinical neurosciences.* 22:75-84.
24. Kito S, Fujita K, Koga Y (2008): Regional cerebral blood flow changes after low-frequency transcranial magnetic stimulation of the right dorsolateral prefrontal cortex in treatment-resistant depression. *Neuropsychobiology.* 58:29-36.
25. Kito S, Hasegawa T, Koga Y (2011): Neuroanatomical correlates of therapeutic efficacy of low-frequency right prefrontal transcranial magnetic stimulation in treatment-resistant depression. *Psychiatry Clin Neurosci.* 65:175-182.
26. Paus T, Castro-Alamancos Ma, Petrides M (2001): Cortico-cortical connectivity of the human mid-dorsolateral frontal cortex and its modulation by repetitive transcranial magnetic stimulation. *European Journal of Neuroscience.* 14:1405-1411.
27. Li X, Nahas Z, Kozel F A, Anderson B, Bohning D E, George M S (2004): Acute left prefrontal transcranial magnetic stimulation in depressed patients is associated with immediately increased activity in prefrontal cortical as well as subcortical regions. *Biological psychiatry.* 55:882-890.
28. Teneback C C, Nahas Z, Speer A M, Molloy M, Stallings L E, Spicer K M, et al. (1999): Changes in prefrontal cortex and paralimbic activity in depression following two weeks of daily left prefrontal TMS. *Journal of Neuropsychiatry and Clinical Neurosciences.* 11:426.
29. Nahas Z, Lomarev M, Roberts D R, Shastri a, Lorberbaum J P, Teneback C, et al. (2001): Unilateral left prefrontal transcranial magnetic stimulation (TMS) produces intensity-dependent bilateral effects as measured by interleaved BOLD fMRI. *Biological psychiatry.* 50:712-720.
30. Speer A M, Kimbrell T A, Wassermann E M, D Repella J, Willis M W, Herscovitch P, et al. (2000): Opposite effects of high and low frequency rTMS on regional brain activity in depressed patients. *Biological psychiatry.* 48:1133-1141.

31. Mottaghy F M, Keller C E, Gangitano M, Ly 1, Thall M, Parker J A, et al. (2002): Correlation of cerebral blood flow and treatment effects of repetitive transcranial magnetic stimulation in depressed patients. *Psychiatry research.* 115:1-14.

32. Eisenegger C, Treyer V, Fehr E, Knoch D (2008): Time-course of "off-line" prefrontal rTMS effects—a PET study. *Neurolmage.* 42:379-384.

33. Knoch D, Treyer V, Regard M, Muri R M, Buck A, Weber B (2006): Lateralized and frequency-dependent effects of prefrontal rTMS on regional cerebral blood flow. *Neurolmage.* 31:641-648.

34. Speer A M, Willis M W, Herscovitch P, Daube-Witherspoon M, Shelton J R, Benson B E, et al. (2003): Intensity-dependent regional cerebral blood flow during 1-Hz repetitive transcranial magnetic stimulation (rTMS) in healthy volunteers studied with H2150 positron emission tomography: II. Effects of prefrontal cortex rTMS. *Biological psychiatry.* 54:826-832.

35. Ferrarelli F, Haraldsson H M, Barnhart T E, Roberts A D, Oakes T R, Massimini M, et al. (2004): A [17Fj-fluoromethane PET/TMS study of effective connectivity. *Brain research bulletin.* 64:103-113.

36. Fitzgerald P B, Hoy K, McQueen S, Mailer J J, Herring S, Segrave R, et al. (2009): A randomized trial of rTMS targeted with MRI based neuro-navigation in treatment-resistant depression. *Neuropsychopharmacology.* 34:1255-1262.

37. Herbsman T, Avery D, Ramsey D, Holtzheimer P, Wadjik C, Hardaway F, et al. (2009): More lateral and anterior prefrontal coil location is associated with better repetitive transcranial magnetic stimulation antidepressant response. *Biol Psychiatry.* 66:509-515.

38. Herwig U, Padberg F, Unger J, Spitzer M, Schonfeldt-Lecuona C (2001): Transcranial magnetic stimulation in therapy studies: examination of the reliability of "standard" coil positioning by neuronavigation. *Biol Psychiatry.* 50:58-61.

39. Ahdab R, Ayache S S, Brugieres P, Goujon C, Lefaucheur J-P (2010): Comparison of "standard" and "navigated" procedures of TMS coil positioning over motor, premotor and prefrontal targets in patients with chronic pain and depression. *Neurophysiologie clinique=Clinical neurophysiology.* 40:27-36.

40. George M S, Wassermann E M, Williams W A, Steppe! J, Pascual-Leone A, Basser P, et al. (1996): Changes in mood and hormone levels after rapid-rate transcranial magnetic stimulation (rTMS) of the prefrontal cortex. *J Neuropsychiatry Clin Neurosci.* 8:172-180.

41. Herwig U, Satrapi P, Schonfeldt-Lecuona C (2003): Using the international 10-20 EEG system for positioning of transcranial magnetic stimulation. *Brain Topogr.* 16:95-99.

42. Rusjan P M, Barr M S, Farzan F, Arenovich T, Mailer J J, Fitzgerald P B, et al. (2010): Optimal transcranial magnetic stimulation coil placement for targeting the dorsolateral prefrontal cortex using novel magnetic resonance image-guided neuronavigation. *Human brain mapping.* 31:1643-1652.

43. Paillere Martinot M-L, Galinowski A, Ringuenet D, Gallarda T, Lefaucheur J-P, Bellivier F, et al. (2010): Influence of prefrontal target region on the efficacy of repetitive transcranial magnetic stimulation in patients with medication-resistant depression: a [(18)] H-fluoro-deoxyglucose PET and MRI study. *The international journal of neuropsychopharmacology/official scientific journal of the Collegium Internationale Neuropsychopharmacologicum (GNP).* 13:45-59.

44. Herwig U, Lampe Y, Juengling F D, Wunderlich A, Walter H, Spitzer M, et al. (2003): Add-on rTMS for treatment of depression: a pilot study using stereotaxic coil-navigation according to PET data. J Psychiatr Res. 37:267-275.

45. Garcia-Toro M, Salva J, Daunnal 1, Andres J, Romera M, Lafau 0, et al. (2006): High (20-Hz) and low (1-Hz) frequency transcranial magnetic stimulation as adjuvant treatment in medication-resistant depression. *Psychiatry research.* 146:53-57.

46. Biswal B, Yetkin F, Haughton V, Hyde J (1995): Functional connectivity in the motor cortex of resting human brain using echo-planar MRI. Magnetic Resonance in Medicine. 34:537-541.

47. Fox M D, Raichle M E (2007): Spontaneous fluctuations in brain activity observed with functional magnetic resonance imaging. *Nat Rev Neurosci.* 8:700-711.

48. Van Dijk K R, Hedden T, Venkataraman A, Evans K C, Lazar S W, Buckner R L (2010): Intrinsic functional connectivity as a tool for human connectomics: theory, properties, and optimization-Journal *of neurophysiology.* 103:297-32.

49. Fox M D, Snyder A Z, Vincent J L, Corbetta M, Van Essen D C, Raichle M E (2005): The human brain is intrinsically organized into dynamic, anticorrelated functional networks. *PNAS.* 102:9673-9678.

50. Wu J, Buchsbaum M S, Gillin J C, Tang C, Cadwell S, Wiegand M, et al. (1999): Prediction of antidepressant effects of sleep deprivation by metabolic rates in the ventral anterior cingulate and medial prefrontal cortex. *Am J Psychiatry.* 156:1149-1158.

51. Mayberg H S, Brannan S K, Tekell J L, Silva J A, Mahurin R K, McGinnis 5, et al. (2000): Regional metabolic effects of fluoxetine in major depression: serial changes and relationship to clinical response. *Biol Psychiatry.* 48:830-843.

52. Drevets W C, Bogers W, Raichle M E (2002): Functional anatomical correlates of antidepressant drug treatment assessed using PET measures of regional glucose metabolism. Eur Neuropsychopharmacol. 12:527-544.

53. Nahas Z, Teneback C, Chae J H, Mu Q, Molnar C, Kozel F A, et al. (2007): Serial vagus nerve stimulation functional MRI in treatment-resistant depression. *Neuropsychopharmacology.* 32:16491660.

54. Cho S S, Strafella A P (2009): rTMS of the left dorsolateral prefrontal cortex modulates dopamine release in the ipsilateral anterior cingulate cortex and orbitofrontal cortex. PloS one. 4:e6725.

55. Rajkowska G, Goldman-Rakic P S (1995): Cytoarchitectonic definition of prefrontal areas in the normal human cortex: II. Variability in locations of areas 9 and 46 and relationship to the Talairach Coordinate System. *Cereb Cortex.* 5:323-337.

56. Schutter D J, Laman D M, van Honk J, Vergouwen A C, Koerselman G F (2009): Partial clinical response to 2 weeks of 2 Hz repetitive transcranial magnetic stimulation to the right parietal cortex in depression. *The international journal of neuropsychopharmacology/official scientific journal of the Collegium Internationale Neuropsychopharmacologicum.* 12:643-650.

57. Schutter D J, van Honk J (2005): A framework for targeting alternative brain regions with repetitive transcranial magnetic stimulation in the treatment of depression. *Journal of psychiatry & neuroscience: JPN.* 30:91-97.
58. Greicius M D, Flores B H, Menon V, Glover G H, Solvason H B, Kenna H, et al. (2007): Resting-State Functional Connectivity in Major Depression: Abnormally Increased Contributions from Subgenual Cingulate Cortex and Thalamus. *Biol Psychiatry.*
59. Koenigs M, Grafman 1 (2009): The functional neuroanatomy of depression: distinct roles for ventromedial and dorsolateral prefrontal cortex. *Behavioural brain research.* 201:239-243.
60. Fitzgerald P B, Oxley T J, Laird A R, Kulkarni J, Egan G F, Daskalakis Z J (2006): An analysis of functional neuroimaging studies of dorsolateral prefrontal cortical activity in depression. *Psychiatry research.* 148:33-45.
61. Steele J D, Currie J, Lawrie S M, Reid I (2007): Prefrontal cortical functional abnormality in major depressive disorder: a stereotactic meta-analysis. *Journal of affective disorders.* 101:1-11.
62. Fitzgerald P B, Laird A R, Mailer 1, Daskalakis Z J (2008): A meta-analytic study of changes in brain activation in depression. *Human brain mapping.* 29:683-695.
63. Koenigs M, Huey E D, Calamia M, Raymont V, Tranel D, Grafman 1 (2008): Distinct regions of prefrontal cortex mediate resistance and vulnerability to depression. *The Journal of neuroscience: the official journal of the Society for Neuroscience.* 28:12341-12348.
64. Paus T, Barrett J (2004): Transcranial magnetic stimulation (TMS) of the human frontal cortex: implications for repetitive TMS treatment of depression. *Journal of psychiatry & neuroscience:*1P N. 29:268-279.
65. Murphy K, Birn R M, Handwerker D A, Jones T B, Bandettini P A (2009): The impact of global signal regression on resting state correlations: Are anti-correlated networks introduced? *Neuroimage.* 44:893-905.
66. Fox M D, Zhang D, Snyder A Z, Raichle M E (2009): The global signal and observed anticorrelated resting state brain networks. J *Neurophysiol.* 101:3270-3283.
67. Anderson I S, Druzgal T J, Lopez-Larson M, Jeong E-K, Desai K, Yurgelun-Todd D (2010): Network anticorrelations, global regression, and phase-shifted soft tissue correction. *Human brain mapping.* 00.
68. Chai Xi, Castanon A N, Ongur D, Whitfield-Gabrieli S (2011): Anticorrelations in resting state networks without global signal regression. *NeuroImage.*
69. Petrides M, Pandya D N (1999): Dorsolateral prefrontal cortex: comparative cytoarchitectonic analysis in the human and the macaque brain and corticocortical connection patterns. The European journal of neuroscience. 11:1011-1036.
70. Vogt B A, Pandya D N (1987): *Cingulate cortex of the rhesus monkey: II. Cortical afferents. The Journal of comparative neurology.* 262:271-289.
71. Sridharan D, Levitin D J, Menon V (2008): A critical role for the right fronto-insular cortex in switching between central-executive and default-mode networks. *Proc Natl Acad Sci USA.* 105:12569-12574.
72. Groenewegen H J, Galis-de Graaf Y, Smeets W J (1999): Integration and segregation of limbic cortico-striatal loops at the thalamic level: an experimental tracing study in rats. *J Chem Neuroanat.* 16:167-185.
73. Van Essen D C, Dierker D L (2007): Surface-based and probabilistic atlases of primate cerebral cortex. *Neuron.* 56:209-225.
74. Hamani C, Nobrega 1N, Lozano aM (2010): Deep brain stimulation in clinical practice and in animal models. Clinical pharmacology and therapeutics. 88:559-562.

Supplemental Information
Supplementary Methods:
Subjects and Data Collection:

Two datasets were used in the present example. The first consisted of 98 healthy right-handed subjects (48 male, ages 22±3.2 years (mean±SD)) collected in Boston, Mass. and was a subset of subjects previously used in an analysis of resting state functional connectivity (1). Experiments were conducted with the written consent of each subject and approved by the Partners' Institutional Review Board. Imaging was performed on a 3 T Siemens whole body MRI System with a phased array head coil. Each subject completed two 6.2 min long (124 frames) resting state fMRI scans (TR=3000 ms, TE=30 ms, FA=85°, 3×3×3 mm voxels, FOV=216, 47 axial slices with interleaved acquisition and no gap). During scanning, participants were instructed to keep their eyes open and remain still. All subjects were originally enrolled in an fMRI study on cognitive tasks; the resting state data used in this study was collected at the beginning of each subject's scan before any tasks were performed. Structural data included a high-resolution multi-echo T1-weighted magnetization-prepared gradient-echo image (TR=2200 ms, TI=1100 ms, TE=1.54 ms for image 1 to 7.01 ms for image 4, FA=7°, 1.2×1.2×1.2 mm voxels, FOV=230)(2). The second dataset included 13 subjects with major depressive disorder (3 male, mean age 40.2 years, mean HAM-D 23.8) and eleven healthy control subjects (5 male, mean age 29 years, mean HAM-D 0.4) collected in Palo Alto, Calif. Data on 14 subjects with depression was originally collected, however one patient was excluded based on structural abnormalities on their MRI scan. Depressed subjects aged 18-65 years meeting DSM-IV criteria for major depression and a Hamilton Depression Rating Scale score>18 were recruited utilizing online advertisements, radio advertisements and fliers posted in the community. Healthy controls not meeting criteria for MDD were subject to identical inclusion and exclusion requirements. All subjects underwent screening with the Structured Clinical Interview for DSM Disorders (SCID) by a trained psychologist. Subjects were excluded if they a history of significant head trauma, active abuse of alcohol or illegal substances, bipolar affective disorder, any psychotic disorder, obsessive-compulsive disorder, or any significant neurologic history (i.e. seizure, stroke, multiple sclerosis). Subjects had to be right-handed and could not have taken any psychotropic medication within two weeks of study enrollment. Depression severity was measured using the 21-item Hamilton Depression Rating Scale, Beck Depression Inventory, and the Montgomery Asberg Depression Rating Scale. The Stanford University Medical Center Institutional Review Board (IRB) approved the study, and all subjects signed an IRB approved informed consent. Imaging was performed at the Richard M. Lucas Center for Imaging at Stanford University on a 3-T General Electric Signa scanner using a standard whole-head coil. Each subject completed one 10 minute long (300 frames) resting state fMRI scan using a T2*weighted gradient echo spiral in/out pulse sequence (TR=2000 ms, TE=30 ms, FA=80°, 3.4×3.4×4.5 mm voxels, 31 axial slices with interleaved acquisition, 4 mm thickness, and 0.5 mm gap). Patients were instructed to "lie still with your eyes closed, try not to think of any one thing in particular and try not to fall asleep." Structural data included a high-resolution T1-weighted spoiled gradient recalled 3-D MRI sequence (TR=40 ms, minimum TE, FA=11°, 0.86×0.86×1.2 mm voxels, 128 axial slices with interleaved acquisition).

A Priori Defined Regions of Interest:

Several regions of interest (ROI) were defined a priori for use in the present analysis including one ROI in the subgenual cingulate cortex (FIGS. 20A-B) and multiple ROIs in the left DLPFC (FIG. 16, FIGS. 17A-F). To construct an ROI in the subgenual cingulate cortex, we first identified coordinates from prior studies where a reduction in subgenual activity was associated with antidepressant response across a wide range of treatment modalities (3-9) (Table 1). This is not intended to be an exhaustive list, but to sample the literature across a range of therapeutic interventions. We converted the reported subgenual coordinates (generally in Talairach space) into MNI space using tal2mni (http://imaging.mrc-cbu.cam.ac.uk/imaging/MniTalairach). For the purposes of the current study, "Talairach" refers to the atlas coordinate space as defined by Talairach and Tournoux in 1988 (10). After conversion to MNI space, coordinates were averaged across all seven studies. We created a single 10 mm sphere centered on these coordinates (6, 16, −10) and masked this ROI to exclude voxels not sampled in any of our 98 subjects or voxels falling outside of the cerebral cortex using the Harvard Oxford cortical regions template available in FSL.

To construct left DLPFC regions of interest, we identified coordinates from a variety of studies of left DLPFC TMS (Table 2). Some studies focused on anatomical targeting (11-14), some on the physiological effect of TMS in normal subjects (15, 16), and some on anatomically defining Brodmann areas in the DLPFC (17) that have been suggested as optimal TMS stimulation sites (18).

For studies reporting Talaraich coordinates, these were transformed into MNI space using tal2mni. For those studies reporting MNI coordinates (13) these were converted to Talaraich coordinates using mni2tal (http://imaging.mrc-cbu.cam.ac.uk/imaging/MniTalairach). The coordinates for the Fitzgerald 2009 site were reported in Talairach coordinates in the initial publication (11), but MNI coordinates in a later publication by the same group (13). These later MNI coordinates (−46, 45, 38) are close but not identical to those obtained via tal2mni (−45, 45, 40), so we chose to use the previously published values (13). Since multiple studies reported average coordinates resulting from the 5 cm targeting method (12, 14), these coordinates were averaged to create one set of coordinates best representing the standard 5 cm target site. To generate coordinates for Brodmann regions (BA9 and 46) the average y and z Talairach coordinates were taken from Rajkowska and Goldman-Rakic 1995 (17). However this paper did not report x coordinates so this was determined from the coordinate in Talairach space on the cortical surface constrained by the y and z coordinates (10). This complete set of Talairach coordinates was then transformed into MNI space. 20 mm radius spheres were generated centered on each of these DLPFC coordinates in MNI space. This sphere size is larger than the sphere size often used in intrinsic functional connectivity studies and was chosen for three reasons. First, several coordinates used in the present example are actually average coordinates across multiple stimulation sites scattered over several centimeters (12, 14, 19) and this larger sphere size more accurately captures this distribution. Second, even when specific coordinates are targeted, the spread of TMS stimulation can be up to several centimeters with focal figure eight coils and even greater with the FDA approved Neurostar coil (20). Finally, some of the DLPFC coordinates reported in the literature (11) seemed to reside above the cortical surface (in both Talairach and MNI space), and the larger sphere size enabled robust ROIs to still be created using the published coordinates.

A single large left DLPFC region of interest was also generated designed to cover all voxels that could reasonably be considered part of the left DLPFC by combining 25 mm radius spheres centered on the coordinates for BA9, BA46, and the standard 5 cm TMS site. All DLPFC ROIs were left sided (unilateral), and masked to eliminate any unsampled voxels or voxels lying outside of grey matter as defined by the standard Harvard/Oxford grey matter template in FSL thresholded at an intensity of 70.

Data Processing:

fMRI data from both datasets were processed in accordance with the strategy of Fox et al 2005 (21) as implemented in Van Dijk 2010 (22). In brief, functional data were preprocessed to decrease image artifacts and between-slice timing differences. Data were then spatially smoothed using a Gaussian kernel of 6 mm full-width at half-maximum and temporally filtered (0.009 Hz<f<0.08 Hz). Next, several spurious or nonspecific sources of variance were removed by regression of the following variables: (1) six movement parameters computed by rigid body translation and rotation during preprocessing, (2) mean whole brain signal, (3) mean brain signal within the lateral ventricles, and (4) the mean signal within a deep white matter ROI. Inclusion of the first temporal derivatives of these regressors within the linear model accounted for the time-shifted versions of spurious variance.

Time courses were extracted by averaging across voxels in each seed region. For seed regions with varying voxel values (i.e. seed maps) a weighted average was used. Correlation between extracted time courses was assessed using Pearson's correlation coefficient. For statistical testing Fisher's r-to-z transform was used and either single group or paired t-tests were used to determine significance (two-tailed). After averaging and statistics, Fisher z values were converted back to r values using the Fisher inverse transform. Error bars on r values reflect the standard en⁻ or of Fisher z values. To generate functional connectivity maps, the Pearson's correlation coefficient was computed between the seed region time course and that of all other voxels. Fisher's r-to-z transformation was used to convert correlation maps into z maps. Group effects were tested with a random effects analysis using a one sample t-test. For seed-based correlation maps, images were threshold at t=4.25 P<0.0001 uncorrected. Similarity between seed based correlation maps was assessed using a spatial correlation coefficient across voxels (23). All data processing, calculations, and thresholding were performed in volume space. For display purposes data were mapped to the cortical surface using CARET and the PALS atlas (24). ROI's and integer-based overlaps are displayed using average fiducial mapping option in CARET while functional data are displayed using the multi-fiducial mapping option.

Relating Functional Connectivity to Previously Reported Clinical Efficacy

Three different analyses were used to relate functional connectivity of various left DLPFC TMS sites to previously reported clinical efficacy: 1) Paired comparison of functional connectivity between two TMS sites previously shown to differ in clinical efficacy, 2) correlation between functional connectivity and clinical efficacy as predicted by a previously reported equation, 3) correlation between functional connectivity and clinical efficacy as previously reported in individual patients.

1) To explore differences in functional connectivity between pairs of TMS sites previously shown to differ in clinical efficacy, we utilized two prior studies each comparing two DLPFC stimulation sites: Herbsman et al. (12) and Fitzgerald et al. (11). Functional connectivity was compared between each effective versus less effective site using a paired t-test and images were thresholded at t=3.0, P<0.005 uncorrected. Since two of these paired maps were generated, a combined effective-ineffective map was constructed by averaging the two individual maps then masking this with a map of voxels significant in both analyses. Local maxima (peaks) in this map were determined using the FSL Cluster algorithm, threshold of t=5 (positive or negative), minimum cluster size of 2, and one peak per cluster. Thresholds were chosen empirically to return approximately 20-30 negative peaks and 20-30 positive peaks.

2) To compute the predicted group-level clinical efficacy of different DLPFC stimulation sites we used the empirically derived equation from Herbsman et al 2009 (12): HDRS drop=$-0.84+(X*-0.022)+(Y*0.012)$. Since this equation was derived based on Talairach coordinates (10), these coordinates were used to compute the predicted clinical efficacy. The relationship between the predicted group-level clinical efficacy and intrinsic connectivity with the subgenual was computed using Pearson's correlation coefficient (two-tailed).

3) To determine if the above correlation between clinical efficacy and subgenual connectivity held true in individual subjects, subject-specific stimulation coordinates and clinical responses (changes in Montgomery & Asberg Depression Rating Scale) were taken from Paillere-Martinot 2010 (18). Only those subjects with left sided simulation (N=27) were included. Ten mm spheres were created at each of these coordinates then masked to eliminate any unsampled voxels or voxels lying outside of grey matter as defined by the standard Harvard/Oxford grey matter template in FSL thresholded at an intensity of 70. The expected relationship between clinical efficacy and intrinsic connectivity with the subgenual was confirmed using Pearson's correlation coefficient (one-tailed given the a-priori hypothesis regarding the direction of the expected correlation).

Connectivity Based Targeting

Given the results of the above analyses, coordinates were identified in the left DLPFC that could potentially serve as optimized TMS targets by computing seed-based functional connectivity with two regions: our a priori ROI in the subgenual and our effective-ineffective map.

For the subgenual ROI functional connectivity map, local maxima (peaks) were determined using the FSL Cluster algorithm. Negative peaks were identified using a threshold of t=10, minimum cluster size of 2, and one peak per cluster. Positive peaks were identified using a threshold of t=8, minimum cluster size 2, and one peak per cluster except for the singe large cluster centered around the subgenual seed region for which an additional 10 peaks were included. Thresholds for peak identification were chosen empirically and were varied in order to return approximately 20-30 negative peaks and 20-30 positive peaks.

In order to use the result of our paired effective-ineffective analysis as a "seed map" for identifying optimized left DLPFC coordinates, voxels in the left DLPFC ROI were excluded and the map was inverted (multiplied by negative 1) to maintain consistency with the direction of the relationships observed with the subgenual seed (i.e. negative correlation=improved clinical efficacy). We will refer to this map as the "efficacy-based seed map." Note that the use of this seed map will bias any coordinates outside the DLPFC so additional peaks in this functional connectivity map are not reported.

Replication in Patients with Depression:

To confirm that the above relationship between reported clinical efficacy and subgenual functional connectivity identified in normal subjects held true in patients with depression, we replicated our primary findings in 13 patients with major depression. Given that we were confirming a priori hypotheses, one-tailed t-tests were used. These analyses were also performed in 11 normal subjects from the same dataset and compared to the 13 patients with depression using two-tailed t-tests.

SUPPLEMENTARY TABLE 1

Peak Coordinates from Functional Connectivity Maps. Region names are displayed in the left column, local maxima for regions showing a difference in functional connectivity between effective versus ineffective DLPFC TMS sites (see FIG. 21) are shown in the middle column, and local maxima for regions showing significant functional connectivity with the subgenual cingulate (see FIG. 18A) are shown in the right column. Note that both lists are divided into positive and negative peaks, although with the order reversed between lists to better illustrate commonalities. All coordinates are in MNI space (MNIx, MNIy, MNIz). PFIG = parahippocampal gyrus, pSMA = pre-SMA

| Region | Effective-ineffective Peaks | Subgenual fcMRI Peaks |
|---|---|---|
| | NEGATIVE PEAKS | POSITIVE PEAKS |
| Subgenual Cingulated Cortex | (−8 24 −16) | (2 16 −10) |
| Medial Prefrontal Cortex | (−2 52 −12) (−4 30 −22) | (−6 34 −10) (10 36 −12) (−2 44 −24) (0 60 −20) |
| Superior Frontal Gyrus | (−38 14 54) (22 34 48) (−4 46 36) | (−6 48 48) (18 35 54) |
| Middle Frontal Gyrus [BA44] | (−46 14 48) | |
| Posterior Cingulate/Precuneus | (−2 −56 24) (−4 −36 36) (−2 −58 44) | (8 −52 22) |
| Hippocampus/PHG | (−24 −36 −20) (24 −22 −24) (−14 −32 −10) | (24 −20 −24) (−26 −20 −24) |
| Lateral parietal/occipital | (−42 −68 36) (46 −64 30) | (−40 −76 46) (54 −66 32) (52 −70 36) |
| Cerebellar Tonsils | (8 −54 −48) | (−4 −50 −46) |
| Cerebellar Hemisphere | (42 −72 −34) (16 −88 −38) (38 −72 −48) (16 −72 −26) (8 −88 −38) | |
| Middle Temporal Gyrus | (−58 −16 −22) (58 −4 −26) | (58 −8 −22) (−54 −10 −22) |
| Inferior Temporal Gyrus | | (−46 −2 −44) (40 −12 −42) |
| Somatomotor Cortex | (−6 −32 66) (34 −24 60) (12 −28 64) (−30 −24 60) | |
| Orbitofrontal cortex | | (22 20 −22) (−24 18 −24) |
| Tamporal Pole | | (40 16 −46) |
| Femeral Pole | (−8 66 18)(−12 60 10) | (−2 58 4) |

SUPPLEMENTARY TABLE 1-continued

Peak Coordinates from Functional Connectivity Maps. Region names are displayed in the left column, local maxima for regions showing a difference in functional connectivity between effective versus ineffective DLPFC TMS sites (see FIG. 21) are shown in the middle column, and local maxima for regions showing significant functional connectivity with the subgenual cingulate (see FIG. 18A) are shown in the right column. Note that both lists are divided into positive and negative peaks, although with the order reversed between lists to better illustrate commonalities. All coordinates are in MNI space (MNIx, MNIy, MNIz). PFIG = parahippocampal gyrus, pSMA = pre-SMA

| Region | Effective-ineffective Peaks | Subgenual fcMRI Peaks |
|---|---|---|
| | POSITIVE PEAKS | NEGATIVE PEAKS |
| DLPFC | (−38 40 32) | (−44 38 34) (40 42 30) (50 48 20) |
| Anterior Insula | (−42 14 −6) (−42 8 −46) (−30 −24 2) | (−26 18 2) (30 20 10) (34 4 12) |
| Operculum | | (−48 10 8) (34 2 2) |
| Mid/posterior cingulate | (12 −30 42) (−10 −28 42) (8 −20 24) (−12 −38 44) | |
| Precuneus | (14 −70 42) | |
| Dorsal Anterior Cingulate/pSMA | (4 18 34) | (8 16 48) |
| Thalamus (mediodorsal nucleus) | (10 −22 4) (6 −16 0) | (−18 −6 12) (10 −12 0) (−22 −22 12) |
| Putamen | (−28 −10 6) (20 −6 14) | |
| Parietal Cortex BA19 | (62 −34 36) (−66 −30 30) | (−42 −44 44)(36 −48 50) |
| Lateral Occipital Cortex BA19 | | (−24 −70 26) |
| Orbitofrontal | (−26 38 −12) (16 8 −24) (22 42 −12) (−20 6 −24) | (−46 44 2) (−46 46 16) |
| R precentral gyrus | (54 4 34) | |
| Cerebellum | | (−26 −72 −20) |

SUPPLEMENTARY TABLE 2

Neuroimaging changes in the subgenual cingulate or adjacent medial prefontal cortex in response to dorsal lateral prefontal cortex TMS. Studies varied in their study population (normal controls versus depression patients), rTMS frequency (high or low), hemisphere (right or left), session (during a single session or after repeated sessions), and neuroimaging technique: single photon emission tomography (SPECT), positron emission tomography (PET), functional magnetic resonance imaging (fMRI), and low-resolution electromagnetic tomography (LORETA). The outcome of each study specifically in the subgenual cingulate or adjacent medial prefontal cortex is shown. Note that many studies showed additional changes not reported in this table.

| Population | Frequency | Side | Sessions | Modality | Outcome | Reference |
|---|---|---|---|---|---|---|
| Normal | High | Left | Single | SPECT | SG decrease | (25) |
| Normal | Low | Left | Single | PET | SG decrease | (26) |
| Depression | High | Left | Repeated | LORETTA | SG decrease | (27) |
| Depression | Low | Right | Repeated | SPECT | SG decrease | (7) |
| Depression | Low | Right | Repeated | SPECT | SG decrease | (8) |
| Normal | High | Left | Single | PET | MPF decrease | (16) |
| Normal | Low | Left | Single | fMRI | MPF decrease | (28) |
| Depression | High | Left | Repeated | SPECT | MPF decrease | (29) |
| Normal | Low | Left | Single | fMRI | No change | (30) |
| Normal | Low | Left | Repeated | PET | No change | (33) |
| Normal | Low | Right | Single | PET | No change | (31) |
| Normal | Low or High | Left or Right | Single | PET | No change | (32) |
| Depression | Low | Left | Repeated | PET | No change | (34) |
| Depression | High | Left | Repeated | PET | MPF increase | (34) |

Figure 20A:
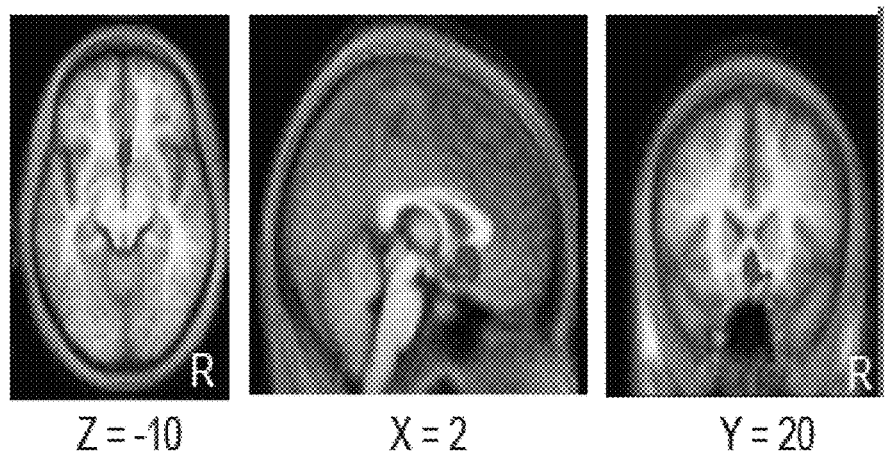
FIG. 20A: The ROI in the subgenual cingulate cortex is displayed in volume space.
Figure 20B:
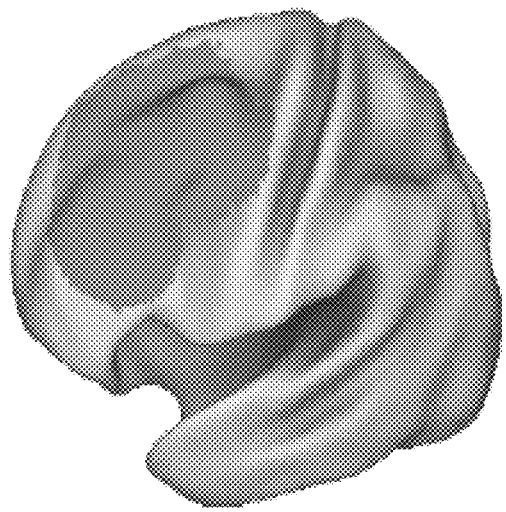
FIG. 20B: The large ROI designed to cover the entire left dorsal-lateral prefrontal cortex and used as a template for some analyses is shown on a lateral/oblique view of the left hemisphere.

Figure Legends:

FIG. 20: A priori defined regions of interest (ROI) not otherwise shown in the primary figures. FIG. 20A) The ROI in the subgenual cingulate cortex is displayed in volume space. FIG. 20B) The large ROI designed to cover the entire left dorsal-lateral prefrontal cortex and used as a template for some analyses is shown on a lateral/oblique view of the left hemisphere.

Figure 21:
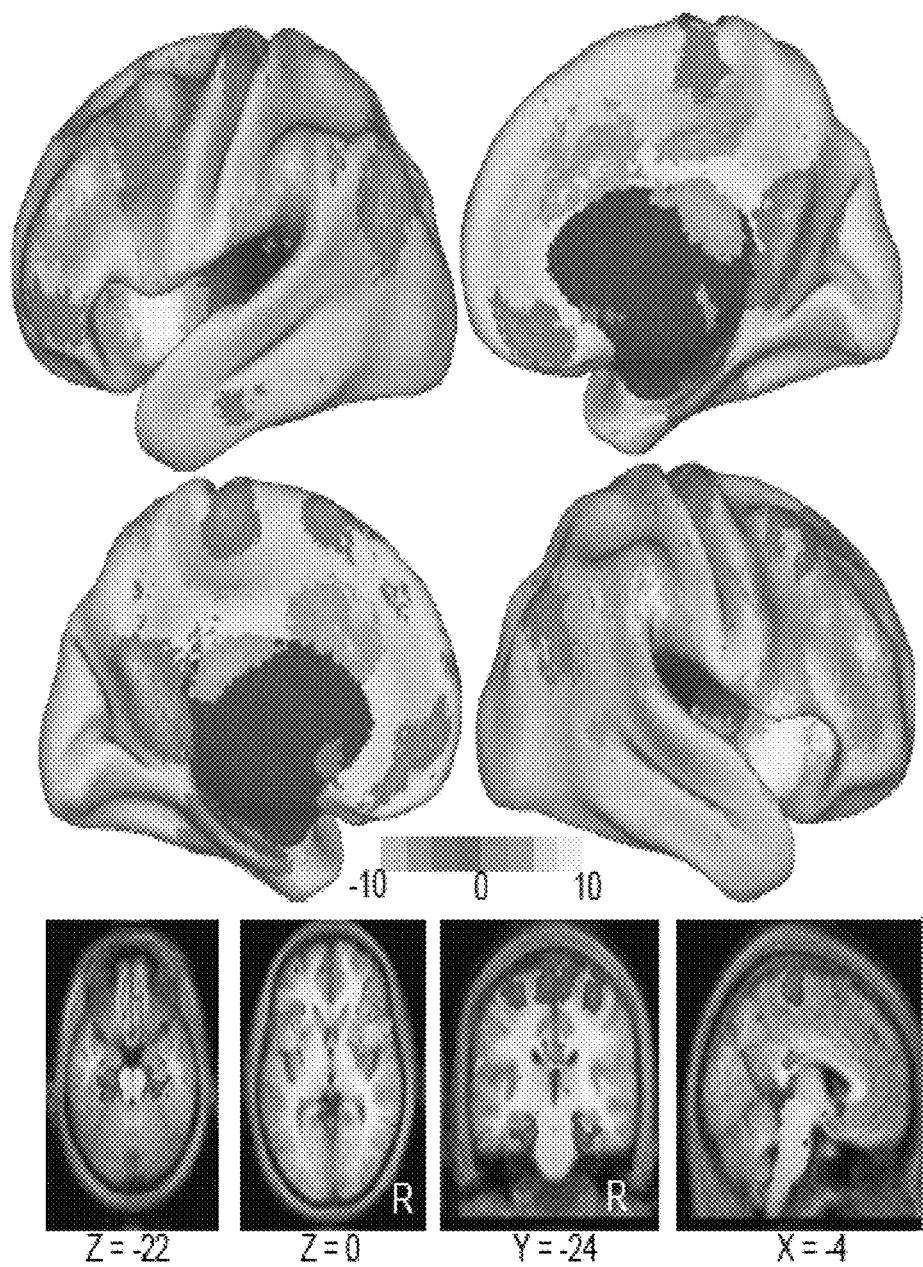
FIG. 21 illustrates differences in resting state functional connectivity between more effective versus less effective DLPFC stimulation sites, convergence of results across both comparisons. Shown are those voxels significantly more correlated with more effective versus less effective DLPFC TMS targets across both the Herbsman et al. 2009 (see FIG. 17B) and Fitzgerald et al. 2009 (see FIG. 17D) comparisons. Results are displayed both in surface space and in volume space.

FIG. 21: Differences in resting state functional connectivity between more effective versus less effective DLPFC stimulation sites, convergence of results across both comparisons. Shown are those voxels significantly more correlated with more effective versus less effective DLPFC TMS targets across both the Herbsman et al. 2009 (see FIG. 17B) and Fitzgerald et al. 2009 (see FIG. 17D) comparisons. Results are displayed both in surface space and in volume space.

Figures 22A, 22B, 22C:
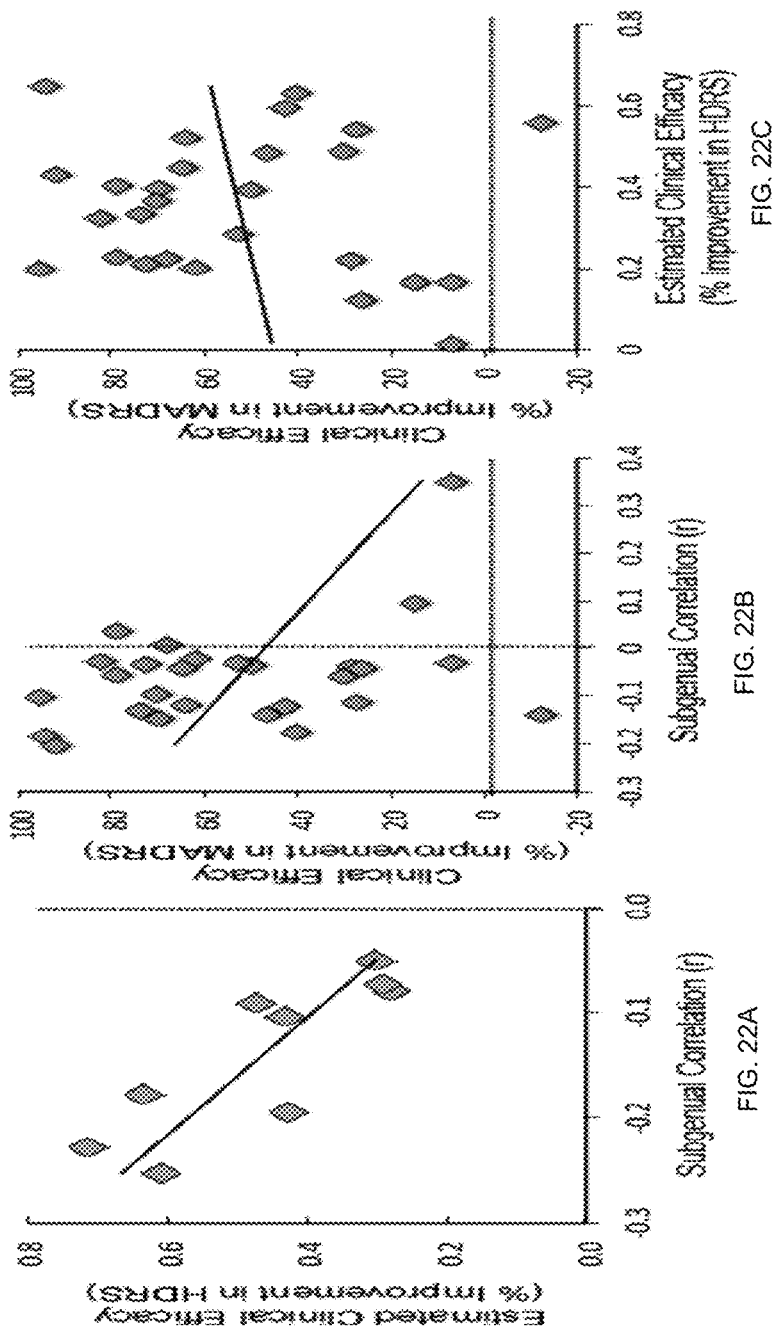
FIG. 22A illustrates relationship between reported clinical efficacy of different DLPFC stimulation sites and functional connectivity with the subgenual cingulate. Relationship between estimated equation-based clinical efficacy of different DLPFC stimulation sites and functional connectivity with the subgenual cingulate. For each DLPFC TMS target reported in the literature (see Table 2) the estimated clinical efficacy (per the empirically derived equation from Herbsman et al. 2009) versus the resting state correlation with the subgenual cingulate was plotted. More effective targets are more negatively correlated with the subgenual cingulate (r=−0.842, P<0.001 two-tailed).
FIG. 22B illustrates relationship between reported clinical efficacy of different DLPFC stimulation sites and functional connectivity with the subgenual cingulate. Replication of the relationship between clinical efficacy and functional connectivity with the subgenual cingulate for left DLPFC stimulation sites in individual patients and individual's antidepressant responses. For each patient-specific left DLPFC stimulation site in the study by Martinot et. al. [42], the reported clinical efficacy in that subject (change in the Montgomery & Asberg Depression Rating Scale) versus functional connectivity between that stimulation site and the subgenual was plotted. Again, more effective targets were more negatively correlated with the subgenual (r=−0.355, p<0.05 one-tailed)
FIG. 22C illustrates relationship between reported clinical efficacy of different DLPFC stimulation sites and functional connectivity with the subgenual cingulate. Lack of relationship between estimated clinical efficacy (per the Herbsman equation) and measured clinical efficacy in individual patients (using the Martinot dataset). For each patient-specific left DLPFC stimulation site in the study by Martinot et. al. [42], the reported clinical efficacy in that subject versus the estimated clinical efficacy as predicted by the Herbsman equation was plotted. Unlike the significant relationship with subgenual functional connectivity, there was no significant relationship between these variables suggesting that subgenual functional connectivity may capture variance not captured by the Herbsman equation (r=0.122, p>0.25 one-tailed).

FIG. 22: Relationship between reported clinical efficacy of different DLPFC stimulation sites and functional connectivity with the subgenual cingulate. FIG. 22A) Relationship between estimated equation-based clinical efficacy of different DLPFC stimulation sites and functional connectivity with the subgenual cingulate. For each DLPFC TMS target reported in the literature (see Table 2) we plotted the estimated clinical efficacy (per the empirically derived equation from Herbsman et al. 2009) versus the resting state correlation with the subgenual cingulate. More effective targets are more negatively correlated with the subgenual cingulate ($r=-0.842$, $P<0.001$ two-tailed). FIG. 22B) Replication of the relationship between clinical efficacy and functional connectivity with the subgenual cingulate for left DLPFC stimulation sites in individual patients and individual's antidepressant responses. For each patient-specific left DLPFC stimulation site in the study by Martinot et. al. [42], we plotted the reported clinical efficacy in that subject (change in the Montgomery & Asberg Depression Rating Scale) versus functional connectivity between that stimulation site and the subgenual. Again, more effective targets were more negatively correlated with the subgenual (r=−0.355, p<0.05 one-tailed) FIG. 22C) Lack of relationship between estimated clinical efficacy (per the Herbsman equation) and measured clinical efficacy in individual patients (using the Martinot dataset). For each patient-specific left DLPFC stimulation site in the study by Martinot et. al. [42], we plotted the reported clinical efficacy in that subject versus the estimated clinical efficacy as predicted by the Herbsman equation Unlike the significant relationship with subgenual functional connectivity, there was no significant relationship between these variables suggesting that subgenual functional connectivity may capture variance not captured by the Herbsman equation (r=0.122, p>0.25 one-tailed).

FIG. 23: Replication of principal findings in 11 control subjects from the same dataset as the 13 depressed patients. Time course correlations are shown between regions of interest in the dorsal lateral prefrontal cortex (DLPFC) and the subgenual seed region (FIGS. 23A-23C) or the efficacy-based seed map (FIGS. 23D-23F). There is an anticorrelation between TMS targets in the DLPFC and the subgenual (FIG. 23A). Paired comparisons show a trend towards stronger anticorrelation with more effective sites (FIG. 23B). The relationship between estimated clinical efficacy (using the Herbsman equation) and anticorrelation with the subgenual is similar to that previously observed (FIG. 23C; $r^2=0.34$, P=0.051). Using the efficacy-based seed map rather than the small subgenual seed region produces similar but more significant results including examination of regional time course correlations (FIG. 23D), paired comparisons (FIG. 23E), and the correlation between functional connectivity and estimated clinical efficacy (FIG. 23F; $r^2=0.73$, P<0.005). Labels for DLPFC ROIs are as in FIGS. 16 and 17A-17F with the addition of optimized DLPFC targets identified in normal subjects using the subgenual seed region (SO Target) and the efficacy-based seed map (SM Target). *P<0.05, P<0.001, *P<$10^{-4}$. Overall, this small population of 11 subjects shows the same pattern of results seen in both our original population of 98 normal subjects and the 13 subjects with depression. There are no significant differences between these 11 normal subjects and the 13 subjects with depression from the same dataset.

REFERENCES FOR SUPPLEMENTAL INFORMATION

1. Yeo B T, Krienen F M, Sepulcret Sabuncu M R, Lashkari D, Hollinshead M, et al. (2011): The Organization of the Human Cerebral Cortex Estimated By Functional Connectivity. *Journal of neurophysiology.*
2. van der Kouwe A J, Benner T, Salat D H, Fisch! B (2008): Brain morphometry with multiecho MPRAGE. *Neurolmage.* 40:559-569.
3. Wu J, Buchsbaum M S, Gillin J C, Tang C, Cadwell S, Wiegand M, et al. (1999): Prediction of antidepressant effects of sleep deprivation by metabolic rates in the ventral anterior cingulate and medial prefrontal cortex. *Am J Psychiatry.* 156:1149-1158.
4. Mayberg H S, Brannan S K, Tekell J L, Silva J A, Mahurin R K, McGinnis S, et al. (2000): Regional metabolic effects of fluoxetine in major depression: serial changes and relationship to clinical response. *Biol Psychiatry.* 48:830-843.
5. Drevets W C, Bogers W, Raichle M E (2002): Functional anatomical correlates of antidepressant drug treatment assessed using PET measures of regional glucose metabolism. *Eur Neuropsychopharmacol.* 12:527-544.
6. Mayberg H S, Lozano A M, Voon V, McNeely H E, Seminowicz D, Hamani C, et al. (2005): Deep brain stimulation for treatment-resistant depression. *Neuron.* 45:651-660.
7. Kito S, Fujita K, Koga Y (2008): Regional cerebral blood flow changes after low-frequency transcranial magnetic stimulation of the right dorsolateral prefrontal cortex in treatment-resistant depression. *Neuropsychobiology.* 58:29-36.
8. Kito S, Hasegawa T, Koga Y (2011): Neuroanatomical correlates of therapeutic efficacy of low-frequency right prefrontal transcranial magnetic stimulation in treatment-resistant depression. *Psychiatry Clin Neurosci.* 65:175-182.
9. Nahas Z, Teneback C, Chae J H, Mu Q, Molnar C, Kozel F A, et al. (2007): Serial vagus nerve stimulation functional MRI in treatment-resistant depression. *Neuropsychopharmacology.* 32:1649-1660.
10. Talairach J, Tournoux P (1988): *Co-Planar Stereotaxic Atlas of the Human Brain.* New York: Thieme Medical Publishers, Inc.
11. Fitzgerald P B, Hoy K, McQueen S, Mailer A, Herring S, Segrave R, et al. (2009): A randomized trial of rTMS targeted with MRI based neuro-navigation in treatment-resistant depression. *Neuropsychopharmacology.* 34:1255-1262.
12. Herbsman T, Avery D, Ramsey D, Holtzheimer P, Wadjik C, Hardaway F, et al. (2009): More lateral and anterior prefrontal coil location is associated with better repetitive transcranial magnetic stimulation antidepressant response. *Biol Psychiatry.* 66:509-515.
13. Rusjan P M, Barr M S, Farzan F, Arenovich T, Mailer ii, Fitzgerald P B, et al. (2010): Optimal transcranial magnetic stimulation coil placement for targeting the dorsolateral prefrontal cortex using novel magnetic resonance image-guided neuronavigation. *Human brain mapping.* 31:1643-1652.
14. Herwig U, Padberg F, Unger J, Spitzer M, Schonfeldt-Lecuona C (2001): Transcranial magnetic stimulation in therapy studies: examination of the reliability of "standard" coil positioning by neuronavigation. *Biol Psychiatry.* 50:58-61.
15. Cho S S, Strafella A P (2009): rTMS of the left dorsolateral prefrontal cortex modulates dopamine release in the ipsilateral anterior cingulate cortex and orbitofrontal cortex. *PloS one.* 4:e6725.
16. Paus T, Castro-Alamancos Ma, Petrides M (2001): Cortico-cortical connectivity of the human mid-dorsolateral frontal cortex and its modulation by repetitive transcranial magnetic stimulation. *European Journal of Neuroscience.* 14:1405-1411.
17. Rajkowska G, Goldman-Rakic P S (1995): Cytoarchitectonic definition of prefrontal areas in the normal human cortex: II. Variability in locations of areas 9 and 46 and relationship to the Talairach Coordinate System. *Cereb Cortex.* 5:323-337.
18. Paillere Martinot M-L, Galinowski A, Ringuenet D, Gallarda T, Lefaucheur J-P, Bellivier F, et al. (2010): Influence of prefrontal target region on the efficacy of repetitive transcranial magnetic stimulation in patients with medication-resistant depression: a [(18)F1-fluorodeoxyglucose PET and MRI study. The international journal of neuropsychopharmacology official scientific journal of the Collegium Internationale Neuropsychopharmacologicum (CINP). 13:45-59.
19. Herwig U, Satrapi P, Schonfeldt-Lecuona C (2003): Using the international 10-20 EEG system for positioning of transcranial magnetic stimulation. Brain Topogr. 16:95-99.
20. Wagner T, Valero-Cabre A, Pascual-Leone A (2007): Noninvasive human brain stimulation. Annual review of biomedical engineering. 9:527-565.
21. Fox M D, Snyder A Z, Vincent R., Corbetta M, Van Essen D C, Raichle M E (2005): The human brain is intrinsically organized into dynamic, anticorrelated functional networks. PNAS. 102:9673-9678.
22. Van Dijk K R, Hedden T, Venkataraman A, Evans K C, Lazar S W, Buckner R L (2010): Intrinsic functional connectivity as a tool for human connectomics: theory, properties, and optimization. Journal of neurophysiology. 103:297-321.
23. Fox M D, Corbetta M, Snyder A Z, Vincent J L, Raichle M E (2006): Spontaneous neuronal activity distinguishes human dorsal and ventral attention systems. PNAS. 103: 10046-10051.
24. Van Essen D C (2005): A population-average, landmark- and surface-based (PALS) atlas of human cerebral cortex. Neuroimage. 28:635-662.
25. George M S, Stallings L E, Speer A M, Nahas Z, Spicer K M, Vincent D J, et al. (1999): Prefrontal repetitive transcranial magnetic stimulation (rTMS) changes relative perfusion locally and remotely. Human Psychopharmacology: Clinical and Experimental. 14:161-170.
26. Kimbrell Ta, Dunn R T, George M S, Danielson A L, Willis M W, Repella J D, et al. (2002): Left prefrontal-repetitive transcranial magnetic stimulation (rTMS) and regional cerebral glucose metabolism in normal volunteers. Psychiatry research. 115:101-113.
27. Narushima K, McCormick L M, Yamada T, Thatcher R W, Robinson R G (2010): Subgenual cingulate theta activity predicts treatment response of repetitive transcranial magnetic stimulation in participants with vascular depression. The Journal of neuropsychiatry and clinical neurosciences. 22:75-84.
28. Li X, Na has Z, Kozel F A, Anderson B, Bohning D E, George M S (2004): Acute left prefrontal transcranial magnetic stimulation in depressed patients is associated with immediately increased activity in prefrontal cortical as well as subcortical regions. Biological psychiatry. 55:882-890.
29. Teneback C C, Nahas Z, Speer A M, Molloy M, Stallings L E, Spicer K M, et al. (1999): Changes in prefrontal cortex and paralimbic activity in depression following two weeks of daily left prefrontal TMS. Journal of Neuropsychiatry and Clinical Neurosciences. 11:426.
30. Nahas Z, Lomarev M, Roberts D R, Shastri a, Lorberbaum J P, Teneback C, et al. (2001): Unilateral left prefrontal transcranial magnetic stimulation (TMS) produces intensity-dependent bilateral effects as measured by interleaved BOLD fMRI. Biological psychiatry. 50:712-720.
31. Eisenegger C, Treyer V, Fehr E, Knoch D (2008): Time-course of "off-line" prefrontal rTMS effects—a PET study. NeuroImage. 42:379-384. Knoch D, Treyer V, Regard M, Muri R M, Buck A, Weber B (2006): Lateralized and frequency-dependent effects of prefrontal rTMS on regional cerebral blood flow. NeuroImage. 31:641-648.
32. Speer A M, Willis M W, Herscovitch P, Daube-Witherspoon M, Shelton J R, Benson B E, et al. (2003): Intensity-dependent regional cerebral blood flow during 1-Hz repetitive transcranial magnetic stimulation (rTMS) in healthy volunteers studied with H2150 positron emission tomography: II. Effects of prefrontal cortex rTMS. Biological psychiatry. 54:826-832.
33. Speer aM, Kimbrell Ta, Wassermann E M, D Repella J, Willis M W, Herscovitch P, et al. (2000): Opposite effects of high and low frequency rTMS on regional brain activity in depressed patients. Biological psychiatry. 48:1133-1141.

Having thus described several aspects of at least one embodiment, it is to be appreciated that various alterations, modifications, and improvements will readily occur to those skilled in the art.

Such alterations, modifications, and improvements are intended to be part of this disclosure, and are intended to be within the spirit and scope of the embodiments. Further, though advantages of the embodiments are indicated, it should be appreciated that not every embodiment will include every described advantage. Some embodiments may not implement any features described as advantageous herein and in some instances. Accordingly, the foregoing description and drawings are by way of example only.

What is claimed is:
1. A method of operating a computing device comprising at least one processor to identify target sites for application of transcranial magnetic stimulation (TMS) to a patient, the method comprising:
by the at least one processor:
receiving a plurality of functional magnetic resonance imaging (fMRI) images obtained over a duration of time while the patient is in a resting state, wherein the plurality of fMRI images include voxels of the patient's brain and values for the voxels that are indicative of intrinsic brain activity of the patient;
identifying, in at least one fMRI image of the plurality of fMRI images, a portion of the voxels as at least one region of interest of the patient's brain, wherein stimulating the at least one region of interest affects at least one of a neurological or psychiatric condition of a person;
analyzing the plurality of fMRI images to determine at least one target TMS stimulation site in a target region of the patient's brain that is functionally connected to the at least one region of interest of the patient's brain, wherein determining the at least one target TMS stimulation site comprises:
generating a seed map that includes the at least one region of interest and voxels outside the at least one region of interest that are functionally connected to the at least one region of interest;
modifying the seed map by subtracting voxels corresponding to the target region of the patient's brain; and
comparing, over the duration of time, values for voxels corresponding to the modified seed map and values for voxels corresponding to the target region to identify a group of voxels in the target region that correlates negatively with the modified seed map over the duration of time; and generating an output comprising the at least one determined target TMS stimulation site as a region of the patient's brain corresponding to the identified group of voxels.

2. The method of claim 1, further comprising:
providing the generated output to a location where TMS is applied to the brain of the patient at the at least one determined target TMS stimulation site.

3. The method of claim 1, further comprising:
obtaining the plurality of fMRI images of at least a portion of the brain of the patient using functional connectivity magnetic resonance imaging (fcMRI).

4. The method of claim 1, wherein:
analyzing the plurality of fMRI images comprises determining functional connectivity between the at least one target stimulation site and the modified seed map by determining at least one correlation coefficient between the modified seed map and the at least one target stimulation site as being above a threshold value.

5. The method of claim 1, wherein:
the at least one target TMS stimulation site is determined on the left dorsolateral prefrontal cortex of the brain of the patient.

6. The method of claim 5, wherein:
the at least one region of interest of the patient's brain comprises at least one subgenual cingulate region that is functionally connected with the left dorsolateral prefrontal cortex.

7. The method of claim 6, wherein:
determining the at least one target TMS stimulation site of the patient's brain further comprises identifying where activity of the at least one target TMS stimulation site correlates negatively with activity of the at least one subgenual cingulate region.

8. The method of claim 1, further comprising:
determining a size of at least one TMS coil.

9. The method of claim 1, wherein:
analyzing the plurality of fMRI images comprises computing a functional connectivity map based on the at least one region of interest.

10. The method of claim 9, wherein:
determining the at least one target TMS stimulation site of the brain of the patient comprises calculating coordinates of the at least one target TMS stimulation site on a surface of the brain of the patient based on the functional connectivity map.

11. The method of claim 10, wherein:
the coordinates comprise multi-dimensional coordinates.

12. The method of claim 1, wherein:
the at least one of the neurological or psychiatric condition comprises at least one selected from the group consisting of depression, Parkinson's, dystonia, essential tremor, eplilepsy, OCD, bipolar, coma, Alzheimer's, autism, stroke, aphasia, and hemiparesis.

13. The method of claim 1, wherein analyzing the plurality of fMRI images to determine at least one target TMS stimulation site further comprises extracting at least one time course for the modified seed map by averaging values for at least a portion of the voxels in the seed map and correlating the at least one time course to values for voxels outside the modified seed map to identify the group of voxels as the at least one target TMS stimulation site.

14. The method of claim 1, wherein identifying, in at least one fMRI image of the plurality of fMRI images, a portion of voxels as at least one region of interest further comprises identifying the portion of voxels based at least in part on coordinates identified from a previously defined region of interest.

15. A system for identifying target stimulation sites for application of transcranial magnetic stimulation (TMS) to a patient, the system comprising:
at least one processor configured to:
receive a plurality of functional magnetic resonance imaging (fMRI) images obtained over a duration of time while the patient is in a resting state, wherein the plurality of fMRI images include voxels of the patient's brain and values for the voxels that are indicative of intrinsic brain activity of the patient;
identify, in at least one fMRI image of the plurality of fMRI images, a portion of the voxels as at least one region of interest of the patient's brain, wherein stimulating the at least one region of interest affects at least one of a neurological or psychiatric condition of a person; and
analyze the plurality of fMRI images to determine at least one target TMS stimulation site in a target region of the patient's brain that is functionally connected to the at least one region of interest of the patient's brain, wherein determining the at least one target TMS stimulation site comprises:
generating a seed map that includes the at least one region of interest and voxels outside the at least one region of interest that are functionally connected to the at least one region of interest;
modifying the seed map by subtracting voxels corresponding to the target region of the patient's brain; and
comparing, over the duration of time, values for voxels corresponding to the modified seed map and values for voxels corresponding to the target region to identify a group of voxels in the target region that correlates negatively with the modified seed map over the duration of time, wherein the at least one target TMS stimulation site includes a region of the patient's brain corresponding to the identified group of voxels; and
a TMS device configured to apply TMS to the brain of the patient at the at least one determined target TMS stimulation site to treat at least one of the neurological or psychiatric disorder.

16. The system of claim 15, wherein:
analyzing the plurality of fMRI images comprises determining functional connectivity between the at least one target stimulation site and the modified seed map by identifying at least one correlation coefficient between the modified seed map and the at least one target stimulation site as being above a threshold value.

17. The system of claim 15, further comprising a magnetic resonance imaging (MRI) device configured to obtain the plurality of fMRI images of at least a portion of the brain of the patient.

18. The system of claim 17, wherein:
the MRI device is configured to perform functional connectivity MRI (fcMRI).

19. The system of claim 15, wherein:
the at least one of the neurological or psychiatric condition comprises at least one selected from the group consisting of depression, Parkinson's, dystonia, essential tremor, eplilepsy, OCD, bipolar, coma, Alzheimer's, autism, stroke, aphasia, and hemiparesis.

* * * * *